(12) United States Patent
Harris et al.

(10) Patent No.: US 7,615,648 B2
(45) Date of Patent: Nov. 10, 2009

(54) AMINOMETHYL-AZACYCLE DERIVATIVES AS INHIBITORS OF MONOAMINE UPTAKE

(75) Inventors: John Richard Harris, Basingstoke (GB); Barry Peter Clark, Basingstoke (GB); Peter Thaddeus Gallagher, Basingstoke (GB); Maria Ann Whatton, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 11/568,641

(22) PCT Filed: May 19, 2005

(86) PCT No.: PCT/US2005/017436

§ 371 (c)(1),
(2), (4) Date: Nov. 3, 2006

(87) PCT Pub. No.: WO2005/118531

PCT Pub. Date: Dec. 15, 2005

(65) Prior Publication Data

US 2008/0004330 A1      Jan. 3, 2008

Related U.S. Application Data

(60) Provisional application No. 60/576,059, filed on Jun. 1, 2004.

(51) Int. Cl.
*C07D 207/00* (2006.01)
*A01N 43/36* (2006.01)
(52) U.S. Cl. ...................................... 548/566; 514/408
(58) Field of Classification Search ...................... None
See application file for complete search history.

(56) References Cited

U.S. PATENT DOCUMENTS 5,571,832 A      11/1996   De Costa et al.

FOREIGN PATENT DOCUMENTS

WO      WO 2005/000811  A1      1/2005

OTHER PUBLICATIONS

Shireman et al., Bioorg. Med. Chem. Lett., 18(2008), 2103-2108.*
Asami et al., caplus an 1979:22716.*

* cited by examiner

*Primary Examiner*—Golam M. M. Shameem
*Assistant Examiner*—Sun Jae Y Loewe
(74) *Attorney, Agent, or Firm*—Mark A. Winter; Tonya L. Combs

(57) ABSTRACT

The present invention provides compounds of formula (I) wherein A is (1), (2), (3), (4), (5), (6) or (7) and wherein R1, R7, y and Ar₁ are defined herein. The compounds are inhibitors of the uptake of one or more monoamines selected from serotonin, norepinephrine and dopamine and, as such, may be useful in the treatment of disorders of the central and/or peripheral nervous system.

7 Claims, No Drawings

AMINOMETHYL-AZACYCLE DERIVATIVES AS INHIBITORS OF MONOAMINE UPTAKE

This application is a United States national phase entry, pursuant to 35 U.S.C. 371, of PCT/US2005/017436, filed May 19, 2005, which claims the benefit of U.S. provisional patent application Ser. No. 60/576,059, filed Jun. 1, 2004.

The present invention is directed to compounds which inhibit the uptake of one or more physiologically active monoamines selected from serotonin (also called 5-hydroxytryptamine or 5-HT), norepinephrine (also called noradrenaline) and dopamine. There is a large body of scientific evidence pointing to the physiological role of these monoamines as neurotransmitters. Consequently, compounds which are capable of inhibiting the uptake of one or more of these monoamines find utility in the treatment of disorders of the central and/or peripheral nervous system.

Many compounds exhibiting this kind of pharmacology are known in the art. For example, it is known that the 3-aryloxy-3-substituted-1-aminopropane class of compounds have demonstrated particular diversity in their ability to inhibit the uptake of monoamines. Fluoxetine (N-methyl 3-((4-trifluoromethylphenyl)oxy)-3-phenyl-1-aminopropane hydrochloride), for example, is a selective serotonin uptake inhibitor that has found great market acceptance in the treatment of depression and has also been approved for the treatment of a number of other disorders. Atomoxetine ((−)-N-methyl 3-((2-methylphenyl)oxy)-3-phenyl-1-aminopropane hydrochloride), is a selective norepinephrine uptake inhibitor that is approved for the treatment of attention deficit/hyperactivity disorder. Duloxetine ((+)-N-methyl 3-(1-naphthalenyloxy)-3-(2-thienyl)-1-aminopropane hydrochloride), is a dual serotonin and norepinephrine uptake inhibitor that is in clinical development for the treatment of depression and stress urinary incontinence. WO2004/052858, WO2005/000811 and WO2005/000305 disclose N,N-disubstituted-4-aminopiperidines, N,N-disubstituted-3-aminopyrrolidines, N,N-disubstituted-3-aminopiperidines, and N,N-disubstituted-3-aminoquinuclidines respectively as inhibitors of monoamine reuptake.

Despite the existence of such known compounds, it would be advantageous to provide further compounds which are capable of inhibiting the uptake of one or more monoamines selected from serotonin, norepinephrine and dopamine. Preferably, such compounds would exhibit one or more of the following characteristics—(i) potency in their inhibition of one or more of these monoamines, (ii) selectivity in their inhibition of one or more of these monoamines, (iii) bioavailability, (iv) minimal interaction with metabolic enzymes such as CYP2D6 and (v) acid stability.

The present invention provides a compound of formula (I)

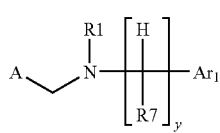

(I)

wherein
A is

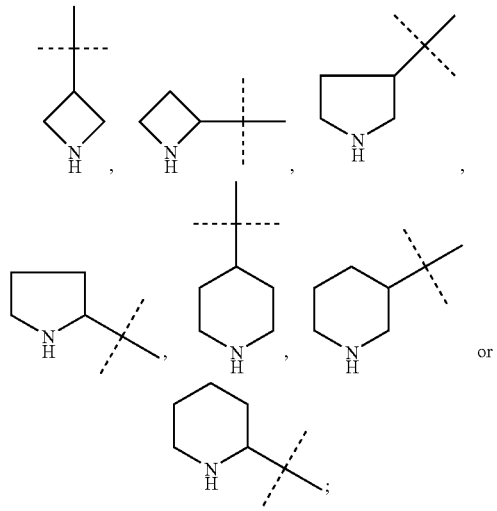

R1 is $C_2$-$C_{10}$alkyl, $C_2$-$C_{10}$alkenyl, $C_3$-$C_8$cycloalkyl, $C_4$-$C_8$cycloalkenyl, $C_4$-$C_{10}$cycloalkylalkyl, $C_5$-$C_{10}$cycloalkenylalkyl, 8-oxabicyclo[3.2.1]oct-6endo-yl or —$(CH_2)_p$—$Ar_2$ wherein p is 0, 1 or 2, wherein one —$CH_2$— within any cycloalkyl group is optionally substituted by —O— or —S— and wherein each group is optionally substituted with from 1 to 7 halogen substituents and/or with from 1 to 3 substituents each independently selected from hydroxy, cyano, $C_1$-$C_4$alkyl, —S—($C_1$-$C_4$alkyl) (optionally substituted with from 1 to 3 halogen atoms) and —O—($C_1$-$C_4$alkyl) (optionally substituted with from 1 to 3 halogen atoms);

R7 is independently at each occurrence selected from H and $C_1$-$C_4$alkyl;

y is 1, 2 or 3;

$Ar_1$ is selected from:

(i) a phenyl group or a 5- or 6-membered monocyclic heteroaromatic group each of which is optionally substituted with 1, 2, 3, 4 or 5 substituents (depending on the number of available substitution positions) each independently selected from halo, cyano, $C_1$-$C_4$alkyl (optionally substituted with from 1 to 7 halogen atoms), —O—($C_1$-$C_4$alkyl) (optionally substituted with from 1 to 7 halogen atoms) —$CO_2$($C_1$-$C_4$alkyl), and —$S(O)_q$—($C_1$-$C_4$alkyl) wherein q is 0, 1 or 2 (optionally substituted with from 1 to 7 halogen atoms) and/or with 1 substituent selected from pyridinyl, pyrazolyl, phenyl (optionally substituted with from 1 to 3 substituents each independently selected from halogen, $C_1$-$C_4$alkyl and —O—($C_1$-$C_4$alkyl)), benzyl (optionally substituted with from 1 to 3 substituents each independently selected from halogen, $C_1$-$C_4$alkyl and —O—($C_1$-$C_4$alkyl)) and phenoxy (optionally substituted with from 1 to 3 substituents each independently selected from halogen, $C_1$-$C_4$alkyl and —O—($C_1$-$C_4$alkyl)) with the proviso that only $C_1$-$C_4$alkyl may be a substituent for the H of any —NH— moiety present within a 5- or 6-membered monocyclic heteroaromatic group; or (ii) a naphthyl group or an 8-, 9- or 10-membered bicyclic heteroaromatic group each of which is optionally substituted with 1, 2, 3, 4, 5 or 6 substituents (depending on the number of available substitution positions) each independently selected from halo, cyano, $C_1$-$C_4$alkyl (optionally substituted with from 1 to 7 halogen atoms), —O—($C_1$-$C_4$alkyl) (optionally substituted with from 1 to 7 halogen atoms) and —S—($C_1$-$C_4$alkyl) (optionally substituted with from 1 to 7 halogen atoms) with the proviso that only $C_1$-$C_4$alkyl may be a substituent for the H of any —NH— moiety present within an 8-, 9- or 10-membered bicyclic heteroaromatic group; and $Ar_2$ is selected from
(i) a phenyl group or a 5- or 6-membered monocyclic heteroaromatic group each of which is optionally substituted with 1, 2, 3, 4 or 5 substituents (depending on the number of available substitution positions) each independently selected from halo, cyano, $C_1$-$C_4$alkyl (optionally substituted with from 1 to 7 halogen atoms), —O—($C_1$-$C_4$alkyl) (optionally substituted with from 1 to 7 halogen atoms), —$CO_2$($C_1$-$C_4$alkyl) and —$S(O)_q$—($C_1$-$C_4$alkyl) wherein q is 0, 1 or 2 (optionally substituted with from 1 to 7 halogen atoms) with the proviso that only $C_1$-$C_4$alkyl may be a substituent for the H of any —NH— moiety present within a 5- or 6-membered monocyclic heteroaromatic group; or
(ii) a naphthyl group or an 8-, 9- or 10-membered bicyclic heteroaromatic group each of which is optionally substituted with 1, 2, 3, 4, 5 or 6 substituents (depending on the number of available substitution positions) each independently selected from halo, cyano, $C_1$-$C_4$alkyl (optionally substituted with from 1 to 7 halogen atoms), —O—($C_1$-$C_4$alkyl) (optionally substituted with from 1 to 7 halogen atoms) and —S—($C_1$-$C_4$alkyl) (optionally substituted with from 1 to 7 halogen atoms) with the proviso that only $C_1$-$C_4$alkyl may be a substituent for the H of any —NH— moiety present within an 8-, 9- or 10-membered bicyclic heteroaromatic group;

or a pharmaceutically acceptable salt thereof.

In another embodiment, the present invention provides a compound of formula (I) as defined above, or a pharmaceutically acceptable salt thereof, for use in therapy.

In another embodiment, the present invention provides a method of inhibiting the uptake of one or more monoamines selected from serotonin, dopamine and norepinephrine in a mammal, comprising administering to a mammal in need of such inhibition an effective amount of a compound of formula (I) as defined above, or a pharmaceutically acceptable salt thereof.

In another embodiment, the present invention provides for the use of a compound of formula (I) as defined above, or a pharmaceutically acceptable salt thereof, for the manufacture of a medicament for inhibiting the uptake of one or more monoamines selected from serotonin, dopamine and norepinephrine.

In another embodiment, the present invention provides a pharmaceutical composition comprising a compound of formula (I) as defined above, or a pharmaceutically acceptable salt thereof, together with a pharmaceutically acceptable diluent, excipient or carrier.

In the present specification the term "$C_2$-$C_{10}$alkyl" means a monovalent unsubstituted saturated straight-chain or branched-chain hydrocarbon radical having from 2 to 10 carbon atoms.

In the present specification the term "$C_2$-$C_{10}$alkenyl" means a monovalent unsubstituted unsaturated straight-chain or branched-chain hydrocarbon radical having from 2 to 10 carbon atoms and containing at least one (and preferably only one) carbon-carbon double bond.

In the present specification the term "$C_3$-$C_8$cycloalkyl" means a monovalent unsubstituted saturated monocyclic or bicyclic hydrocarbon radical having from 3 to 8 carbon atoms.

In the present specification the term "$C_4$-$C_8$cycloalkenyl" means a monovalent unsubstituted unsaturated monocyclic or bicyclic hydrocarbon radical having from 4 to 8 carbon atoms and containing one carbon-carbon double bond.

In the present specification the term "$C_4$-$C_{10}$cycloalkylalkyl" means a monovalent unsubstituted saturated monocyclic or bicyclic hydrocarbon radical having from 3 to 9 carbon atoms, linked to the point of substitution via a divalent unsubstituted saturated straight-chain or branched-chain hydrocarbon radical having at least 1 carbon atom.

In the present specification the term "$C_5$-$C_{10}$cycloalkenylalkyl" means a monovalent unsubstituted unsaturated monocyclic or bicyclic hydrocarbon radical having from 4 to 9 carbon atoms and containing one carbon-carbon double bond, linked to the point of substitution via a divalent unsubstituted saturated straight-chain or branched-chain hydrocarbon radical having at least 1 carbon atom.

In the present specification the term "halo" or "halogen" means F, Cl, Br or I.

In the present specification the term "5- or 6-membered monocyclic heteroaromatic group" means a monocyclic aromatic group with a total of 5 or 6 atoms in the ring wherein from 1 to 4 of those atoms are each independently selected from N, O and S. Preferred groups have 1 or 2 atoms in the ring which are each independently selected from N, O and S. Suitable 5-membered monocyclic heteroaromatic groups include pyrrolyl (also called azolyl), furanyl, thienyl, pyrazolyl (also called 1H-pyrazolyl and 1,2-diazolyl), imidazolyl, oxazolyl (also called 1,3-oxazolyl), isoxazolyl (also called 1,2-oxazolyl), thiazolyl (also called 1,3-thiazolyl), isothiazolyl (also called 1,2-thiazolyl), triazolyl, oxadiazolyl, thiadiazolyl, tetrazolyl, oxatriazolyl and thiatriazolyl. Suitable 6-membered monocyclic heteroaromatic groups include pyridinyl, pyrimidyl, pyrazinyl, pyridazinyl and triazinyl.

"Pyrrolyl" as used herein includes pyrrol-2-yl and pyrrol-3-yl.

"Furanyl" as used herein includes furan-2-yl and furan-3-yl.

"Thienyl" as used herein includes thien-2-yl and thien-3-yl.

"Pyrazolyl" as used herein includes pyrazol-3-yl, pyrazol-4-yl and pyrazol-5-yl.

"Imidazolyl" as used herein includes imidazol-2-yl, imidazol-4-yl and imidazol-5-yl.

"Oxazolyl" as used herein includes oxazol-2-yl, oxazol-4-yl and oxazol-5-yl.

"Isoxazolyl" as used herein includes isoxazol-3-yl, isoxazol-4-yl, and isoxazol-5-yl.

"Thiazolyl" as used herein includes thiazol-2-yl, thiazol-4-yl and thiazol-5-yl.

"Isothiazolyl" as used herein includes isothiazol-3-yl, isothiazol-4-yl, and isothiazol-5-yl.

"Triazolyl" as used herein includes 1,2,3-triazol-1-yl, 1,2,3-triazol-4-yl, 1,2,3-triazol-5-yl, 1,2,4-triazol-1-yl, 1,2,4-triazol-3-yl and 1,2,4-triazol-5-yl.

"Oxadiazolyl" as used herein includes 1,2,3-oxadiazol-4-yl, 1,2,3-oxadiazol-5-yl, 1,2,4-oxadiazol-3-yl, 1,2,4-oxadiazol-5-yl, 1,2,5-oxadiazol-3-yl and 1,3,4-oxadiazol-2-yl.

"Thiadiazolyl" as used herein includes 1,2,3-thiadiazol-4-yl, 1,2,3-thiadiazol-5-yl, 1,2,4-thiadiazol-3-yl, 1,2,4-thiadiazol-5-yl, 1,2,5-thiadiazol-3-yl (also called furazan-3-yl) and 1,3,4-thiadiazol-2-yl.

"Tetrazolyl" as used herein includes tetrazol-1-yl and tetrazol-5-yl.

"Oxatriazolyl" as used herein includes 1,2,3,4-oxatriazol-5-yl and 1,2,3,5-oxatriazol-4-yl.

"Thiatriazolyl" as used herein includes 1,2,3,4-thiatriazol-5-yl and 1,2,3,5-thiatriazol-4-yl.

"Pyridinyl" as used herein includes pyridin-2-yl, pyridin-3-yl and pyridin-4-yl.

"Pyrimidyl" as used herein includes pyrimid-2-yl, pyrimid-4-yl, pyrimid-5-yl and pyrimid-6-yl.

"Pyridazinyl" as used herein includes pyridazin-3-yl and pyridazin-4-yl.

"Pyrazinyl" as used herein includes pyrazin-2-yl and pyrazin-3-yl.

"Triazinyl" as used herein includes 1,3,5-triazin-2-yl, 1,2,4-triazin-3-yl, 1,2,4-triazin-5-yl, 1,2,4-triazin-6-yl, 1,2,3-triazin-4-yl and 1,2,3-triazin-5-yl.

In the present specification the term "naphthyl" includes 1-naphthyl, and 2-naphthyl. 1-naphthyl is preferred.

In the present specification the term "8-, 9- or 10-membered bicyclic heteroaromatic group" means a fused bicyclic aromatic group with a total of 8, 9 or 10 atoms in the ring system wherein from 1 to 4 of those atoms are each independently selected from N, O and S. Preferred groups have from 1 to 3 atoms in the ring system which are each independently selected from N, O and S. Suitable 8-membered bicyclic heteroaromatic groups include imidazo[2,1-b][1,3]thiazolyl, thieno[3,2-b]thienyl, thieno[2,3-d][1,3]thiazolyl and thieno[2,3-d]imidazolyl. Suitable 9-membered bicyclic heteroaromatic groups include indolyl, isoindolyl, benzofuranyl (also called benzo[b]furanyl), isobenzofuranyl (also called benzo[c]furanyl), benzothienyl (also called benzo[b]thienyl), isobenzothienyl (also called benzo[c]thienyl), indazolyl, benzimidazolyl, 1,3-benzoxazolyl, 1,2-benzisoxazolyl, 2,1-benzisoxazolyl, 1,3-benzothiazolyl, 1,2-benzoisothiazolyl, 2,1-benzoisothiazolyl, benzotriazolyl, 1,2,3-benzoxadiazolyl, 2,1,3-benzoxadiazolyl, 1,2,3-benzothiadiazolyl, 2,1,3-benzothiadiazolyl, thienopyridinyl, purinyl and imidazo[1,2-a]pyridine. Suitable 10-membered bicyclic heteroaromatic groups include quinolinyl, isoquinolinyl, cinnolinyl, quinazolinyl, quinoxalinyl, 1,5-naphthyridyl, 1,6-naphthyridyl, 1,7-naphthyridyl and 1,8-naphthyridyl.

"Imidazo[2,1-b][1,3]thiazolyl" as used herein includes imidazo[2,1-b][1,3]thiazol-2-yl, imidazo[2,1-b][1,3]thiazol-3-yl, imidazo[2,1-b][1,3]thiazol-5-yl and imidazo[2,1-b][1,3]thiazol-6-yl.

"Thieno[3,2-b]thienyl" as used herein includes thieno[3,2-b]thien-2-yl, thieno[3,2-b]thien-3-yl, thieno[3,2-b]thien-5-yl and thieno[3,2-b]thien-6-yl.

"Thieno[2,3-d][1,3]thiazolyl" as used herein includes thieno[2,3-d][1,3]thiazol-2-yl, thieno[2,3-d][1,3]thiazol-5-yl and thieno[2,3-d][1,3]thiazol-6-yl.

"Thieno[2,3-d]imidazolyl" as used herein includes thieno[2,3-d]imidazol-2-yl, thieno[2,3-d]imidazol-4-yl and thieno[2,3-d]imidazol-5-yl.

"Indolyl" as used herein includes indol-1-yl, indol-2-yl, indol-3-yl, indol-4-yl, indol-5-yl, indol-6-yl and indol-7-yl.

"Isoindolyl" as used herein includes isoindol-1-yl, isoindol-2-yl, isoindol-3-yl, isoindol-4-yl, isoindol-5-yl, isoindol-6-yl and isoindol-7-yl.

"Benzofuranyl" as used herein includes benzofuran-2-yl, benzofuran-3-yl, benzofuran-4-yl, benzofuran-5-yl, benzofuran-6-yl and benzofuran-7-yl.

"Isobenzofuranyl" as used herein includes isobenzofuran-1-yl, isobenzofuran-3-yl, isobenzofuran-4-yl, isobenzofuran-5-yl, isobenzofuran-6-yl and isobenzofuran-7-yl.

"Benzothienyl" as used herein includes benzothien-2-yl, benzothien-3-yl, benzothien-4-yl, benzothien-5-yl, benzothien-6-yl and benzothien-7-yl.

"Isobenzothienyl" as used herein includes isobenzothien-1-yl, isobenzothien-3-yl, isobenzothien-4-yl, isobenzothien-5-yl, isobenzothien-6-yl and isobenzothien-7-yl.

"Indazolyl" as used herein includes indazol-1-yl, indazol-3-yl, indazol-4-yl, indazol-5-yl, indazol-6-yl and indazol-7-yl.

"Benzimidazolyl" as used herein includes benzimidazol-1-yl, benzimidazol-2-yl, benzimidazol-4-yl, benzimidazol-5-yl, benzimidazol-6-yl and benzimidazol-7-yl.

"1,3-Benzoxazolyl" as used herein includes 1,3-benzoxazol-2-yl, 1,3-benzoxazol-4-yl, 1,3-benzoxazol-5-yl, 1,3-benzoxazol-6-yl and 1,3-benzoxazol-7-yl.

"1,2-Benzisoxazolyl" as used herein includes 1,2-benzisoxazol-3-yl, 1,2-benzisoxazol-4-yl, 1,2-benzisoxazol-5-yl, 1,2-benzisoxazol-6-yl and 1,2-benzisoxazol-7-yl.

"2,1-Benzisoxazolyl" as used herein includes 2,1-benzisoxazol-3-yl, 2,1-benzisoxazol-4-yl, 2,1-benzisoxazol-5-yl, 2,1-benzisoxazol-6-yl and 2,1-benzisoxazol-7-yl.

"1,3-Benzothiazolyl" as used herein includes 1,3-benzothiazol-2-yl, 1,3-benzothiazol-4-yl, 1,3-benzothiazol-5-yl, 1,3-benzothiazol-6-yl and 1,3-benzothiazol-7-yl.

"1,2-Benzoisothiazolyl" as used herein includes 1,2-benzisothiazol-3-yl, 1,2-benzisothiazol-4-yl, 1,2-benzisothiazol-5-yl, 1,2-benzisothiazol-6-yl and 1,2-benzisothiazol-7-yl.

"2,1-Benzoisothiazolyl" as used herein includes 2,1-benzisothiazol-3-yl, 2,1-benzisothiazol-4-yl, 2,1-benzisothiazol-5-yl, 2,1-benzisothiazol-6-yl and 2,1-benzisothiazol-7-yl.

"Benzotriazolyl" as used herein includes benzotriazol-1-yl, benzotriazol-4-yl, benzotriazol-5-yl, benzotriazol-6-yl and benzotriazol-7-yl.

"1,2,3-Benzoxadiazolyl" as used herein includes 1,2,3-benzoxadiazol-4-yl, 1,2,3-benzoxadiazol-5-yl, 1,2,3-benzoxadiazol-6-yl and 1,2,3-benzoxadiazol-7-yl.

"2,1,3-Benzoxadiazolyl" as used herein includes 2,1,3-benzoxadiazol-4-yl, 2,1,3-benzoxadiazol-5-yl, 2,1,3-benzoxadiazol-6-yl and 2,1,3-benzoxadiazol-7-yl.

"1,2,3-Benzothiadiazolyl" as used herein includes 1,2,3-benzothiadiazol-4-yl, 1,2,3-benzothiadiazol-5-yl, 1,2,3-benzothiadiazol-6-yl and 1,2,3-benzothiadiazol-7-yl.

"2,1,3-Benzothiadiazolyl" as used herein includes 2,1,3-benzothiadiazol-4-yl, 2,1,3-benzothiadiazol-5-yl, 2,1,3-benzothiadiazol-6-yl and 2,1,3-benzothiadiazol-7-yl.

"Thienopyridinyl" as used herein includes thieno[2,3-b]pyridinyl, thieno[2,3-c]pyridinyl, thieno[3,2-c]pyridinyl and thieno[3,2-b]pyridinyl.

"Purinyl" as used herein includes purin-2-yl, purin-6-yl, purin-7-yl and purin-8-yl.

"Imidazo[1,2-a]pyridinyl" as used herein includes imidazo[1,2-a]pyridin-2-yl, imidazo[1,2-a]pyridin-3-yl, imidazo[1,2-a]pyridin-4-yl, imidazo[1,2-a]pyridin-5-yl, imidazo[1,2-a]pyridin-6-yl and imidazo[1,2-a]pyridin-7-yl.

"Quinolinyl" as used herein includes quinolin-2-yl, quinolin-3-yl, quinolin-4-yl, quinolin-5-yl, quinolin-6-yl, quinolin-7-yl and quinolin-8-yl.

"Isoquinolinyl" as used herein includes isoquinolin-1-yl, isoquinolin-3-yl, isoquinolin-4-yl, isoquinolin-5-yl, isoquinolin-6-yl, isoquinolin-7-yl and isoquinolin-8-yl.

"Cinnolinyl" as used herein includes cinnolin-3-yl, cinnolin-4-yl, cinnolin-5-yl, cinnolin-6-yl, cinnolin-7-yl and cinnolin-8-yl.

"Quinazolinyl" as used herein includes quinazolin-2-yl, quinazolin-4-yl, quinazolin-5-yl, quinazolin-6-yl, quinazolin-7-yl and quinazolin-8-yl.

"1,4-Naphthyridyl" as used herein includes 1,4-naphthyrid-2-yl, 1,4-naphthyrid-3-yl, 1,4-naphthyrid-5-yl, 1,4-naphthyrid-6-yl, 1,4-naphthyrid-7-yl and 1,4-naphthyrid-8-yl.

"1,5-Naphthyridyl" as used herein includes 1,5-naphthyrid-2-yl, 1,5-naphthyrid-3-yl, 1,5-naphthyrid-4-yl, 1,5-naphthyrid-6-yl, 1,5-naphthyrid-7-yl and 1,5-naphthyrid-8-yl.

"1,6-Naphthyridyl" as used herein includes 1,6-naphthyrid-2-yl, 1,6-naphthyrid-3-yl, 1,6-naphthyrid-4-yl, 1,6-naphthyrid-5-yl, 1,6-naphthyrid-7-yl and 1,6-naphthyrid-8-yl.

"1,7-Naphthyridyl" as used herein includes 1,7-naphthyrid-2-yl, 1,7-naphthyrid-3-yl, 1,7-naphthyrid-4-yl, 1,7-naphthyrid-5-yl, 1,7-naphthyrid-6-yl and 1,7-naphthyrid-8-yl.

"1,8-Naphthyridyl" as used herein includes 1,8-naphthyrid-2-yl, 1,8-naphthyrid-3-yl, 1,8-naphthyrid-4-yl, 1,8-naphthyrid-5-yl, 1,8-naphthyrid-6-yl and 1,8-naphthyrid-7-yl.

In the present specification the term "pharmaceutically acceptable salt" of a compound of formula (I) takes its ordinary meaning and includes any acid addition salt of a compound of formula (I), including salts formed with inorganic acids (for example hydrochloric, hydrobromic, nitric, sulphuric or phosphoric acid) or with organic acids, such as organic carboxylic acids (for example fumaric, pyruvic, lactobionic, glycolic, oxalic, maleic, hydroxymaleic, malic, citric, succinic, salicylic, o-acetoxybenzoic or tartaric acid), or organic sulphonic acids (for example toluene-p-sulphonic, bisethanesulphonic or methanesulphonic acid). The dihydrochloride, fumarate, succinate and tartrate salts are preferred. The L-tartrate salt is most preferred.

In the present specification the term "treatment of the human or animal body by therapy" includes both curative and prophylactic therapeutic treatment.

In the above definitions, similar terms specifying different numbers of C atoms take an analogous meaning.

In a preferred embodiment of the present invention, A is

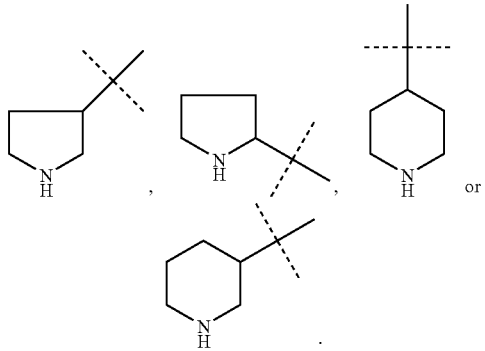

More preferably, A is

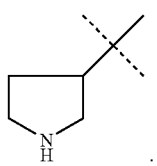

In a preferred embodiment of the present invention, R1 is $C_2$-$C_{10}$alkyl, $C_2$-$C_{10}$alkenyl, $C_3$-$C_8$cycloalkyl, $C_4$-$C_8$cycloalkenyl, $C_4$-$C_{10}$cycloalkylalkyl, $C_5$-$C_{10}$cycloalkenylalkyl, 8-oxabicyclo[3.2.1]oct-6endo-yl or —$(CH_2)_p$-Ph wherein p is 0, 1 or 2 wherein one —$CH_2$— within any cycloalkyl group is optionally substituted by —O— or —S— and wherein each group is optionally substituted with from 1 to 7 halogen substituents and/or with from 1 to 3 substituents each independently selected from hydroxy, cyano, $C_1$-$C_4$alkyl, —S—($C_1$-$C_4$alkyl) (optionally substituted with from 1 to 3 halogen atoms) and —O—($C_1$-$C_4$alkyl) (optionally substituted with from 1 to 3 halogen atoms). More preferably, R1 is $C_2$-$C_{10}$alkyl, $C_3$-$C_8$cycloalkyl, $C_4$-$C_{10}$cycloalkylalkyl, 8-oxabicyclo[3.2.1]oct-6endo-yl or benzyl wherein one —$CH_2$— within any cycloalkyl group is optionally substituted by —O—. Still more preferably, R1 is ethyl, propyl, isopropyl, isobutyl, 2,2-dimethylpropyl, cyclopentyl, cyclohexyl, cyclopropylmethyl, tetrahydrofuran-3-yl, tetrahydropyran-4-yl, 8-oxabicyclo[3.2.1]oct-6endo-yl or benzyl.

In a preferred embodiment of the present invention, R7 is H.

In a preferred embodiment of the present invention, y is 1.

In a preferred embodiment of the present invention, $Ar_1$ is

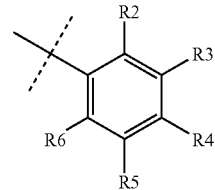

wherein

R2 is H, halogen, cyano, $C_1$-$C_4$alkyl (optionally substituted with from 1 to 7 halogen atoms), —O—($C_1$-$C_4$alkyl) (optionally substituted with from 1 to 7 halogen atoms), —$S(O)_q$—$C_1$-$C_4$alkyl wherein q is 0, 1 or 2 (optionally substituted with from 1 to 7 halogen atoms), phenyl (optionally substituted with from 1 to 3 substituents each independently selected from halogen, $C_1$-$C_4$alkyl or —O—($C_1$-$C_4$alkyl)), phenoxy (optionally substituted with from 1 to 3 substituents each independently selected from halogen, $C_1$-$C_4$alkyl or —O—($C_1$-$C_4$alkyl)) or —$CO_2$($C_1$-$C_4$alkyl), or together with R3 forms a further benzene ring (optionally substituted with from 1 to 3 substituents each independently selected from halogen, $C_1$-$C_4$alkyl and —O—($C_1$-$C_4$alkyl));

R3 is H, halogen, cyano, $C_1$-$C_4$alkyl (optionally substituted with from 1 to 7 halogen atoms), —O—($C_1$-$C_4$alkyl) (optionally substituted with from 1 to 7 halogen atoms), —$S(O)_q$—$C_1$-$C_4$alkyl (optionally substituted with from 1 to 7 halogen atoms), phenyl (optionally substituted with from 1 to 3 substituents each independently selected from halogen, $C_1$-$C_4$alkyl or —O—($C_1$-$C_4$alkyl)), phenoxy (optionally substituted with from 1 to 3 substituents each independently selected from halogen, $C_1$-$C_4$alkyl or —O—($C_1$-$C_4$alkyl)) or —$CO_2$($C_1$-$C_4$alkyl), or together with R2 or R4 forms a further benzene ring (optionally substituted with from 1 to 3 substituents each independently selected from halogen, $C_1$-$C_4$alkyl and —O—($C_1$-$C_4$alkyl));

R4 is H, halogen, cyano, $C_1$-$C_4$alkyl (optionally substituted with from 1 to 7 halogen atoms), —O—($C_1$-$C_4$alkyl) (optionally substituted with from 1 to 7 halogen atoms), —$S(O)_q$—$C_1$-$C_4$alkyl (optionally substituted with from 1 to 7 halogen atoms), phenyl (optionally substituted with from 1 to 3 substituents each independently selected from halogen, $C_1$-$C_4$alkyl or —O—($C_1$-$C_4$alkyl)), phenoxy (optionally substituted with from 1 to 3 substituents each independently selected from halogen, $C_1$-$C_4$alkyl or —O—($C_1$-$C_4$alkyl)) or —CO$_2$($C_1$-$C_4$alkyl), or together with R3 forms a further benzene ring (optionally substituted with from 1 to 3 substituents each independently selected from halogen, $C_1$-$C_4$alkyl and —O—($C_1$-$C_4$alkyl));

R5 is H, $C_1$-$C_4$alkyl (optionally substituted with from 1 to 7 halogen atoms), —O—($C_1$-$C_4$alkyl) (optionally substituted with from 1 to 7 halogen atoms) or halogen; and R6 is H, $C_1$-$C_4$alkyl (optionally substituted with from 1 to 7 halogen atoms), —O—($C_1$-$C_4$alkyl) (optionally substituted with from 1 to 7 halogen atoms) or halogen.

More preferably, R2 is H, halogen, $C_1$-$C_4$alkyl (optionally substituted with from 1 to 3 halogen atoms), —O—($C_1$-$C_4$alkyl) (optionally substituted with from 1 to 3 halogen atoms) or phenyl.

More preferably, R3 is H, halogen or $C_1$-$C_4$alkyl (optionally substituted with from 1 to 3 halogen atoms).

More preferably, R4 is H, halogen or $C_1$-$C_4$alkyl (optionally substituted with from 1 to 3 halogen atoms).

More preferably, R5 is H, $C_1$-$C_4$alkyl (optionally substituted with from 1 to 3 halogen atoms).

More preferably, R6 is H.

More preferably, at least three of R2 to R6 are H.

Most preferably, the group

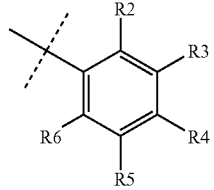

is phenyl, 2-chlorophenyl, 2-(trifluoromethyl)phenyl, 2-(difluoromethoxy)phenyl, 2-biphenyl, 3-chlorophenyl, 4-chlorophenyl, 2,3-dichlorophenyl, 2,4-dichlorophenyl, 2,4-difluorophenyl, 2-chloro-4-fluorophenyl, 2,5-dichlorophenyl, 3,4-dichlorophenyl, 3,5-dichlorophenyl, 3,5-bis(trifluoromethyl)phenyl, 4-fluoro-2-(trifluoromethyl)phenyl or 4-chloro-2-ethoxyphenyl.

A further preferred embodiment of the present invention provides a compound of formula (IA)

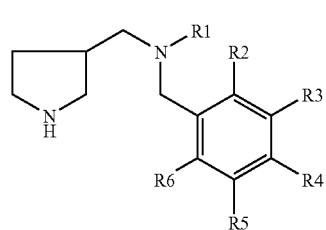

(IA)

wherein

R1 is $C_2$-$C_{10}$alkyl, $C_2$-$C_{10}$alkenyl, $C_3$-$C_8$cycloalkyl, $C_4$-$C_8$cycloalkenyl, $C_4$-$C_{10}$cycloalkylalkyl, $C_5$-$C_{10}$cycloalkenylalkyl, 8-oxabicyclo[3.2.1]oct-6endo-yl or —(CH$_2$)$_p$—Ph wherein p is 0, 1 or 2 wherein one —CH$_2$— within any cycloalkyl group is optionally substituted by —O— or —S— and wherein each group is optionally substituted with from 1 to 7 halogen substituents and/or with from 1 to 3 substituents each independently selected from hydroxy, cyano, $C_1$-$C_4$alkyl, —S—($C_1$-$C_4$alkyl) (optionally substituted with from 1 to 3 halogen atoms) and —O—($C_1$-$C_4$alkyl) (optionally substituted with from 1 to 3 halogen atoms).

R2 is H, halogen, cyano, $C_1$-$C_4$alkyl (optionally substituted with from 1 to 7 halogen atoms), —O—($C_1$-$C_4$alkyl) (optionally substituted with from 1 to 7 halogen atoms), —S(O)$_q$—$C_1$-$C_4$alkyl wherein q is 0, 1 or 2 (optionally substituted with from 1 to 7 halogen atoms), phenyl (optionally substituted with from 1 to 3 substituents each independently selected from halogen, $C_1$-$C_4$alkyl or —O—($C_1$-$C_4$alkyl)), phenoxy (optionally substituted with from 1 to 3 substituents each independently selected from halogen, $C_1$-$C_4$alkyl or —O—($C_1$-$C_4$alkyl)) or —CO$_2$($C_1$-$C_4$alkyl), or together with R3 forms a further benzene ring (optionally substituted with from 1 to 3 substituents each independently selected from halogen, $C_1$-$C_4$alkyl and —O—($C_1$-$C_4$alkyl));

R3 is H, halogen, cyano, $C_1$-$C_4$alkyl (optionally substituted with from 1 to 7 halogen atoms), —O—($C_1$-$C_4$alkyl) (optionally substituted with from 1 to 7 halogen atoms), —S(O)$_q$—$C_1$-$C_4$alkyl (optionally substituted with from 1 to 7 halogen atoms), phenyl (optionally substituted with from 1 to 3 substituents each independently selected from halogen, $C_1$-$C_4$alkyl or —O—($C_1$-$C_4$alkyl)), phenoxy (optionally substituted with from 1 to 3 substituents each independently selected from halogen, $C_1$-$C_4$alkyl or —O—($C_1$-$C_4$alkyl)) or —CO$_2$($C_1$-$C_4$alkyl), or together with R2 or R4 forms a further benzene ring (optionally substituted with from 1 to 3 substituents each independently selected from halogen, $C_1$-$C_4$alkyl and —O—($C_1$-$C_4$alkyl));

R4 is H, halogen, cyano, $C_1$-$C_4$alkyl (optionally substituted with from 1 to 7 halogen atoms), —O—($C_1$-$C_4$alkyl) (optionally substituted with from 1 to 7 halogen atoms), —S(O)$_q$—$C_1$-$C_4$alkyl (optionally substituted with from 1 to 7 halogen atoms), phenyl (optionally substituted with from 1 to 3 substituents each independently selected from halogen, $C_1$-$C_4$alkyl or —O—($C_1$-$C_4$alkyl)), phenoxy (optionally substituted with from 1 to 3 substituents each independently selected from halogen, $C_1$-$C_4$alkyl or —O—($C_1$-$C_4$alkyl)) or —CO$_2$($C_1$-$C_4$alkyl), or together with R3 forms a further benzene ring (optionally substituted with from 1 to 3 substituents each independently selected from halogen, $C_1$-$C_4$alkyl and —O—($C_1$-$C_4$alkyl));

R5 is H, $C_1$-$C_4$alkyl (optionally substituted with from 1 to 7 halogen atoms), —O—($C_1$-$C_4$alkyl) (optionally substituted with from 1 to 7 halogen atoms) or halogen; and R6 is H, $C_1$-$C_4$alkyl (optionally substituted with from 1 to 7 halogen atoms), —O—($C_1$-$C_4$alkyl) (optionally substituted with from 1 to 7 halogen atoms) or halogen;

or pharmaceutically acceptable salt thereof.

A further preferred embodiment of the present invention provides a compound of formula (IA) above wherein, R1 is $C_2$-$C_{10}$alkyl, $C_3$-$C_8$cycloalkyl, $C_4$-$C_{10}$cycloalkylalkyl, 8-oxabicyclo[3.2.1]oct-6endo-yl or benzyl wherein one —CH$_2$— within any cycloalkyl group is optionally substituted by —O—;

R2 is H, halogen, $C_1$-$C_4$alkyl (optionally substituted with from 1 to 3 halogen atoms), —O—($C_1$-$C_4$alkyl) (optionally substituted with from 1 to 3 halogen atoms) or phenyl;

R3 is H, halogen or $C_1$-$C_4$alkyl (optionally substituted with from 1 to 3 halogen atoms);

R4 is H, halogen or $C_1$-$C_4$alkyl (optionally substituted with from 1 to 3 halogen atoms);
R5 is H, halogen or $C_1$-$C_4$alkyl (optionally substituted with from 1 to 3 halogen atoms); and
R6 is H;
or pharmaceutically acceptable salt thereof.

A further preferred embodiment of the present invention provides a compound selected from the group consisting of:
N-{[2,4-Dichlorophenyl]methyl}-N-(tetrahydro-2H-pyran-4-yl)-(3S)-pyrrolidine-3-yl-methylamine,
N-{[3,5-Dichlorophenyl]methyl}-N-(tetrahydro-2H-pyran-4-yl)-(3S)-pyrrolidine-3-yl-methylamine,
N-(2-Methylpropyl)-N-{[2-(trifluoromethyl)phenyl]methyl}-(3R)-pyrrolidine-3-yl-methylamine,
N-(2-Methylpropyl)-N-{[2,4-dichlorophenyl]methyl}-(3R)-pyrrolidine-3-yl-methylamine,
N-(2-Methylpropyl)-N-{[3,5-dichlorophenyl]methyl}-(3R)-pyrrolidine-3-yl-methylamine,
N-{[2,4-Dichlorophenyl]methyl}-N-(tetrahydro-2H-pyran-4-yl)-(3R)-pyrrolidine-3-yl-methylamine,
N-{[3,5-Dichlorophenyl]methyl}-N-(tetrahydro-2H-pyran-4-yl)-(3R)-pyrrolidine-3-yl-methylamine,
N-(2-Methylpropyl)-N-{[2-(trifluoromethyl)phenyl]methyl}-(3S)-pyrrolidine-3-yl-methylamine,
N-(2-Methylpropyl)-N-{(2,4-dichlorophenyl)methyl}-(3S)-pyrrolidine-3-yl-methylamine,
N-(2-Methylpropyl)-N-{(3,5-dichlorophenyl)methyl}-(3S)-pyrrolidine-3-yl-methylamine,
N-(1-Methylethyl)-N-{(2,4-dichlorophenyl)methyl}-(3S)-pyrrolidine-3-yl-methylamine,
N-Propyl-N-{(2,4-dichlorophenyl)methyl}-(3S)-pyrrolidine-3-yl-methylamine,
N-(Cyclopentyl)-N-{(2,4-dichlorophenyl)methyl}-(3S)-pyrrolidine-3-yl-methylamine,
N-(Cyclopropylmethyl)-N-{(2,4-dichlorophenyl)methyl}-(3S)-pyrrolidine-3-yl-methylamine,
N-(1-Methylethyl)-N-{(3,5-dichlorophenyl)methyl}-(3R)-pyrrolidine-3-yl-methylamine,
N-Propyl-N-{(3,5-dichlorophenyl)methyl}-(3R)-pyrrolidine-3-yl-methylamine,
N-(Cyclopentyl)-N-{(3,5-dichlorophenyl)methyl}-(3R)-pyrrolidine-3-yl-methylamine,
N-(Cyclopropylmethyl)-N-{(3,5-dichlorophenyl)methyl}-(3R)-pyrrolidine-3-yl-methylamine,
N-(2-Methylpropyl)-N-{[3,5-bis(trifluoromethyl)phenyl]methyl}-(3S)-pyrrolidine-3-yl-methylamine,
N-(Phenylmethyl)-N-{(2,4-dichlorophenyl)methyl}-(3S)-pyrrolidine-3-ylmethylamine,
N-(Phenylmethyl)-N-{(3,5-dichlorophenyl)methyl}-(3R)-pyrrolidine-3-yl-methylamine,
N-(2-Methylpropyl)-N-{(2,3-dichlorophenyl)methyl}-(3S)-pyrrolidine-3-yl-methylamine,
N-(2-Methylpropyl)-N-{(3,4-dichlorophenyl)methyl}-(3S)-pyrrolidine-3-yl-methylamine,
N-(2-Methylpropyl)-N-{[4-fluoro-2-(trifluoromethyl)phenyl]methyl}-(3S)-pyrrolidine-3-yl-methylamine,
N-(2-Methylpropyl)-N-{(2-chloro-4-fluorophenyl)methyl}-(3S)-pyrrolidine-3-yl-methylamine,
N-(2-Methylpropyl)-N-{(2,4-difluorophenyl)methyl}-(3S)-pyrrolidine-3-yl-methylamine,
N-(2-Methylpropyl)-N-{[(1,1-biphenyl)-2ylmethyl}-(3S)-pyrrolidine-3-yl-methylamine,
N-(2-Methylpropyl)-N-{[(1,1-biphenyl)-2ylmethyl}-(3R)-pyrrolidine-3-yl-methylamine,
N-(1-Ethyl)-N-{(3,5-dichlorophenyl)methyl}-(3R)-pyrrolidine-3-yl-methylamine,
N-(2-2-Dimethylpropyl)-N-{(2,4-dichlorophenyl)methyl}-(3S)-pyrrolidine-3-yl-methylamine,
N-(Cyclopropylmethyl)-N-{(3,5-dichloro-phenyl)methyl}-(3S)-pyrrolidine-3-ylmethylamine,
N-(Cyclohexyl)-N-{(2,4-dichlorophenyl)methyl}-(3S)-pyrrolidine-3-ylmethylamine,
N-(2-Methylpropyl)-N-{(2-chlorophenyl)methyl}-(3R)-pyrrolidine-3-ylmethylamine,
N-(2-Methylpropyl)-N-{(3-chlorophenyl)methyl}-(3R)-pyrrolidine-3-ylmethylamine,
N-(2-Methylpropyl)-N-{(4-chlorophenyl)methyl}-(3R)-pyrrolidine-3-ylmethylamine,
N-(2-Methylpropyl)-N-{(2,5-dichlorophenyl)methyl}-(3R)-pyrrolidine-3 -ylmethylamine,
N-(2-Methylpropyl)-N-{(2-chlorophenyl)methyl}-(3S)-pyrrolidine-3-ylmethylamine,
N-(2-Methylpropyl)-N-{(3-chlorophenyl)methyl}-(3S)-pyrrolidine-3-ylmethylamine,
N-(2-Methylpropyl)-N-{(4-chlorophenyl)methyl}-(3S)-pyrrolidine-3-ylmethylamine,
N-(2-Methylpropyl)-N-{(2,5-dichlorophenyl)methyl}-(3S)-pyrrolidine-3-ylmethylamine,
N-(2-Methylpropyl)-N-(benzyl)-(3S)-pyrrolidine-3-ylmethylamine,
N-Ethyl-N-{(2,4-dichlorophenyl)methyl}-(3S)-pyrrolidine-3-ylmethylamine,
N-(Cyclopentyl)-N-{(2,4-dichlorophenyl)methyl}-(3R)-pyrrolidine-3-ylmethylamine,
N-(2-Methylpropyl)-N-{(4-chloro-2-ethoxyphenyl)methyl}-(3S)-pyrrolidine-3-ylmethylamine,
N-(2-Methylpropyl)-N-{[2-(difluoromethoxy)phenyl]methyl}-(3S)-pyrrolidine-3-ylmethylamine,
N-(2-Methylpropyl)-N-{[2-(difluoromethoxy)phenyl]methyl}-(3R)-pyrrolidine-3-ylmethylamine,
N-{[2,4-Dichlorophenyl]methyl}-N-(tetrahydrofuran-3S-yl)-(3S)-pyrrolidine-3-yl-methylamine,
N-{[3,5-Dichlorophenyl]methyl}-N-(tetrahydrofuran-3S-yl)-(3S)-pyrrolidine-3-yl-methylamine,
N-{[2,4-Dichlorophenyl]methyl}-N-(tetrahydrofuran-3R-yl)-(3S)-pyrrolidine-3-yl-methylamine,
N-{[3,5-Dichlorophenyl]methyl}-N-(tetrahydrofuran-3R-yl)-(3S)-pyrrolidine-3-yl-methylamine,
(3-endo)-N-(2,4-dichlorobenzyl)-N-[(3S)-pyrrolidin-3-ylmethyl]-8-oxabicyclo[3.2.1]octan-3-amine,
N-{[2,4-Dichlorophenyl]methyl}-N-(tetrahydrofuran-3S-yl)-(3R)-pyrrolidine-3-yl-methylamine,
N-{[3,5-Dichlorophenyl]methyl}-N-(tetrahydrofuran-3S-yl)-(3R)-pyrrolidine-3-yl-methylamine,
N-{[2,4-Dichlorophenyl]methyl}-N-(tetrahydrofuran-3R-yl)-(3R)-pyrrolidine-3-yl-methylamine,
N-{[3,5-Dichlorophenyl]methyl}-N-(tetrahydrofuran-3R-yl)-(3R)-pyrrolidine-3-yl-methylamine,
(3-endo)-N-(2,4-dichlorobenzyl)-N-[(3R)-pyrrolidin-3-yl-methyl]-8-oxabicyclo[3.2.1]octan-3-amine,
N-(2-Methylpropyl)-N-{[3,5-dichlorophenyl]-methyl}-(2S)-pyrrolidine-2-yl-methylamine,
N-(2-Methylpropyl)-N-{[3,5-dichlorophenyl]-methyl}-(3R)-piperidine-3-yl-methylamine,
N-(2-Methylpropyl)-N-{[2-chlorophenyl]-methyl}-piperidine-4-yl-methylamine, and
N-(3-Hydroxy-3-methylbutyl)-N-{[2,4-dichlorophenyl]-methyl}-azetidine-3-yl-methylamine,
or pharmaceutically acceptable salt thereof.

It will be appreciated that certain compounds of formula I may possess one or more chiral centres. Where a structural formula does not specify the stereochemistry at one or more chiral centres, it encompasses all possible stereoisomers and all possible mixtures of stereoisomers (including, but not limited to, racemic mixtures) which may result from stereoisomerism at each of the one or more chiral centers.

As mentioned above, the compounds of the present invention and their pharmaceutically acceptable salts inhibit the uptake of one or more of the monoamine neurotransmitters serotonin, dopamine and norepinephrine.

In view of these properties, the compounds of the present invention and their pharmaceutically acceptable salts are indicated for use in treating disorders which are caused by or linked to decreased neurotransmission of one or more of these monoamines.

One preferred group of compounds of the present invention selectively inhibit the reuptake of serotonin and norepinephrine over dopamine. Preferably said group of compounds of the present invention selectively inhibit the serotonin and norepinephrine transporters relative to the dopamine transporter by a factor of at least five, and even more preferably by a factor of at least ten. Compounds of the present invention with this pharmacological profile are particularly useful for the treatment of depression, eating disorders (including bulimia and anorexia nervosa), inflammatory bowel disorders, functional bowel disorders, dyspepsia, Crohn's disease, iletis, ischemic bowel disease, ulcerative colitis, gastroesophageal reflux for functional bowel disorders, irritable bowel syndrome, obesity, insterstitial cystitis, urethral syndrome, gastric motility disorders, substance abuse (including alcoholism, tobacco abuse, symptoms caused by withdrawal or partial withdrawal from the use of tobacco or nicotine and drug addiction including cocaine abuse), pain (including inflammatory pain, neuropathic pain, non-neuropathic non-inflammatory pain, persistent pain, persistent pain of inflammatory and/or neuropathic origin, headache and migraine), incontinence (including stress urinary incontinence and urge incontinence), dementia of aging, senile dementia, Alzheimer's, memory loss, Parkinsonism, attention-deficit disorder (including attention-deficit hyperactivity disorder), anxiety, social phobia, disruptive behavior disorders, impulsive control disorders, borderline personality disorder, chronic fatigue syndrome, panic disorders, obsessive compulsive disorder, post-traumatic stress disorder, schizophrenia, gastrointestinal disorders, cardiovascular disorders, hot flushes/flashes, emesis, sleep disorders, cognitive disorders, psychotic disorders, brain trauma, premenstrual syndrome or late luteal syndrome, sexual dysfunction (including premature ejaculation and erectile difficulty), autism, mutism and trichotilomania. They are more particularly useful for the treatment of depression, incontinence (particularly stress urinary incontinence) and pain (particularly persistent pain). They are most particularly useful for the treatment of persistent pain.

For clinical purposes, pain may be divided into two categories: acute pain and persistent pain. Acute pain is provoked by noxious stimulation produced by injury and/or disease of skin, deep somatic structures or viscera, or abnormal function of muscle or viscera that does not produce actual tissue damage. On the other hand, persistent pain can be defined as pain that persists beyond the usual course of an acute disease or a reasonable time for an injury to heal or that is associated with a chronic pathologic process that causes continuous pain or the pain recurs at intervals for months or years. If pain is still present after a cure should have been achieved, it is considered persistent pain. For the purpose of the present invention, persistent pain can be chronic non-remitting or recurrent. The difference in definition between acute and persistent pain is not merely semantic but has an important clinical relevance. For example, a simple fracture of the wrist usually remains painful for a week to 10 days. If the pain is still present beyond the typical course of treatment, it is likely that the patient is developing reflex sympathetic dystrophy, a persistent pain syndrome that requires immediate effective therapy. Early and effective intervention potentially prevents the undue disability and suffering, and avoids the potential development of a condition that becomes refractory to therapy.

Acute and persistent pain differ in etiology, mechanisms, pathophysiology, symptomatology, diagnosis, therapy, and physiological responses. In contrast to the transitory nature of acute pain, persistent pain is caused by chronic pathologic processes in somatic structures or viscera, by prolonged and sometimes permanent dysfunction of the peripheral or central nervous system, or both. Also, persistent pain can sometimes be attributed to psychologic mechanisms and/or environmental factors.

More specifically, persistent pain can be segmented into neuropathic pain (e.g. diabetic neuropathy, infectious neuropathic pain associated with AIDS, non-surgical carpal tunnel syndromes, post-herpetic neuralgia, cervical, thoracic and lumbosacral radiculopathies, stroke-related central pains, trigeminal neuralgia and complex regional pain syndromes I and II), inflammatory pain (e.g. polymyalgia, rheumatoid arthritis and osteoarthritis), and non-neuropathic non-inflammatory chronic pain (NNNICP) (e.g. chronic fatigue syndrome, chronic back pain without radiculopathy, fibromyalgia, chronic tension type headaches, inflammatory bowel disorders, irritable bowel syndrome, whiplash injuries, chronic pelvic pain, temporomandibular joint disorder (TMJD) and failed back).

Current therapies for persistent pain include opiates, barbiturate-like drugs such as thiopental sodium and surgical procedures such as neurectomy, rhizotomy, cordotomy, and cordectomy.

Another preferred group of compounds of the present invention selectively inhibit the reuptake of serotonin over norepinephrine and dopamine. Preferably said group of compounds of the present invention selectively inhibit the serotonin transporter relative to the norepinephrine and dopamine transporters by a factor of at least five, and even more preferably by a factor of at least ten. Compounds of the present invention with this pharmacological profile are particularly useful for the treatment of depression.

Another preferred group of compounds of the present invention selectively inhibit the reuptake of norepinephrine over serotonin and dopamine. Preferably said group of compounds of the present invention selectively inhibit the norepinephrine transporter relative to the serotonin and dopamine transporters by a factor of at least five, and even more preferably by a factor of at least ten. Compounds of the present invention with this pharmacological profile are particularly useful for the treatment of addictive disorder and withdrawal syndrome, an adjustment disorder (including depressed mood, anxiety, mixed anxiety and depressed mood, disturbance of conduct, and mixed disturbance of conduct and mood), an age-associated learning and mental disorder (including Alzheimer's disease), alcohol addiction, allergies (in particular allergic rhinitis), anorexia nervosa, apathy, asthma, an attention-deficit disorder (ADD) due to general medical conditions, attention-deficit hyperactivity disorder (ADHD) (optionally by combination therapy with stimulants (e.g. methylphenidate, amphetamine and dextroamphetamine)) including the predominantly inattentive type of ADHD and the predominantly hyperactive-impulsive type of ADHD, bipolar disorder, bulimia nervosa, chronic fatigue syndrome, chronic or acute stress, cognitive disorders (discussed in more detail below but including mild cognitive impairment (MCI) and cognitive impairment associated with schizophrenia (CIAS)), communication disorders (including stuttering, expressive language disorder, mixed receptive-expressive language disorder, phonological disorder and communication disorder not otherwise specified), conduct disorder, cyclothymic disorder, dementia of the Alzheimers type (DAT), depression (including adolescent depression and minor depression), dysthymic disorder, emotional dysregulation (including emotional dysregulation associated with ADHD, borderline personality disorder, bipolar disorder, schizophrenia, schizoaffective disorder and intermittent explosive disorder), fibromyalgia and other somatoform disorders (including somatization disorder, conversion disorder, pain disorder, hypochondriasis, body dysmorphic disorder, undifferentiated somatoform disorder, and somatoform NOS), generalized anxiety disorder, hot flashes or vasomotor symptoms, hypotensive states including orthostatic hypotension, impulse control disorders (including intermittent explosive disorder, kleptomania, pyromania, pathological gambling, trichotillomania and impulse-control disorder not otherwise specified), incontinence (i.e., stress incontinence, genuine stress incontinence, mixed incontinence and bedwetting), an inhalation disorder, an intoxication disorder, learning disabilities (including developmental speech and language disorders (such as developmental articulation disorder, developmental expressive language disorder and developmental receptive language disorder), learning disorders (such as reading disorder, mathematics disorder, disorder of written expression and learning disorder not otherwise specified) and motor skills disorders (such as developmental coordination disorder)), mania, migraine headaches, neuropathic pain, nicotine addiction, obesity (i.e., reducing the weight of obese or overweight patients), obsessive compulsive disorders and related spectrum disorders, oppositional defiant disorder, pain including chronic pain, neuropathic pain and antinociceptive pain, panic disorder, Parkinson's disease (in particular to improve dyskinesia, oscillations, balance, coordination, depression, and motivation), peripheral neuropathy, post-traumatic stress disorder, personality change due to a general medical condition (including labile type, disinhibited type, aggressive type, apathetic type, paranoid type, combined type and unspecified type), pervasive developmental disorders (including autistic disorder, Asperger's disorder, Rett's disorder, childhood disintegrative disorder, and pervasive developmental disorder not otherwise specified), premenstrual dysphoric disorder (i.e., premenstrual syndrome and late luteal phase dysphoric disorder), psoriasis, psychoactive substance use disorders, a psychotic disorder (including schizophrenia, schizoaffective and schizophreniform disorders), restless legs syndrome, seasonal affective disorder, a sleep disorder (such as narcolepsy and enuresis), sexual dysfunction, social phobia (including social anxiety disorder), a specific developmental disorder, selective serotonin reuptake inhibition (SSRI) "poop out" syndrome (i.e., wherein a patient who fails to maintain a satisfactory response to SSRI therapy after an initial period of satisfactory response), TIC disorders (e.g., Tourette's Disease), tobacco addiction and vascular dementia.

The term "cognitive disorders" (also variously referred to as "cognitive failure," "cognitive insufficiency," "cognitive deficit," "cognitive impairment," "cognitive dysfunction," and the like) refers to the dysfunction, diminution, or loss of one or more cognitive functions, the processes by which knowledge is acquired, retained, and used. Cognitive dysfunction includes cognitive changes associated with aging ("age-associated memory impairment"), as well as changes due to other causes. Cognitive impairment is most commonly due to a delirium or dementia, but can also occur in association with a number of other medical or neuropsychiatric disorders. More focal cognitive deficits are diagnosed using the criteria disclosed in the *Diagnostic and Statistical Manual of Mental Disorders*, Fourth Edition, Text Revision (DSM-IV-TR™, 2000), American Psychiatric Association, Washington, D.C., as either amnestic disorders (affecting memory) or cognitive disorder not otherwise specified (NOS), which includes executive dysfunction, visuospatial/visuoconstructional impairment, attentional deficits, disorientation, etc. These more focal cognitive disorders also have a wide variety of causes, some of which are of unknown etiology.

Another preferred group of compounds of the present invention inhibit the reuptake of norepinephrine, serotonin and dopamine. Compounds of the present invention with this pharmacological profile are particularly useful for the treatment of a variety of conditions such as depression, obesity, compulsive disorders (including bulimia, obsessive compulsive disorder, drug addiction including cocaine abuse and alcohol addiction), hypertension, senile dementia, Alzheimer's, memory loss, attention-deficit hyperactivity disorder (ADHD), sexual dysfunction, Parkinsonism, anxiety, chronic fatigue syndrome, panic disorders, cognitive disorders, schizophrenia, gastrointestinal disorders, headache, cardiovascular disorders, epilepsy, smoking cessation, pain including chronic pain, urinary incontinence, emesis and sleep disorders. They are most particularly useful for the treatment of depression, chronic pain, smoking cessation and obesity.

Accordingly, as noted above, the present invention provides a compound of formula (I) or a pharmaceutically acceptable salt thereof for use in therapy. In particular, the present invention provides a compound of formula (I) or a pharmaceutically acceptable salt thereof for use as an inhibitor of the uptake of one or more of the monoamine neurotransmitters serotonin, dopamine and norepinephrine.

As noted above, in another embodiment, the present invention provides a method for inhibiting the uptake of one or more monoamines selected from serotonin, dopamine and norepinephrine in a mammal, comprising administering to a mammal in need of such inhibition an effective amount of a compound of formula (I) or a pharmaceutically acceptable salt thereof. In particular, the present invention provides a method for treating a disorder which is caused by or linked to decreased neurotransmission of one or more monoamines selected from serotonin, dopamine and norepinephrine in a mammal, comprising administering to a mammal in need of such treatment an effective amount of a compound of formula (I) or a pharmaceutically acceptable salt thereof. Such disorders include, for example, disorders of the central and/or peripheral nervous system.

In the context of the present specification the terms "treating" and "treatment" include prophylactic treatment as well as curative treatment.

As noted above, in another alternative embodiment, the present invention provides for the use of a compound of formula (I) or a pharmaceutically acceptable salt thereof for the manufacture of a medicament for inhibiting the uptake of one or more monoamines selected from serotonin, dopamine and norepinephrine. In particular, the present invention provides for the use of a compound of formula (I) or a pharmaceutically acceptable salt thereof for the manufacture of a medicament for the treatment of a disorder which is caused by or linked to decreased neurotransmission of one or more monoamines selected from serotonin, dopamine and norepinephrine. Such disorders include, for example, disorders of the central and/or peripheral nervous system.

The compounds may be administered by various routes and are usually employed in the form of a pharmaceutical composition. Accordingly, as noted above, in a further embodiment, the present invention provides a pharmaceutical composition comprising a compound of formula (I) or a pharmaceutically acceptable salt thereof together with a pharmaceutically acceptable diluent or carrier.

Such compositions may be prepared by methods well known in the pharmaceutical art and normally comprise at least one active compound in association with a pharmaceutically acceptable diluent or carrier. In making the compositions of the present invention, the active ingredient will usually be mixed with a carrier or diluted by a carrier, and/or enclosed within a carrier which may, for example, be in the form of a capsule, sachet, paper or other container.

The compositions indicated can be sterilized and/or can contain auxiliaries such as lubricants, preservatives, stabilizers and/or wetting agents, emulsifiers, salts for affecting the osmotic pressure, buffer substances, colourants, flavourings and/or one or more further active compounds. Compositions of the invention may be formulated so as to provide, quick, sustained or delayed release of the active ingredient after administration to the patient by employing procedures well known in the art.

The compositions are preferably formulated in a unit dosage form, each dosage containing from about 5 to about 500 mg of the active ingredient.

In the context of the present specification, the term "unit dosage form" refers to physically discrete units suitable as unitary doses for human subjects and other mammals, each unit containing a predetermined quantity of one or more compounds of formula (I) or pharmaceutically acceptable salts thereof, calculated to produce the desired therapeutic effect, together with a pharmaceutically acceptable diluent or carrier.

Compounds of formula (I) may be prepared by conventional organic chemistry techniques. In the schemes that follow, y, R1, R7, and $Ar_1$ have the meanings ascribed to them above. Additional notation used is defined in the context of each scheme. It will be noted that in the schemes that follow A is shown as a pyrrolidin-3-yl group. However, compounds wherein A is selected from any of its other possible identities may be synthesized by analogous techniques.

Preparation of the key intermediate of formula (II) is shown in Scheme 1 below.

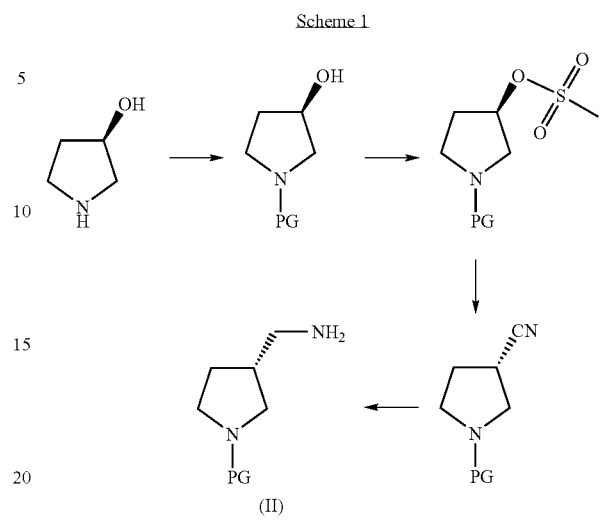

PG means a nitrogen protecting group, suitable examples of which will be well known to those of skill in the art as will methods for their removal. Further information on suitable N-protecting groups is contained in the well known text "Protective Groups in Organic Synthesis", Theodora W. Greene and Peter G. M. Wuts, John Wiley & Sons, Inc., New York, 1999, pp. 494-653. A preferred N-protecting group is the t-butyloxycarbonyl (BOC) group.

Firstly, 3-hydroxypyrrolidine is N-protected using a suitable protecting group. Then the hydroxy group is converted into a good leaving group such as a mesylate by reaction with mesyl chloride in the presence of a non-nucleophilic base such as triethylamine in a suitable solvent such as dichloromethane. Nucleophilic substitution by a nitrile anion followed by reduction using, for example, the conditions described in U.S. Pat. No. 6,180,627 provides a compound of formula (II). The opposite enantiomer may be prepared starting with the appropriate 3-hydroxypyrrolidine.

The intermediate of formula (II) may be converted into compounds of formula (V) by an number of possible routes as shown in Scheme 2 below. For clarity, y is defined as 1 and R7 is defined as H. However, compounds wherein y and R7 are selected from any of their other possible identities may be synthesized by analogous techniques.

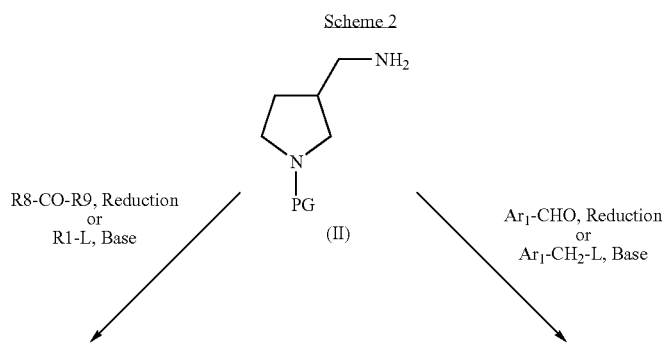

-continued

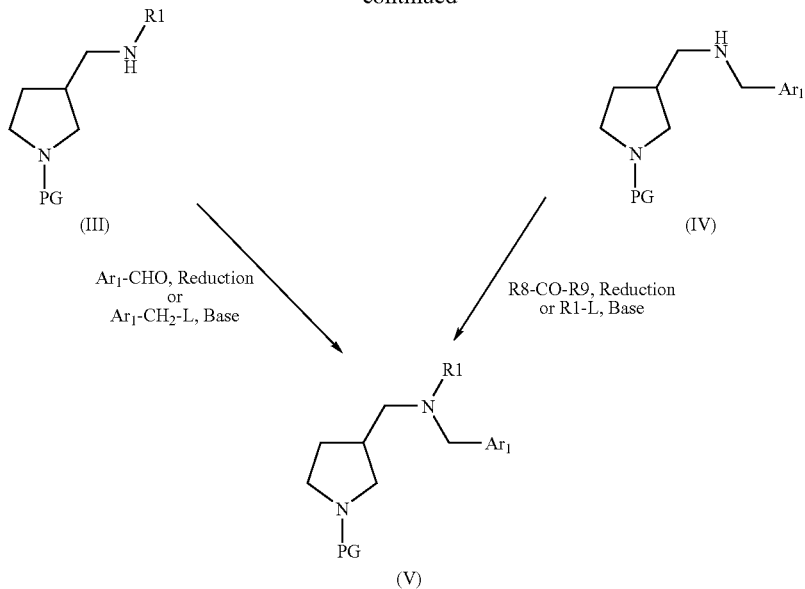

Following the left-hand branch of Scheme 2, compounds of formula (II) may be converted into compounds of formula (III) either by reaction with a carbonyl compound of the formula R8-CO—R9 (where R8 and R9 are chosen such that R8-CH—R9=R1) under reductive conditions (for example sodium borohydride) in a suitable solvent (for example ethanol) or by reaction with a compound of the formula R1-L (where L represents a suitable leaving group such as, for example, tosylate) under basic conditions (for example potassium carbonate) in a suitable solvent (for example acetonitrile).

Compounds of formula (III) may be converted into compounds of formula (V) either by reaction with a carbonyl compound of the formula $Ar_1$-CHO under reductive conditions (for example sodium triacetoxyborohydride) in a suitable solvent (for example dichloroethane, THF or DMSO) or by reaction with a compound of the formula $Ar_1$-$CH_2$-L under basic conditions (for example potassium carbonate) in a suitable solvent (for example acetonitrile).

The right-hand branch of Scheme 2 shows the same procedures described above performed in the opposite order.

Compounds of formula (V) may be converted into compounds of formula (I) by deprotection of the azacyclic nitrogen as shown in Scheme 3 below.

Scheme 3

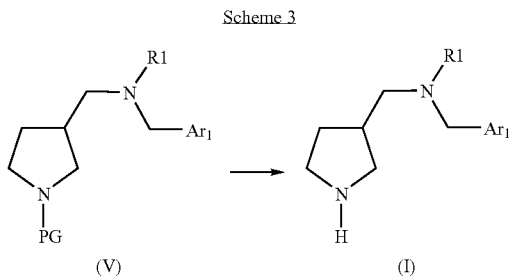

The conditions used for the deprotection step obviously depend upon the protecting group used. For example, where PG is a BOC group, deprotection may be achieved using trifluoroacetic acid in a suitable solvent such as dichloromethane.

The present invention also provides a process for producing a compound of formula (I) above, or a pharmaceutically acceptable salt thereof, which comprises deprotection of a compound of the formula

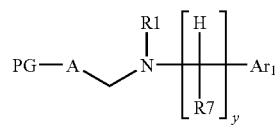

where PG is a N-protecting group and y, A, R1, R7 and $Ar_1$ are as defined for formula (I), optionally followed by formation of a pharmaceutically acceptable salt. Suitable N-protecting groups will be known to the person skilled in the art and include, for example, BOC, benzyl, benzyloxycarbonyl (CBZ) and acetyl.

EXAMPLE 1

N-{[2,4-Dichlorophenyl]methyl}-N-(tetrahydro-2H-pyran-4-yl)-(3S)-pyrrolidine-3-ylmethylamine L-Tartrate

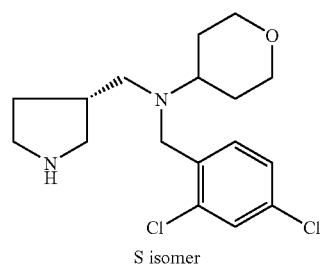

S isomer

Step (i)

N-(Tetrahydro-2H-pyran-4-yl)-1-tert-butyloxycarbonyl-(3R)-pyrrolidine-3-yl-methylamine A solution of (R)-3-(aminomethyl)-1-N-tert-butyloxycarbonylpyrrolidine (0.72 g, 3.60 mmol, commercially available from AstaTech, Inc.) and tetrahydro-4H-pyran-4-one (0.36 g, 3.60 mmol) in ethanol (12 ml) is stirred under an atmosphere of nitrogen at room temperature overnight. Sodium borohydride (0.27 g, 7.20 mmol) is added portionwise and the mixture is stirred for 1.5 h at room temperature. The reaction mixture is concentrated and water is added prior to extraction with diethyl ether. The extract is washed with brine, dried over magnesium sulphate, filtered and evaporated to give the required product as an oil.

Step (ii)

N-{[2,4-Dichlorophenyl]methyl}-N-(tetrahydro-2H-pyran-4-yl)-1-tert-butyloxycarbonyl-(3R)-pyrrolidine-3-yl-methylamine A mixture of N-(tetrahydro-2H-pyran-4-yl)-1-tert-butyloxycarbonyl-(3R)-pyrrolidine-3-yl-methylamine (0.36 g, 1.26 mmol), 2,4-dichlorobenzaldehyde (0.44 g, 2.52 mmol) and sodium triacetoxyborohydride (0.67 g, 3.15 mmol) in 1,2-dichloroethane (15 ml) is stirred at room temperature for 18 h. Water (2 ml) is added to the reaction mixture and stirring continued for 5 min. The organic phase is separated using a hydrophobic frit and evaporated. The resulting oil is dissolved in methanol and purified using a SCX-2 column (10 g), then washed with methanol. The basic product elutes with methanolic ammonia (2M). Evaporation gives the required compound as a colourless oil.

Step (iii)

N-{[2,4-Dichlorophenyl]methyl}-N-(tetrahydro-2H-pyran-4-yl)-(3S)-pyrrolidine-3-yl-methylamine L-Tartrate A solution of (3R)-N-{[2,4-dichlorophenyl]methyl}-N-(tetrahydro-2H-pyran-4-yl)-1-tert-butyloxycarbonylpyrrolidine-3-yl-methylamine (0.36 g, 0.81 mmol) in dichloromethane (10 ml) is stirred at room temperature with trifluoroacetic acid (0.93 g, 8.10 mmol) overnight. The reaction mixture is concentrated in vacuo and the oil is dissolved in methanol, purified using a SCX-2 column (10 g), then washed with methanol. The basic product elutes with methanolic ammonia (2M). Evaporation to an oil and further purification by preparative LC-MS gives a colourless oil. Dissolve the oil in isopropyl alcohol and add L-tartaric acid (1 eq) then heat to give a clear solution. Crystallise by cooling to give the title compound as a colourless solid. $^1$H NMR (300 MHz, DMSO) $\delta_H$: 7.57-7.56 (2H, m), 7.44-7.40 (1H, m), 3.88-3.85 (4H, m), 3.70 (2H, s), 3.24-3.03 (5H, m), 2.77-2.70 (1H, m), 2.59-2.51 (2H, m), 2.44-2.31 (1H, m), 1.94-1.88 (1H, m), 1.66-1.48 (6H, m), LCMS: Rt=4.22 (12 min method) [M+H]=343/5.

EXAMPLE 2

N-{[3,5-Dichlorophenyl]methyl}-N-(tetrahydro-2H-pyran-4-yl)-(3S)-pyrrolidine-3-yl-methylamine L-Tartrate

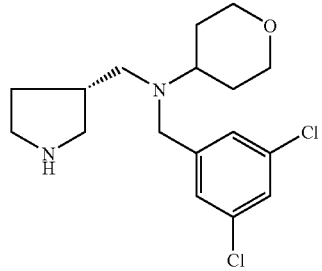

S isomer

The title compound may be prepared following the procedures described in Example 1 except 3,5-dichlorobenzaldehyde replaces 2,4 dichlorobenzaldehyde in step (ii). $^1$H NMR (300 MHz, DMSO) $\delta_H$: 7.56-7.45 (1H, m), 7.35-7.34 (2H, m), 3.88-3.85 (4H, m), 3.65 (2H, s), 3.25-3.02 (5H, m), 2.77-2.71 (1H, m), 2.71-2.51 (1H, m), 2.50-2.49 (2H, m), 2.45-2.33 (1H, m), 1.97-1.91 (1H, m), 1.89-1.45 (5H, m), LCMS: Rt=4.20 (12 min method) [M+H]=343/5.

EXAMPLE 3

N-(2-Methylpropyl)-N-{[2-(trifluoromethyl)phenyl]methyl}-(3R)-pyrrolidine-3-yl-methylamine L-Tartrate

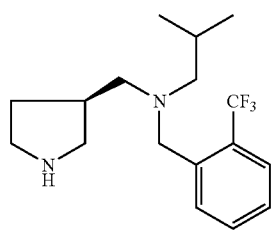

R isomer

The title compound is prepared starting from (S)-3-(aminomethyl)-1-N-tert-butyloxycarbonylpyrrolidine (commercially available from AstaTech, Inc.) following the procedures described in Example 1, except isobutyraldehyde replaces tetrahydro-4H-pyran-4-one in step (i) and 2-trifluoromethylbenzaldehyde replaces 2,4-dichlorobenzaldehyde in step (ii). $^1$H NMR (300 MHz, DMSO) $\delta_H$: 7.83-7.80 (1H, m), 7.70-7.65 (2H, m), 7.48-7.42 (1H, m), 3.88 (2H, s), 3.70-3.59 (2H, m), 3.32-3.26 (1H, m), 3.18-3.02 (2H, m), 2.74-2.68 (1H, m), 2.51-2.50 (1H, m), 2.49-2.36 (2H, m), 2.12-2.03 (2H, m), 2.02-1.97 (1H, m), 1.80-1.71 (1H, hep), 1.56-1.47 (1H, m), 0.82 (6H, d). LCMS: Rt=5.38 (12 min method) [M+H]=315.2.

EXAMPLE 4

N-(2-Methylpropyl)-N-{[2-4-dichlorophenyl]methyl}-(3R)-pyrrolidine-3-yl-methylamine L-Tartrate

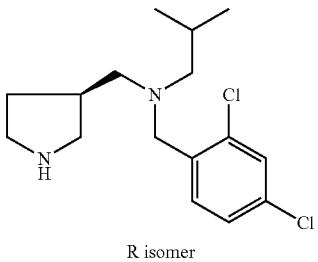

R isomer

The title compound is prepared starting from (S)-3-(aminomethyl)-1-N-tert-butyloxycarbonylpyrrolidine following the procedures described in Example 1, except isobutyraldehyde replaces tetrahydro-4H-pyran-4-one in step (i) and no purification by LC-MS is required as in step (iii). $^1$H NMR (300 MHz, DMSO) $δ_H$: 7.58-7.55 (1H, m), 7.44-7.37 (2H, m), 3.88 (2H, s), 3.66-3.51 (2H, m), 3.29-3.11 (1H, m), 3.08-3.02 (2H, m), 2.73-2.67 (1H, m), 2.49-2.47 (1H, m), 2.44-2.31 (2H, m), 2.13-2.03 (2H, m), 2.01-1.95 (1H, m), 1.77-1.68 (1H, hep), 1.55-1.45 (1H, m), 0.78 (6H, d). LCMS: Rt=5.21 (12 min method) [M+H]=315/7.

EXAMPLE 5

N-(2-Methylpropyl)-N-{[3,5-dichlorophenyl]methyl}-(3R)-pyrrolidine-3-yl-methylamine L-Tartrate

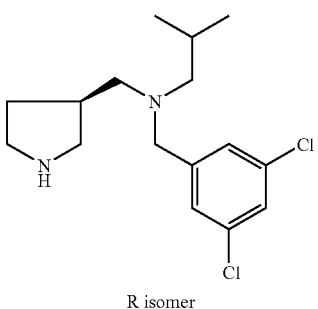

R isomer

The title compound is prepared starting from (S)-3-(aminomethyl)-1-N-tert-butyloxycarbonylpyrrolidine following the procedures described in Example 1, except isobutyraldehyde replaces tetrahydro-4H-pyran-4-one in step (i) and 3,5-dichlorobenzaldehyde replaces 2,4 dichlorobenzaldehyde in step (ii). $^1$H NMR (300 MHz, DMSO) $δ_H$: 7.48-7.47 (1H, m), 7.34-7.33 (2H, m), 3.88 (2H, s), 3.57-3.47 (2H, m), 3.30-3.24 (1H, m), 3.12-3.07 (2H, m), 3.74-2.68 (1H, m), 2.50-2.49 (1H, m), 2.36-2.34 (2H, m), 2.10-2.01 (2H, m), 2.00-1.95 (1H, m), 1.78-1.73 (1H, m), 1.53-1.49 (1H, m), 0.81 (6H, d). LCMS: Rt=5.09 (12 min method) [M+H]=315/7.

EXAMPLE 6

N-{[2,4-Dichlorophenyl]methyl}-N-(tetrahydro-2H-pyran-4-yl)-(3R)-pyrrolidine-3-yl-methylamine L-Tartrate

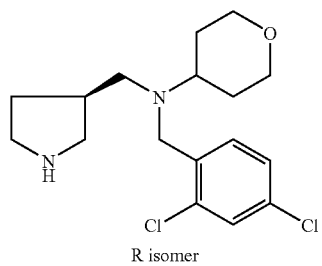

R isomer

The title compound is prepared starting from (S)-3-(aminomethyl)-1-N-tert-butyloxycarbonylpyrrolidine following the procedures described in Example 1. $^1$H NMR (300 MHz, DMSO) $δ_H$: 7.56 (2H, d), 7.42 (1H, dd), 3.89 (1H, s), 3.87 (3H, s), 3.70 (2H, s), 3.25-3.0 (5H, m), 2.77-2.71 (1H, m), 2.69-2.43 (3H, m), 2.38-2.31 (1H, m), 1.94-1.88 (1H, m), 1.66-1.47 (5H, m), LCMS: Rt=4.23 (12 min method) [M+H]=343/5.

EXAMPLE 7

N-{[3,5-Dichlorophenyl]methyl}-N-(tetrahydro-2H-pyran-4-yl)-(3R)-pyrrolidine-3-yl-methylamine L-Tartrate

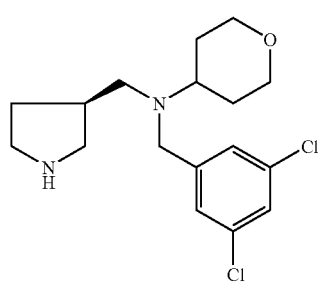

R isomer

The title compound is prepared starting from (S)-3-(aminomethyl)-1-N-tert-butyloxycarbonylpyrrolidine following the procedures described in Example 1 except 3,5-dichlorobenzaldehyde replaces 2,4-dichlorobenzaldehyde in step (ii). $^1$H NMR (300 MHz, DMSO) $δ_H$: 7.47-7.46 (1H, m), 7.35-7.34 (2H, m), 3.90 (1H, brs), 3.88-3.85 (3H, s), 3.65 (2H, s), 3.25-3.01 (5H, m), 2.77-2.62 (1H, m), 2.58-2.52 (1H, m), 2.49 (2H, m), 2.45-2.33 (1H, m), 1.95-1.89 (1H, m), 1.57-1.46 (5H, m), LCMS: Rt=4.20 (12 min method) [M+H]=343/5.

EXAMPLE 8

N-(2-Methylpropyl)-N-{[2-(trifluoromethyl)phenyl]methyl}-(3S)-pyrrolidine-3-yl-methylamine L-Tartrate

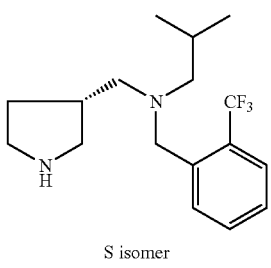

S isomer

The title compound is prepared following the procedures described in Example 1, except isobutyraldehyde replaces tetrahydro-4H-pyran-4-one in step (i) and 2-trifluoromethylbenzaldehyde replace 2,4-dichlorobenzaldehyde in step (ii). $^1$H NMR (300 MHz, DMSO) $\delta_H$: 7.87-7.80 (1H, m), 7.70-7.65 (2H, m), 7.48-7.43 (1H, m), 3.88 (2H, s), 3.75-3.59 (2H, m), 3.32-3.26 (1H, m), 3.19-3.02 (2H, m), 2.74-2.67 (1H, m), 2.51 (1H, s), 2.49-2.36 (2H, m), 2.12-2.10 (2H, m), 2.06-1.98 (1H, m), 1.80-1.71 (1H, hept), 1.57-1.44 (1H, m), 0.82 (6H, d). LCMS: Rt=5.39 (12 min method) [M+H]=315.1.

EXAMPLE 9

N-(2-Methylpropyl)-N-{(2,4-dichlorophenyl)methyl}-(3S)-pyrrolidine-3-yl-methylamine L-Tartrate

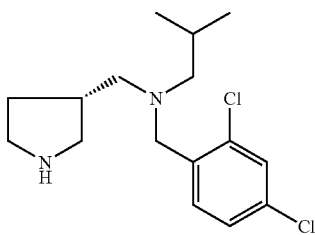

S isomer

The title compound is prepared following the procedures described in Example 1, except isobutyraldehyde replaces tetrahydro-4H-pyran-4-one in step (i). $^1$H NMR (300 MHz, DMSO) $\delta_H$: 7.58-7.55 (1H, m), 7.44-7.37 (2H, m), 3.88 (2H, s), 3.66-3.51 (2H, m), 3.29-3.11 (1H, m), 3.08-3.02 (2H, m), 2.73-2.67 (1H, m), 2.49-2.47 (1H, m), 2.44-2.31 (2H, m), 2.13-2.03 (2H, m), 2.01-1.95 (1H, m), 1.77-1.68 (1H, hept), 1.55-1.45 (1H, m), 0.78 (6H, d). LCMS: Rt=4.97 (12 min method) [M+H]=315/7.

EXAMPLE 10

N-(2-Methylpropyl)-N-{(3,5-dichlorophenyl)methyl}-(3S)-pyrrolidine-3-yl-methylamine L-Tartrate

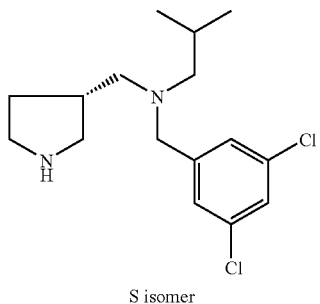

S isomer

The title compound is prepared following the procedures described in Example 1, except isobutyraldehyde replaces tetrahydro-4H-pyran-4-one in step (i) and 3,5-dichlorobenzaldehyde replaces 2,4 dichlorobenzaldehyde in step (ii). $^1$H NMR (300 MHz, DMSO) $\delta_H$: 7.48-7.47 (1H, m), 7.34-7.33 (2H, m), 3.88 (2H, s), 3.57-3.47 (2H, m), 3.30-3.24 (1H, m), 3.12-3.07 (2H, m), 3.74-2.68 (1H, m), 2.50-2.49 (1H, m), 2.36-2.34 (2H, m), 2.10-2.01 (2H, m), 2.00-1.95 (1H, m), 1.78-1.73 (1H, m), 1.53-1.49 (1H, m), 0.81 (6H, d). LCMS: Rt=5.03 (12 min method) [M+H]=315/7.

EXAMPLE 11

N-(1-Methylethyl)-N-{(2,4-dichlorophenyl)methyl}-(3S)-pyrrolidine-3-yl-methylamine L-Tartrate

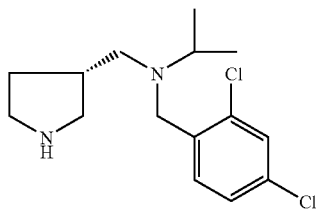

S isomer

Step (i)

N-{(3,4-Dichlorophenyl)methyl}-1-tert-butyloxycarbonyl-(3R)-pyrrolidine-3-yl-methylamine A solution of (R)-3-(aminomethyl)-1-N-tert-butyloxycarbonylpyrrolidine (2.22 g, 11.08 mmol) and 2,4-dichlorobenzaldehyde (2.13 g, 12.19 mmol) in ethanol (30 ml) is stirred under an atmosphere of nitrogen at room temperature for 5.5 h. The solution is cooled to 0° C. and sodium borohydride (0.83 g, 22.16 mmol) is added portionwise and the mixture is stirred for 1 h at room temperature. The reaction mixture is concentrated and water is added prior to extraction with diethyl ether (2×). The extracts are washed with brine, dried over magnesium sulphate, filtered and evaporated to give an oil. The crude oil is purified using a combiflash on an ISCO silica cartridge (120 g) eluting with ethyl acetate to give the required product as a colourless oil.

Step (ii)

N-(1-Methylethyl)-N-{(2,4-dichlorophenyl)methyl}-1-tert-butyloxycarbonyl-(3R)-pyrrolidine-3-yl-methylamine A solution of N-(2,4-dichlorobenzyl)-1-tert-butyloxycarbonyl-(3R)-pyrrolidine-3-yl-methylamine (300 mg, 0.84 mmol), acetone (487 mg, 8.40 mmol) and sodium triacetoxyborohydride (250 mg, 1.18 mmol) in dry dimethylsulphoxide (2 ml) is stirred at room temperature under an atmosphere of nitrogen for 3 days. Water (10 ml) and dichloromethane (10 ml) are added, the mixture is stirred for 5 min then the organic phase is separated using a hydrophobic frit. The organic phase is evaporated and the oil is dissolved in methanol, purified using a SCX-2 column (10 g), washed with methanol and the basic product is eluted with methanolic ammonia (2M). Evaporation gives the required compound as a colourless oil.

Step (iii)

N-(1-Methylethyl)-N-{(2,4-dichlorophenyl)methyl}-(3S)-pyrrolidine-3-yl-methylamine L-Tartrate The title compound is prepared from N-(1-Methylethyl)-N-{(2,4-dichlorophenyl)methyl}-1-tert-butyloxycarbonyl-(3R)-pyrrolidine-3-yl-methylamine following the procedure described in Example 1 (iii) as a colourless solid. $^1$H NMR (300 MHz, DMSO) $\delta_H$: 7.55-7.52 (2H, m), 7.43-7.41 (1H, m), 3.87 (2H, s), 3.61 (2H, s), 3.21-3.07 (3H, m), 2.79-2.75 (2H, m), 2.39-2.33 (3H, m), 2.08-1.90 (1H, m), 1.51-1.49 (1H, m), 0.97 (6H, d). LCMS: Rt=3.09 (12 min method) [M+H]=301/3.

EXAMPLE 12

N-(Propyl)-N-{(2,4-dichlorophenyl)methyl}-(3S)-pyrrolidine-3-yl-methylamine L-Tartrate

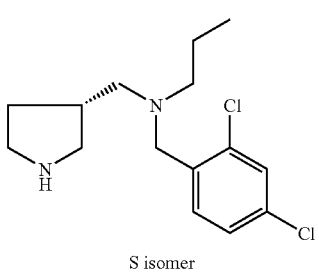

S isomer

The title compound is prepared following the procedures described in Example 11 except that propionaldehyde replaced acetone in step (ii). $^1$H NMR (300 MHz, DMSO) $\delta_H$: 7.58-7.57 (1H, s), 7.53-7.50 (1H, d), 7.44-7.41 (1H, d), 3.88 (2H, s), 3.66-3.54 (2H, m), 3.27-3.21 (1H, m), 3.14-3.02 (2H, m), 2.76-2.70 (1H, m), 2.50-2.46 (3H, m), 2.43-2.31 (2H, m), 2.01-1.93 (1H, m), 1.53-1.38 (3H, m), 0.81-0.76 (3H, m). LCMS: Rt=3.26 (12 min method) [M+H]=301/3.

EXAMPLE 13

N-(Cyclopentyl)-N-{(2,4-dichlorophenyl)methyl}-(3S)-pyrrolidine-3-yl-methylamine L-Tartrate

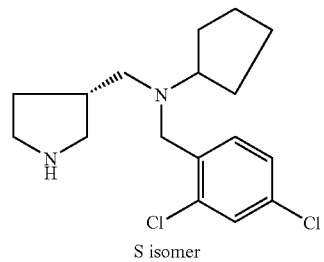

S isomer

The title compound is prepared following the procedures described in Example 11 except that cyclopentanone replaces acetone in step (ii) and no preparative LC-MS is needed in step (iii). $^1$H NMR (300 MHz, DMSO) $\delta_H$: 7.57-7.54 (2H, m), 7.44-7.41 (1H, d), 3.90 (2H, s), 3.65 (2H, s), 3.21-3.00 (4H, m), 2.77-2.71 (1H, m), 2.49 (2H, m), 2.47-2.31 (1H, m), 2.08-1.89 (1H, m), 1.66-1.40 (9H, m). LCMS: Rt=3.68 (12 min method) [M+H]=327/9.

EXAMPLE 14

N-(Cyclopropylmethyl)-N-{(2,4-dichlorophenyl)methyl}-(3S)-pyrrolidine-3-yl-methylamine L-Tartrate

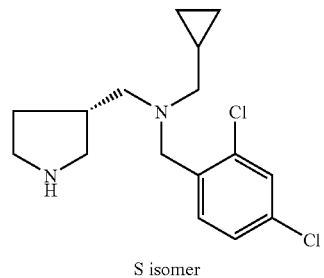

S isomer

The title compound is prepared following the procedures described in Example 11 except that cyclopropanecarboxaldehyde replaces acetone in step (ii) and no preparative LC-MS is needed in step (iii). $^1$H NMR (300 MHz, DMSO) $\delta_H$: 7.57-7.53 (2H, m), 7.43-7.40 (1H, m), 3.92 (2H, s), 3.73-3.64 (2H, m), 3.27-3.21 (1H, m), 3.18-3.02 (2H, m), 2.78-2.72 (1H, m), 2.65-2.48 (3H, m), 2.31 (2H, d), 2.08-1.93 (1H, m), 1.55-1.48 (1H, m), 0.87-0.80 (1H, m), 0.46-0.40 (2H, m), 0.06-0.01 (2H, m). LCMS: Rt=3.30 (12 min method) [M+H]=313/5.

EXAMPLE 15

N-(1-Methylethyl)-N-{(3,5-dichlorophenyl)methyl}-(3R)-pyrrolidine-3-yl-methylamine L-Tartrate

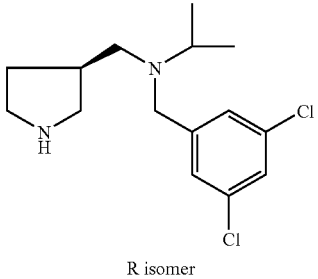

R isomer

The title compound is prepared starting from (S)-3-(aminomethyl)-1-N-tert-butyloxycarbonylpyrrolidine following the procedures described in Example 11, except 3,5-dichlorobenzaldehyde replaces 2,4-dichlorobenzaldehyde in step (i). The L-tartrate salt is obtainable by freeze-drying from water-acetonitrile. $^1$H NMR (300 MHz, DMSO) $\delta_H$: 7.45 (1H, s), 7.34 (2H, s), 3.88 (2H, s), 3.55 (2H, s), 3.22-3.01 (3H, m), 2.83-2.72 (2H, m), 2.37 (3H, brs), 1.98-1.91 (1H, m), 1.60-1.45 (1H, m), 0.97 (6H, m). LCMS: Rt=3.17 (12 min method) [M+H]=301/3.

EXAMPLE 16

N-(Propyl)-N-{(3,5-dichlorophenyl)methyl}-(3R)-pyrrolidine-3-yl-methylamine L-Tartrate

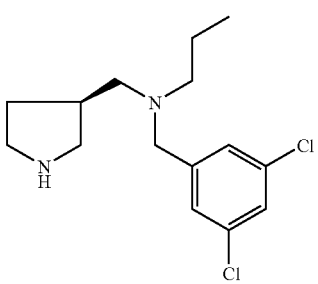

R isomer

The title compound is prepared starting from (S)-3-(aminomethyl)-1-N-tert-butyloxycarbonylpyrrolidine following the procedures described in Example 11 except 3,5-dichlorobenzaldehyde replaces 2,4-dichlorobenzaldehyde in step (i) and propionaldehyde replaces acetone in step (ii). The L-tartrate salt is obtainable by freeze-drying from water-acetonitrile. $^1$H NMR (300 MHz, DMSO) $\delta_H$: 7.47 (1H, s), 7.34 (2H, s), 3.83 (2H, s), 3.54 (2H, s), 3.27-3.21 (1H, m), 3.20-3.05 (2H, m), 2.76-2.70 (1H, m), 2.44-2.29 (5H, m), 2.08-1.85 (1H, m), 1.54-1.37 (3H, m), 0.82-0.78 (3H, m). LCMS: Rt=3.42 (12 min method) [M+H]=301/3.

EXAMPLE 17

N-(Cyclopentyl)-N-{(3,5-dichlorophenyl)methyl}-(3R)-pyrrolidine-3-yl-methylamine L-Tartrate

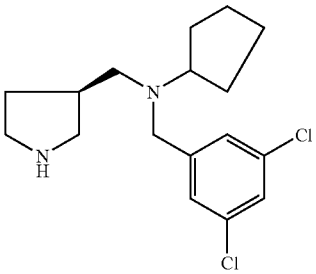

R isomer

The title compound is prepared starting from (S)-3-(aminomethyl)-1-N-tert-butyloxycarbonylpyrrolidine following the procedures described in Example 11 except 3,5-dichlorobenzaldehyde replaces 2,4-dichlorobenzaldehyde in step (i) and cyclopentanone replaces acetone in step (ii) and no LC-MS is required in step (iii). $^1$H NMR (300 MHz, DMSO) $\delta_H$: 7.46 (1H, s), 7.34 (2H, s), 3.90 (2H, s), 3.60 (2H, s), 3.21-3.02 (4H, m), 2.78-2.72 (1H, m), 2.49-2.35 (3H, m), 1.95-1.89 (1H, m), 1.67-1.25 (9H, m). LCMS: Rt=3.77 (12 min method) [M+H]=327/9.

EXAMPLE 18

N-(Cyclopropylmethyl)-N-{(3,5-dichlorophenyl)methyl}-(3R)-pyrrolidine-3-yl-methylamine L-Tartrate

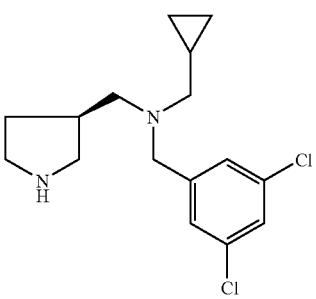

R isomer

The title compound is prepared starting from (S)-3-(aminomethyl)-1-N-tert-butyloxycarbonylpyrrolidine following the procedures described in Example 11 except 3,5-dichlorobenzaldehyde replaces 2,4-dichlorobenzaldehyde in step (i) and cyclopropanecarboxaldehyde replaces acetone in step (ii) and no LC-MS is required in step (iii). $^1$H NMR (300 MHz, DMSO) $\delta_H$: 7.47 (1H, s), 7.36 (2H, s), 3.87 (2H, s), 3.70-3.59 (2H, m), 3.26-3.20 (1H, m), 3.16-3.04 (2H, m), 2.79-2.75 (1H, m), 2.53-2.46 (3H, m), 2.28 (2H, d), 1.99-1.97 (1H, m), 1.54-1.53 (1H, m), 0.87-0.79 (1H, m), 0.49-0.40 (2H, m), 0.05-0.01 (2H, m). LCMS: Rt=3.41 (12 min method) [M+H]=313/5.

EXAMPLE 19

N-(2-Methylpropyl)-N-{[3,5-bis(trifluoromethyl)phenyl]methyl}-(3S)-pyrrolidine-3-yl-methylamine L-Tartrate

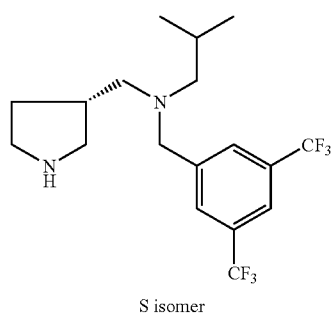

S isomer

The title compound is prepared following the procedures described in Example 1, except isobutyraldehyde replaces tetrahydro-4H-pyran-4-one in step (i) and 3,5-bis(trifluoromethyl)benzaldehyde replaces 2,4-dichlorobenzaldehyde in step (ii) with a purification using the combiflash on an ISCO silica cartridge (35 g) by gradient elution with isohexane-ethyl acetate (0 to 15% over 30 min). No preparative LC-MS is needed in step (iii). $^1$H NMR (300 MHz, DMSO) $\delta_H$: 7.99 (3H, s), 3.87 (2H, s), 3.72 (2H, s), 3.30-3.24 (1H, m), 3.23-3.03 (2H, m), 2.75-2.69 (1H, m), 2.54-2.50 (1H, m), 2.41 (2H, d), 2.10 (2H, d), 2.03-1.97 (1H, m), 1.81-1.73 (1H, m), 1.57-1.48 (1H, m), 0.80 (6H, d). LCMS: Rt=6.14 (12 min method) [M+H]=383.1.

EXAMPLE 20

N-(Phenylmethyl)-N-{(2,4-dichlorophenyl)methyl}-(3S)-pyrrolidine-3-yl-methylamine L-Tartrate

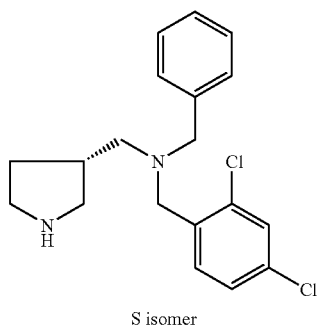

S isomer

The title compound is prepared following the procedures described in Example 11 except that benzaldehyde replaces acetone in step (ii) with a purification using the combiflash on an ISCO silica cartridge (10 g) by gradient elution with isohexane: ethyl acetate (0 to 10% over 35 min). No preparative LC-MS is needed in step (iii). $^1$H NMR (300 MHz, DMSO) $\delta_H$: 7.59-7.57 (2H, m), 7.44-7.41 (1H, m), 7.30-7.16 (5H, m), 3.87 (2H, s), 3.62 (2H, s), 3.56 (2H, s), 3.35-3.20 (1H, m), 3.10-2.91 (2H, m), 2.68-2.50 (2H, m), 2.48-2.30 (2H, m), 2.09-1.88 (2H, m), 1.51-1.30 (1H, m). LCMS: Rt=5.86 (12 min method) [M+H]=349/351.

EXAMPLE 21

N-(Phenylmethyl)-N-{(3,5-dichlorophenyl)methyl}-(3R)-pyrrolidine-3-yl-methylamine L-Tartrate

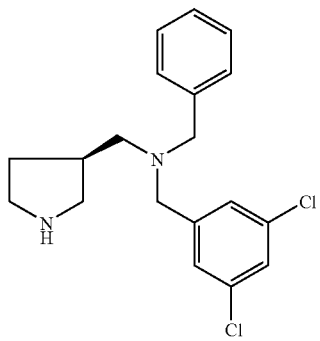

R isomer

The title compound is prepared starting from (S)-3-(aminomethyl)-1-N-tert-butyloxycarbonylpyrrolidine by the procedures described in Example 20. $^1$H NMR (300 MHz, DMSO) $\delta_H$: 7.48 (1H, s), 7.35-7.25 (7H, m), 3.88 (2H, s), 3.54 (4H, s), 3.32-3.26 (1H, m), 3.12-3.03 (2H, m), 2.66-2.50 (2H, m), 2.40-2.31 (2H, m), 2.02-1.96 (1H, m), 1.55-1.38 (1H, m). LCMS: Rt=5.95 (12 min method) [M+H]=349/351.

EXAMPLE 22

N-(2-Methylpropyl)-N-{(2,3-dichlorophenyl)methyl}-(3S)-pyrrolidine-3-yl-methylamine L-Tartrate

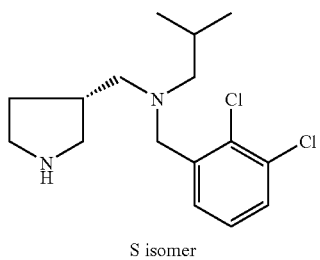

S isomer

Step (i)

N-(2-Methylpropyl)-1-tert-butyloxycarbonyl-(3R)-pyrrolidine-3-yl-methylamine

To a stirred solution of (R)-3-(aminomethyl)-1-N-tert-butyloxycarbonylpyrrolidine (3.0 g, 14.98 mmol) and isobutyraldehyde (1.08 g, 14.98 mmol) in dichloroethane (80 ml) at room temperature is added sodium triacetoxyborohydride (6.33 g, 29.96 mmol). The mixture is stirred overnight and then washed with aqueous saturated sodium bicarbonate. The aqueous is extracted with dichloromethane and the combined organic phases are washed with brine. The organic phase is dried over magnesium sulphate, filtered and evaporated to an oil. Purification using the combiflash on an ISCO silica cartridge (40 g) by gradient elution with dichloromethane-methanol (0-12% over 30 min) give required product as a colourless oil.

Step (ii)

N-(2-Methylpropyl)-N-{(2,3-dichlorophenyl)methyl}-1-tert-butyloxycarbonyl-(3R)-pyrrolidine-3-yl-methylamine The title compound is prepared from (3R)-N-(2-methylpropyl)-1-tert-butyloxycarbonylpyrrolidine-3-yl-methylamine by the procedure described in Example 1 (ii) except 2,3-dichlorobenzaldehyde replaces 2,4-dichlorobenzaldehyde.

Step (iii)

N-(2-Methylpropyl)-N-{(2,3-dichlorophenyl)methyl}-(3S)-pyrrolidine-3-yl-methylamine L-Tartrate The title compound is prepared from N-(2-Methylpropyl)-N-{(2,3-dichloro-phenyl)methyl}-1-tert-butyloxycarbonyl-(3R)-pyrrolidine-3-yl-methylamine following the procedure described in Example 1(iii) but without need for LC-MS purification. $^1$H NMR (300 MHz, DMSO) $\delta_H$: 7.56-7.48 (2H, m), 7.39-7.33 (1H, m), 3.89 (2H, s), 3.89-3.63 (2H, s), 3.30-3.24 (1H, m), 3.14-3.02 (2H, m), 2.74-2.68 (1H, m), 2.50-2.39 (3H, m), 2.14 (2H, d), 2.02-1.96 (1H, m), 1.77-1.68 (1H, m), 1.56-1.46 (1H, m), 0.79 (6H, m). LCMS: Rt=5.17 (12 min method) [M+H]=315/7.

EXAMPLE 23

N-(2-Methylpropyl)-N-{(3,4-dichlorophenyl)methyl}-(3S)-pyrrolidine-3-yl-methylamine L-Tartrate

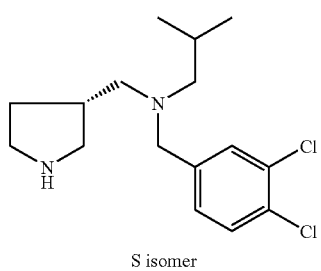

S isomer

The title compound is prepared following the procedures described in Example 22 except 3,4-dichlorobenzaldehyde replaces 2,3-dichlorobenzaldehyde in step (ii). $^1$H NMR (300 MHz, DMSO) $\delta_H$: 7.58 (1H, d), 7.53 (1H, s), 7.31-7.29 (1H, d), 3.89 (2H, s), 3.56-3.44 (2H, s), 3.27-3.23 (1H, m), 3.15-3.02 (2H, m), 2.72-2.67 (1H, m), 2.50-2.49 (1H, m), 2.46-2.33 (2H, d), 2.10-2.08 (2H, d), 2.08-1.95 (1H, m), 1.81-1.72 (1H, m), 1.60-1.40 (1H, m), 0.82 (6H, d). LCMS: Rt=4.62 (12 min method) [M+H]=315/7.

EXAMPLE 24

N-(2-Methylpropyl)-N-{[4-fluoro-2-(trifluoromethyl)phenyl]methyl}-(3S)-pyrrolidine-3-yl-methylamine L-Tartrate

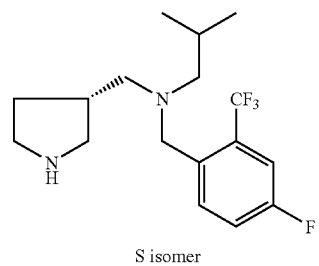

S isomer

The title compound is prepared following the procedures described in Example 22 except 4-fluoro-2-(trifluoromethyl)benzaldehyde replaces 2,3-dichlorobenzaldehyde in step (ii). $^1$H NMR (300 MHz, DMSO) $\delta_H$: 7.86-7.81 (1H, m), 7.58-7.54 (2H, m), 3.89 (2H, s), 3.67-3.57 (2H, m), 3.31-3.19 (1H, m), 3.17-3.02 (2H, m), 2.73-2.67 (1H, m), 2.50-2.49 (1H, m), 2.46-2.35 (2H, d), 2.11-2.09 (2H, d), 2.03-1.97 (1H, m), 1.79-1.71 (1H, m), 1.56-1.43 (1H, m), 0.81 (6H, d). LCMS: Rt=5.82 (12 min method) [M+H]=333.1.

EXAMPLE 25

N-(2-Methylpropyl)-N-{(2-chloro-4-fluorophenyl)methyl}-(3S)-pyrrolidine-3-yl-methylamine L-Tartrate

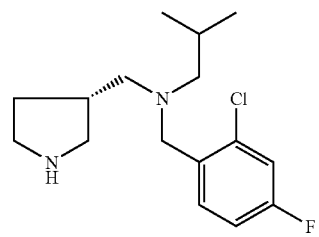

S isomer

The title compound is prepared following the procedures described in Example 22 except 2-chloro-4-fluorobenzaldehyde replaces 2,3-dichlorobenzaldehyde in step (ii). $^1$H NMR (300 MHz, DMSO) $\delta_H$: 7.54-7.42 (1H, m), 7.41-7.38 (1H, m), 7.25-7.19 (1H, m), 3.88 (2H, s), 3.63-3.51 (2H, m), 3.29-3.23 (1H, m), 3.13-3.02 (2H, m), 2.72-2.66 (1H, m), 2.50-2.44 (1H, m), 2.39-2.36 (2H, m), 2.11 (2H, d), 2.10-1.95 (1H, m), 1.76-1.68 (1H, m), 1.55-1.45 (1H, m), 0.80 (6H, d). LCMS: Rt=4.22 (12 min method) [M+H]=299.1.

EXAMPLE 26

N-(2-Methylpropyl)-N-{(2,4-difluorophenyl)methyl}-(3S)-pyrrolidine-3-yl-methylamine L-Tartrate

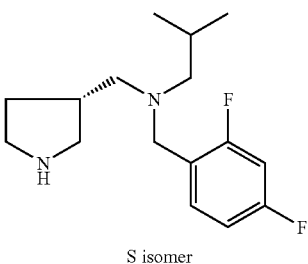

S isomer

The title compound is prepared following the procedures described in Example 22 except 2,4-difluorobenzaldehyde replaces 2,3-dichlorobenzaldehyde in step (ii). $^1$H NMR (300 MHz, DMSO) $\delta_H$: 7.46-7.38 (1H, m), 7.22-7.15 (1H, m), 7.08-7.04 (1H, m), 3.88 (2H, s), 3.58-3.47 (2H, m), 3.27-3.21 (1H, m), 3.13-3.02 (2H, m), 2.72-2.66 (1H, m), 2.53-2.42 (1H, m), 2.35-2.25 (2H, d), 2.12-2.07 (2H, d), 2.02-1.93 (1H, m), 1.78-1.69 (1H, m), 1.54-1.44 (1H, m), 0.79-0.77 (6H, m). LCMS: Rt=3.15 (12 min method) [M+H]=283.2.

EXAMPLE 27

N-(2-Methylpropyl)-N-{[(1,1-Biphenyl)-2ylmethyl}-(3S)-pyrrolidine-3-yl-methylamine L-Tartrate

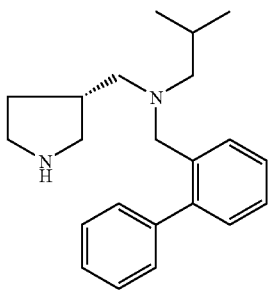

S isomer

Step (i)

N-(2-Methylpropyl)-N-{[(1,1-Biphenyl)-2ylmethyl}-1-tert-butyloxycarbonyl-(3R)-pyrrolidine-3-yl-methylamine To a stirred suspension of N-(2-methylpropyl)-1-tert-butyloxycarbonyl-(3R)-pyrrolidine-3-ylmethylamine (234 mg, 0.91 mmol) and anhydrous potassium carbonate (201 mg, 1.46 mmol) in dry acetonitrile (10 ml) is added 2-phenylbenzyl bromide (271 mg, 1.10 mmol). The mixture is stirred at room temperature for 2 days, concentrated and diluted with water. Extract with dichloromethane, extract concentrated and dilute with methanol, purify using a SCX-2 column (10 g), wash with methanol and the basic product elutes with methanolic ammonia (2M). Evaporation gives the required compound as a colourless oil.

Step (ii)

N-(2-Methylpropyl)-N-{[(1,1-Biphenyl)-2ylmethyl}-(3S)-pyrrolidine-3-yl-methylamine L-Tartrate The title compound is prepared from N-(2-methylpropyl)-N-{[(1,1-Biphenyl)-2ylmethyl}-1-tert-butyloxycarbonyl-(3R)-pyrrolidine-3-ylmethylamine following the procedure described in Example 1 (iii) but without the need for LC-MS purification. The L-tartrate salt is obtained by freeze-drying from water-acetonitrile. $^1$H NMR (300 MHz, DMSO) $\delta_H$: 7.58-7.55 (1H, d), 7.45-7.29 (7H, m), 7.19-7.16 (1H, d), 3.88 (2H, s), 3.53-3.43 (2H, m), 3.17-3.0 (3H, m), 2.61-2.55 (1H, m), 2.39-2.20 (1H, m), 2.19 (2H, d), 1.95 (2H, d), 1.87-1.85 (1H, m), 1.62-1.58 (1H, m), 1.43-1.36 (1H, m), 0.73 (6H, d. LCMS: Rt=4.20 (12 min method) [M+H]=323.2.

EXAMPLE 28

N-(2-Methylpropyl)-N-{[(1,1-Biphenyl)-2ylmethyl}-(3R)-pyrrolidine-3-yl-methylamine L-Tartrate

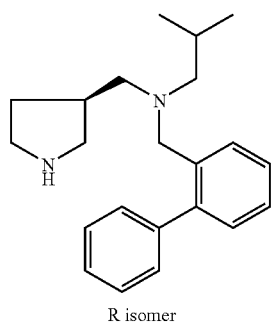

R isomer

The title compound is prepared from N-(2-methylpropyl)-1-tert-butyloxycarbonyl-(3S)-pyrrolidine-3-ylmethylamine following the procedure described in Example 27 to give a colourless solid after crystallisation. $^1$H NMR (300 MHz, DMSO) $\delta_H$: 7.58-7.50 (1H, d), 7.45-7.25 (7H, m), 7.19-7.16 (1H, d), 3.88 (2H, s), 3.53-3.42 (2H, m), 3.20-2.91 (3H, m), 2.61-2.55 (1H, m), 2.40-2.20 (1H, m), 2.19 (2H, d), 1.95 (2H, d), 1.87-1.85 (1H, m), 1.62-1.58 (1H, m), 1.43-1.36 (1H, m), 0.70 (6H, d). LCMS: Rt=4.21 (12 min method) [M+H]=323.2.

EXAMPLE 29

N-(1-Ethyl)-N-{(3,5-dichlorophenyl)methyl}-(3R)-pyrrolidine-3-yl-methylamine L-Tartrate

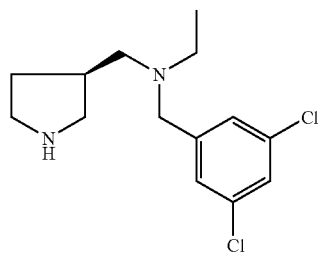

R isomer

A solution of N-(3,5-dichlorobenzyl)-1-tert-butyloxycarbonyl-(3S)-pyrrolidine-3-yl-methylamine (273 mg, 0.76 mmol), acetaldehyde (0.2 ml, 3.56 mmol) and sodium triacetoxyborohydride (711 mg, 3.37 mmol) in dry dichloroethane (50 ml) is stirred at room temperature under an atmosphere of nitrogen for 3 h after which a further portion of acetaldehyde is added (0.2 ml, 3.56 mmol). The reaction is allowed to stir for 3 days. The reaction solution is poured onto an ice cold saturated solution of $NaHCO_3$ and then after stirring the dichloroethane layer is separated via a hydrophobic frit. The organic phase is evaporated and the oil dissolved in methanol, purified using a SCX-2 column (10 g), which is washed with methanol and the basic product elutes with methanolic ammonia (2M). The eluent is evaporated and the residue then dissolved in 2:1 dichloromethane/trifluoroacetic acid (30 ml) and this solution is stirred overnight. The next day the solution is evaporated and the residue purified using a SCX-2 column from which a colourless oil is obtained. Dissolve oil in isopropyl alcohol and add L-tartaric acid (1 eq), heat to give a clear solution. Crystallise on cooling to give the title compound as a colourless solid. $^1$H NMR (300 MHz, DMSO) $\delta_H$: 7.48 (1H, s), 7.35 (2H, s), 3.96 (2H, s), 3.61-3.50 (2H, m), 3.28-3.07 (3H, m), 2.80-2.73 (1H, m), 2.50-2.32 (3H, m), 1.99-1.90 (1H, m), 1.55-1.49 (1H, m), 0.98-0.94 (3H, m). LCMS: Rt=2.69 (12 min method) [M+H]=287/9.

EXAMPLE 30

N-(2-2-Dimethylpropyl)-N-{(2,4-dichlorophenyl)methyl}-(3S)-pyrrolidine-3-yl-methylamine L-Tartrate

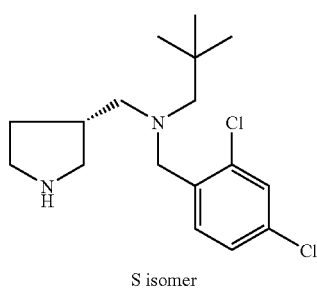

S isomer

A solution of N-(2,4-dichlorobenzyl)-1-tert-butyloxycarbonyl-(3R)-pyrrolidine-3-ylmethylamine (409 mg, 1.14 mmol), trimethylacetaldehyde (0.5 ml, 3.56 mmol) and sodium triacetoxyborohydride (698 mg, 3.31 mmol) in dry dichloroethane (50 ml) is stirred at room temperature under an atmosphere of nitrogen over the weekend. After which further portions of trimethylacetaldehyde (6 ml, 55.33 mmol) and sodium triacetoxyborohydride (867 mg, 4.11 mmol) are added. The reaction is then stirred overnight and the next day the reaction solution is poured onto an ice cold saturated solution of $NaHCO_3$ and then after stirring the dichloroethane layer is separated via a hydrophobic frit. The organic phase is evaporated and the oil dissolved in methanol, purified using a SCX-2 column (10 g), which is washed with methanol and the basic product then elutes with methanolic ammonia (2M). The eluent is evaporated and the residue then dissolved in 2:1 dichloromethane/trifluoroacetic acid (30 ml) and this solution is stirred overnight. The solution is evaporated and the residue purified via prep-LCMS to give a colourless oil. Dissolve oil in isopropyl alcohol, add L-tartaric acid (1 eq) and warm to give a solution. Cyclohexane is added and the colourless crystals filtered and dried in vacuo at 60° C. $^1$H NMR (300 MHz, DMSO) $\delta_H$: 7.62 (1H, d), 7.58 (1H, s), 7.45 (1H, d), 3.91 (2H, s), 3.65 (2H, s), 3.35-3.29 (1H, m), 3.14-3.02 (2H, m), 2.71-2.64 (1H, m), 2.48-2.36 (1H, m), 2.29 (2H, s), 2.08-1.97 (1H, m), 1.56-1.43 (1H, m), 1.40 (2H, s), 0.80 (9H, s). LCMS: Rt=6.18 (12 min method) [M+H]=329/331.

EXAMPLE 31

N-(Cyclopropylmethyl)-N-{(3,5-dichlorophenyl)methyl}-(3S)-pyrrolidine-3-ylmethylamine L-Tartrate

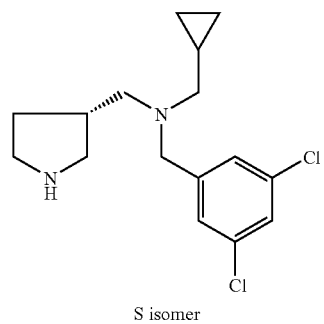

S isomer

The title compound is prepared following the procedures described in Example 11 except that 3,5-dichlorobenzaldehyde replaces 2,4-dichlorobenzaldehyde in step (i) and cyclopropanecarboxaldehyde replaces acetone in step (ii) and stirred only overnight. No preparative LC-MS is required prior to forming the L-tartrate salt. $^1$H NMR (300 MHz, DMSO) $\delta_H$: 7.42 (1H, s), 7.32 (2H, s), 3.88 (2H, s), 3.65-3.55 (2H, m), 3.21-3.09 (1H, m), 3.07-3.04 (2H, m), 2.75-2.71 (1H, m), 2.51-2.46 (3H, m), 2.25-2.0 (2H, d), 2.10-1.93 (1H, m), 1.51-1.45 (1H, m), 0.90-0.83 (1H, m), 0.40-0.37 (2H, m), 0.01 (2H, m). LCMS: Rt=3.42 (12 min method) [M+H]=313/5.

EXAMPLE 32

N-(Cyclohexyl)-N-{(2,4-dichlorophenyl)methyl}-(3S)-pyrrolidine-3-ylmethylamine L-Tartrate

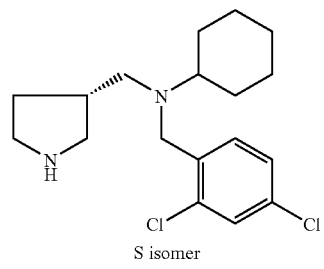

S isomer

The title compound is prepared following the procedures described in Example 11 except that cyclohexanone replaces acetone in step (ii) and no preparative LC-MS is needed in step (iii). $^1$H NMR (300 MHz, DMSO) $\delta_H$: 7.50 (2H, d), 7.40 (1H, dd), 3.87 (2H, s), 3.68 (2H, s), 3.19-3.0 (2H, m), 2.76-2.69 (1H, m), 2.51-2.42 (3H, m), 2.40-2.28 (2H, m), 1.93-

1.80 (1H, m), 1.73 (4H, brd), 1.57-1.47 (2H, m), 1.38-1.02 (6H, m). LCMS: Rt=4.4 (12 min method) [M+H]=341/3.

EXAMPLE 33

N-(2-Methylpropyl)-N-{(2-chlorophenyl)methyl}-(3R)-pyrrolidine-3-ylmethylamine L-Tartrate

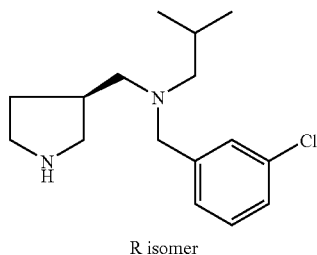

R isomer

The title compound is prepared starting from (S)-3-(aminomethyl)-1-N-tert-butyloxycarbonylpyrrolidine following the procedures described in Example 1, except isobutyraldehyde replaces tetrahydro-4H-pyran-4-one in step (i) and 2-chlorobenzaldehyde replaces 2,4-dichlorobenzaldehyde in step (ii). No preparative LC-MS is required prior to forming the L-tartrate salt. $^1$H NMR (300 MHz, DMSO) $\delta_H$: 7.51-7.49 (1H, m), 7.42 (1H, d), 7.39-7.25 (2H, m), 3.88 (2H, s), 3.68-3.52 (2H, m), 3.31-3.24 (1H, m), 3.17-3.0 (2H, m), 2.74-2.65 (1H, m), 2.58-2.41 (1H, m), 2.40-2.30 (2H, m), 2.11 (2H, d), 2.15-1.90 (1H, m), 1.79-1.62 (1H, m), 1.55-1.42 (1H, m), 0.80-0.62 (6H, m). LCMS: Rt=3.59 (12 min method) [M+H]=281.1.

EXAMPLE 34

N-(2-Methylpropyl)-N-{(3-chlorophenyl)methyl}-(3R)-pyrrolidine-3-ylmethylamine L-Tartrate

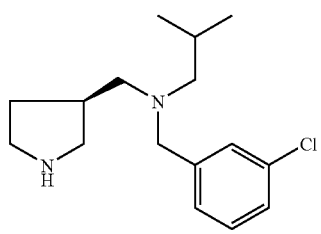

R isomer

The title compound is prepared starting from (S)-3-(aminomethyl)-1-N-tert-butyloxycarbonylpyrrolidine following the procedures described in Example 1, except isobutyraldehyde replaces tetrahydro-4H-pyran-4-one in step (i) and 3-chlorobenzaldehyde replaces 2,4-dichlorobenzaldehyde in step (ii). No preparative LC-MS is required prior to forming the L-tartrate salt. $^1$H NMR (300 MHz, DMSO) $\delta_H$: 7.38-7.21 (4H, m), 3.88 (2H, s), 3.60-3.45 (2H, m), 3.31-3.23 (1H, m), 3.17-3.02 (2H, m), 2.75-2.65 (1H, m), 2.58-2.41 (1H, m), 2.35 (2H, d), 2.11 (2H, d), 2.05-1.91 (1H, m), 1.81-1.69 (1H, m), 1.55-1.42 (1H, m), 0.80 (6H, d). LCMS: Rt=3.46 (12 min method) [M+H]=281.1.

EXAMPLE 35

N-(2-Methylpropyl)-N-{(4-chlorophenyl)methyl}-(3R)-pyrrolidine-3-ylmethylamine L-Tartrate

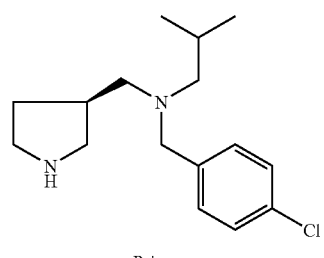

R isomer

The title compound is prepared starting from (S)-3-(aminomethyl)-1-N-tert-butyloxycarbonylpyrrolidine following the procedures described in Example 1, except isobutyraldehyde replaces tetrahydro-4H-pyran-4-one in step (i) and 4-chlorobenzaldehyde replaces 2,4-dichlorobenzaldehyde in step (ii). No preparative LC-MS is required prior to forming the L-tartrate salt. $^1$H NMR (300 MHz, DMSO) $\delta_H$: 7.37 (2H, d), 7.31 (2H, d), 3.91 (2H, s), 3.54-3.42 (2H, m), 3.29-3.23 (1H, m), 3.12-3.02 (2H, m), 2.71-2.65 (1H, m), 2.50-2.43 (1H, m), 2.32 (2H, d), 2.08 (2H, d), 2.07-1.94 (1H, m), 1.80-1.71 (1H, m), 1.53-1.41 (1H, m), 0.81 (6H, d). LCMS: Rt=3.20 (12 min method) [M+H]=281.

EXAMPLE 36

N-(2-Methylpropyl)-N-{(2,5-dichlorophenyl)methyl}-(3R)-pyrrolidine-3-ylmethylamine L-Tartrate

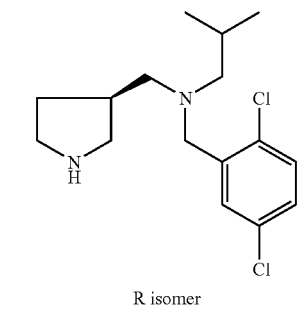

R isomer

The title compound is prepared starting from (S)-3-(aminomethyl)-1-N-tert-butyloxycarbonylpyrrolidine following the procedures described in Example 1, except isobutyraldehyde replaces tetrahydro-4H-pyran-4-one in step (i) and 2,5-dichlorobenzaldehyde replaces 2,4-dichlorobenzaldehyde in step (ii). No preparative LC-MS is required prior to forming the L-tartrate salt. $^1$H NMR (300 MHz, DMSO) $\delta_H$: 7.55-7.54 (1H, m), 7.48-7.45 (1H, m), 7.38-7.34 (1H, dd), 3.88 (2H, s), 3.65-3.54 (2H, m), 3.30-3.20 (1H, m), 3.18-3.03 (2H, m), 2.76-2.69 (1H, m), 2.55-2.50 (1H, m), 2.42 (2H, d), 2.12 (2H, d), 2.05-1.94 (1H, m), 1.78-1.70 (1H, m), 1.57-1.45 (1H, m), 0.81 (6H, d). LCMS: Rt=5.29 (12 min method) [M+H]=3157.

EXAMPLE 37

N-(2-Methylpropyl)-N-{(2-chlorophenyl)methyl}-(3S)-pyrrolidine-3-ylmethylamine L-Tartrate

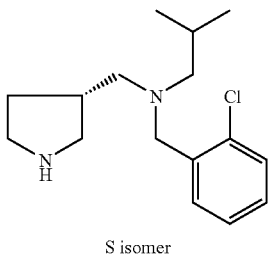

S isomer

The title compound is prepared starting from (R)-3-(aminomethyl)-1-N-tert-butyloxycarbonylpyrrolidine following the procedures described in Example 1, except isobutyraldehyde replaces tetrahydro-4H-pyran-4-one in step (i) and 2-chlorobenzaldehyde replaces 2,4-dichlorobenzaldehyde in step (ii). No preparative LC-MS is required prior to forming the L-tartrate salt. $^1$H NMR (300 MHz, DMSO) $\delta_H$: 7.50-7.48 (1H, dd), 7.42-7.40 (1H, dd), 7.35-7.25 (2H, m), 3.88 (2H, s), 3.66-3.54 (2H, m), 3.30-3.24 (1H, m), 3.16-3.02 (2H, m), 2.73-2.67 (1H, m), 2.55-2.40 (1H, m), 2.38-2.33 (2H, m), 2.12 (2H, d), 2.15-1.93 (1H, m), 1.77-1.68 (1H, m), 1.55-1.43 (1H, m), 0.80-0.77 (6H, m). LCMS: Rt=3.56 (12 min method) [M+H]=281.1.

EXAMPLE 38

N-(2-Methylpropyl)-N-{(3-chlorophenyl)methyl}-(3S)-pyrrolidine-3-ylmethylamine L-Tartrate

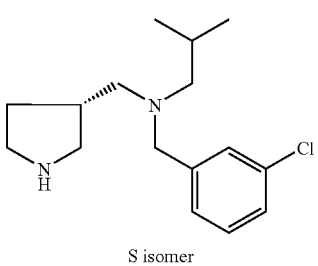

S isomer

The title compound is prepared starting from (R)-3-(aminomethyl)-1-N-tert-butyloxycarbonylpyrrolidine following the procedures described in Example 1, except isobutyraldehyde replaces tetrahydro-4H-pyran-4-one in step (i) and 3-chlorobenzaldehyde replaces 2,4-dichlorobenzaldehyde in step (ii). No preparative LC-MS is required prior to forming the L-tartrate salt. $^1$H NMR (300 MHz, DMSO) $\delta_H$: 7.38-7.21 (4H, m), 3.88 (2H, s), 3.60-3.45 (2H, m), 3.31-3.23 (1H, m), 3.17-3.02 (2H, m), 2.75-2.65 (1H, m), 2.58-2.41 (1H, m), 2.35 (2H, d), 2.11 (2H, d), 2.05-1.91 (1H, m), 1.81-1.69 (1H, m), 1.55-1.42 (1H, m), 0.80 (6H, d). LCMS: Rt=3.44 (12 min method) [M+H]=281.1.

EXAMPLE 39

N-(2-Methylpropyl)-N-{(4-chlorophenyl)methyl}-(3S)-pyrrolidine-3-ylmethylamine L-Tartrate

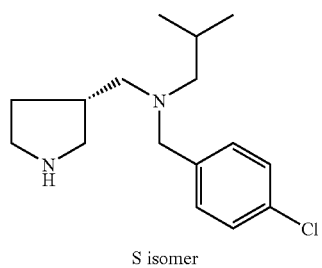

S isomer

The title compound is prepared starting from (R)-3-(aminomethyl)-1-N-tert-butyloxycarbonylpyrrolidine following the procedures described in Example 1, except isobutyraldehyde replaces tetrahydro-4H-pyran-4-one in step (i) and 4-chlorobenzaldehyde replaces 2,4-dichlorobenzaldehyde in step (ii). No preparative LC-MS is required prior to forming the L-tartrate salt. $^1$H NMR (300 MHz, DMSO) $\delta_H$: 7.38 (2H, d), 7.30 (2H, d), 3.88 (2H, s), 3.54-3.40 (2H, m), 3.29-3.23 (1H, m), 3.12-3.02 (2H, m), 2.71-2.65 (1H, m), 2.50-2.43 (1H, m), 2.35-2.21 (2H, m), 2.08 (2H, d), 2.07-1.90 (1H, m), 1.80-1.69 (1H, m), 1.53-1.40 (1H, m), 0.80 (6H, d). LCMS: Rt=3.18 (12 min method) [M+H]=281.2.

EXAMPLE 40

N-(2-Methylpropyl)-N-{(2,5-dichlorophenyl)methyl}-(3S)-pyrrolidine-3-ylmethylamine L-Tartrate

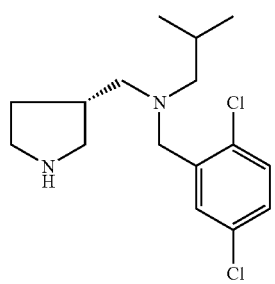

S isomer

The title compound is prepared starting from (R)-3-(aminomethyl)-1-N-tert-butyloxycarbonylpyrrolidine following the procedures described in Example 1, except isobutyraldehyde replaces tetrahydro-4H-pyran-4-one in step (i) and 2,5-dichlorobenzaldehyde replaces 2,4-dichlorobenzaldehyde in step (ii). No preparative LC-MS is required prior to forming the L-tartrate salt. $^1$H NMR (300 MHz, DMSO) $\delta_H$: 7.55 (1H, d), 7.49 (1H, d), 7.39 (1H, dd), 3.88 (2H, s), 3.67-3.51 (2H, m), 3.31-3.24 (1H, m), 3.18-3.03 (2H, m), 2.78-2.69 (1H, m), 2.55-2.50 (1H, m), 2.42 (2H, d), 2.12 (2H, d), 2.05-1.94 (1H, m), 1.78-1.70 (1H, m), 1.57-1.45 (1H, m), 0.80 (6H, d). LCMS: Rt=5.26 (12 min method) [M+H]=315/7.

EXAMPLE 41

N-(2-Methylpropyl)-N-(benzyl)-(3S)-pyrrolidine-3-ylmethylamine L-Tartrate

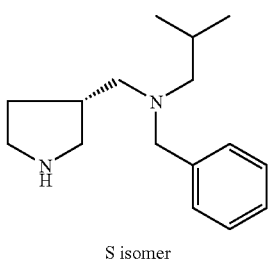

S isomer

The title compound is prepared starting from (R)-3-(aminomethyl)-1-N-tert-butyloxycarbonylpyrrolidine following the procedures described in Example 1, except isobutyraldehyde replaces tetrahydro-4H-pyran-4-one in step (i) and benzaldehyde replaces 2,4-dichlorobenzaldehyde in step (ii). No preparative LC-MS is required prior to forming the L-tartrate salt. $^1$H NMR (300 MHz, DMSO) $\delta_H$: 7.36-7.20 (5H, m), 3.89 (2H, s), 3.54-3.41 (2H, m), 3.31-3.23 (1H, m), 3.15-3.02 (2H, m), 2.72-2.61 (1H, m), 2.55-2.49 (1H, m), 2.39-2.25 (2H, m), 2.10 (2H, d), 2.05-1.91 (1H, m), 1.85-1.70 (1H, m), 1.56-1.40 (1H, m), 0.80 (6H, d). LCMS: Rt=2.04 (12 min method) [M+H]=247.1.

EXAMPLE 42

N-(Ethyl)-N-{(2,4-dichlorophenyl)methyl}-(3R)-pyrrolidine-3-ylmethylamine L-Tartrate

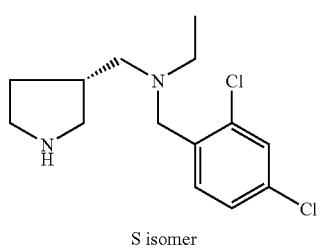

S isomer

The title compound is prepared following the procedures described in Example 11 except that acetaldehyde replaces acetone in step (ii) and the L-tartrate salt is obtained by freeze-drying from an acetonitrile-water solution. $^1$H NMR (300 MHz, DMSO) $\delta_H$: 7.58 (1H, s), 7.50 (1H, d), 7.42(1H, d), 3.90 (2H, s), 3.60 (2H, q), 3.28-3.02 (3H, m), 2.80-2.70 (1H, m), 2.50-2.36 (5H, m), 2.02-1.90 (1H, m), 1.59-1.45 (1H, m), 0.98 (3H, t). LCMS: Rt=2.38 (12 min method) [M+H]=0.287/9.

EXAMPLE 43

N-(Cyclopentyl)-N-{(2,4-dichlorophenyl)methyl}-(3R)-pyrrolidine-3-ylmethylamine L-Tartrate

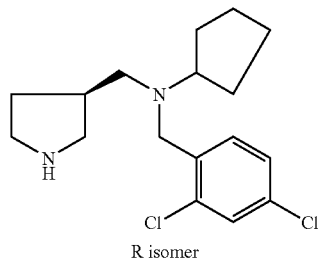

R isomer

The title compound is prepared starting from (S)-3-(aminomethyl)-1-N-tert-butyloxycarbonylpyrrolidine following the procedures described in Example 11 except cyclopentanone replaces acetone in step (ii). $^1$H NMR (300 MHz, DMSO) $\delta_H$: 7.57-7.52 (2H, m), 7.42 (1H, dd), 3.80 (2H, s), 3.65 (2H, s), 3.21-2.99 (4H, m), 2.79-2.70 (1H, m), 2.50-2.40 (2H, m), 2.40-2.25 (1H, m), 1.99-1.85 (1H, m), 1.66-1.40 (9H, m). LCMS: Rt=3.68 (12 min method) [M+H]=327/9.

EXAMPLE 44

N-(2-Methylpropyl)-N-{(4-chloro-2-ethoxyphenyl)methyl}-(3S)-pyrrolidine-3-ylmethylamine L-Tartrate

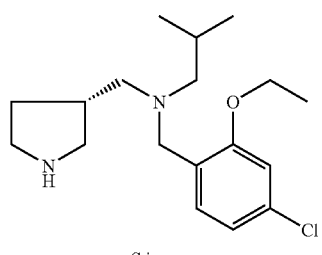

S isomer

Step (i)

Ethyl 4-chloro-2-ethoxybenzoate

A mixture of 4-chlorosalicylic acid (10.0 g, 57.94 mmol) and potassium carbonate (80 g, 0.58 mol) and diethyl sulphate (18.76 g, 0.122 mol) in acetone (150 ml) is heated at reflux with stirring for 24 h. The suspension is cooled and diluted with water (200 ml). Extract with diethyl ether (2×) and wash the extracts with water (2×) and brine. The organic phase is dried over magnesium sulphate, filtered and evaporated to a brown oil. The oil is purified using the combiflash on a 120 g silica cartridge eluting with isohexane-ethyl acetate (0 to 25% over 30 min.) to give ethyl 4-chloro-2-ethoxybenzoate as a colourless oil.

45

Step (ii)

4-Chloro-2-ethoxybenzyl alcohol

To a stirred suspension of lithium aluminum hydride (4.12 g, 0.108 mol) in dry tetrahydrofuran under an atmosphere of nitrogen cooled to 5° C. is added a solution of ethyl 4-chloro-2-ethoxybenzoate (12.4 g, 54.24 mmol) in dry tetrahydrofuran (20 ml) dropwise over 15 min. The suspension is stirred at room temperature overnight then cooled to 0° C. and water (4.12 ml), aq. 15% sodium hydroxide (4.12 ml) and water (12.4 ml) added dropwise. The resulting suspension is filtered through celite and washed with ethyl acetate. Evaporate to give a colourless oil that crystallises on standing, triturate with iso-hexane and filter to give 4-chloro-2-ethoxybenzyl alcohol as a colourless solid.

Step (iii)

4-Chloro-2-ethoxybenzaldehyde

Oxalyl chloride (4.87 g, 38.4 mmol) is added to dry dichloromethane (80 ml) cooled to below −60° C. under an atmosphere of nitrogen followed by dropwise addition of a solution of dry dimethyl sulphoxide (6.25 g, 80.10 mmol) in dry dichloromethane (25 ml) with stirring. After stirring for 15 min. at −78° C., a solution of 4-chloro-2-ethoxybenzyl alcohol (5.97 g, 32.0 mmol) in dry dichloromethane (35 ml) is added dropwise to give a white suspension. The suspension is stirred at −78° C. for 0.5 h then added triethylamine (16.18 g, 0.16 mol) rapidly. The mixture is stirred at room temperature for 1.5 h before quenching with aqueous saturated sodium bicarbonate (100 ml). The aqueous phase is separated and extracted with dichloromethane (2×). The combined organic phases is washed with aqueous HCl (1M) and then with brine, dried over magnesium sulphate, filtered and evaporated to a yellow solid. The solid is dissolved in diethyl ether and purified by eluting through a short plug of flash silica. Evaporate to give 4-chloro-2-ethoxybenzaldehyde as a pale yellow solid.

Step (iv)

N-(2-Methylpropyl)-N-{(4-chloro-2-ethoxyphenyl)methyl}-(3S)-pyrrolidine-3-ylmethylamine L-Tartrate The title compound is prepared starting from (R)-3-(aminomethyl)-1-N-tert-butyloxycarbonylpyrrolidine following the procedures described in Example 1, except isobutyraldehyde replaces tetrahydro-4H-pyran-4-one in step (i) and 4-chloro-2-ethoxybenzaldehyde replaces 2,4-dichlorobenzaldehyde in step (ii). Purification using the combiflash on a 40 g silica cartridge by gradient elution with isohexane-ethyl acetate (0 to 50% over 20 min.) replaces SCX-2 in step (ii). No preparative LC-MS is required prior to forming the L-tartrate salt by freeze-drying from acetonitrile-water. (401 mg). $^1$H NMR (300 MHz, DMSO) $\delta_H$: 7.30 (1H, d), 7.01 (1H, s), 6.94 (1H, d), 4.10-3.99 (2H, m), 3.88 (2H, s), 3.48 (2H, s), 3.30-3.20 (1H, m), 3.19-3.02 (2H, m), 2.75-2.65 (1H, m), 2.50-2.42 (1H, m), 2.38-2.25 (2H, m), 2.18 (2H, d), 2.01-1.90 (1H, m), 1.81-1.68 (1H, m), 1.55-1.40 (1H, m), 1.38-1.28 (3H, m), 0.81 (6H, d). LCMS: Rt=3.31 (12 min method) [M+H]=325.2.

46

EXAMPLE 45

N-(2-Methylpropyl)-N-{[2-(difluoromethoxy)phenyl]methyl}-(3S)-pyrrolidine-3-yl-methylamine L-Tartrate

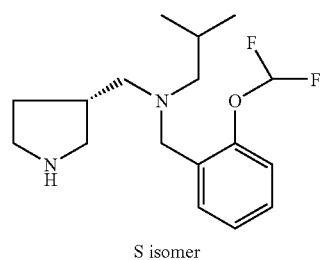

S isomer

Step i

N-(2-Methylpropyl)-1-tert-butyloxycarbonyl-(3R)-pyrrolidine-3-yl-methylamine A solution of (R)-3-(aminomethyl)-1-N-tert-butyloxycarbonylpyrrolidine (8.62 g, 42.3 mmol) and isobutyraldehyde (3.10 g, 42.3 mmol) in ethanol (100 ml) is stirred under an atmosphere of nitrogen at room temperature overnight. The reaction mixture is then cooled in an ice bath and sodium borohydride (3.20 g, 86.0 mmol) is added portionwise and the mixture stirred for 1.5 h at room temperature. The reaction mixture is concentrated and water added, extracted twice with diethyl ether. The extracts are washed with brine, dried over magnesium sulphate, filtered and evaporated to give the required product as a crude oil. The crude is purified using a combiflash on an ISCO silica cartridge (130 g) by gradient elution with dichloromethane-methanol (0 to 12% over 40 min) to give the required product as a colourless oil (9.59 g).

Step ii

N-{[2-Difluoromethoxyphenyl]methyl}-N-(2-methylpropyl)-1-tert-butyloxycarbonyl-(3R)-pyrrolidine-3-yl-methylamine To a stirred solution of N-(2-methylpropyl)-1-tert-butyloxycarbonyl-(3R)-pyrrolidine-3-yl-methylamine (312 mg, 1.22 mmol) and 2-(difluoromethoxy)benzaldehyde (419 mg, 2.43 mmol) in tetrahydrofuran (8 ml) is added sodium triacetoxyborohydride (644 mg, 3.05 mmol). After stirring for 3 days at room temperature, aqueous saturated sodium bicarbonate (15 ml) and dichloromethane (15 ml) are added, stirred for 5 min, then separated using a hydrophobic frit. The organic phase is evaporated and the resulting oil is dissolved in methanol and purified using a SCX-2 column (10 g), washed with methanol and the basic product eluted with methanolic ammonia (2M). Evaporate to give the required compound as a colourless oil.

Step iii

N-(2-Methylpropyl)-N-{[2-(difluoromethoxy)phenyl]methyl}-(3S)-pyrrolidine-3-yl-methylamine L-Tartrate A solution of N-{[2-difluoromethoxyphenyl]methyl}-N-(2-methylpropyl)-1-tert-butyloxycarbonyl-(3R)-pyrrolidine- 3-yl-methylamine (524 mg, 1.27 mmol) in dichloromethane (10 ml) is stirred at room temperature with trifluoroacetic acid (0.99 ml, 12.7 mmol) overnight. The reaction mixture is concentrated in vacuo and the oil dissolved in methanol and purified using a SCX-2 column (10 g), washed with methanol and the basic product eluted with methanolic ammonia (2M). Evaporate to an oil and the L-tartrate salt is isolated by freeze drying from acetonitrile-water to give a colourless solid (460 mg). $^1$H NMR (300 MHz, DMSO) $\delta_H$: 7.48-6.94 (5H, m), 3.91 (2H, m), 3.59-3.49 (2H, m), 3.29-3.23 (1H, m), 3.17-3.02 (2H, m), 2.73-2.67 (1H, m), 2.50-2.49 (1H, m), 2.46-2.34 (2H, m), 2.10 (2H, d), 2.04-1.93 (1H, m), 1.79-1.70 (1H, hept), 1.55-1.43 (1H, m), 0.80 (6H, d). LCMS: Rt=2.97 (12 min method) [M+H]=313.2.

EXAMPLE 46

N-(2-Methylpropyl)-N-{[2-(difluoromethoxy)phenyl]methyl}-(3R)-pyrrolidine-3-yl-methylamine L-Tartrate

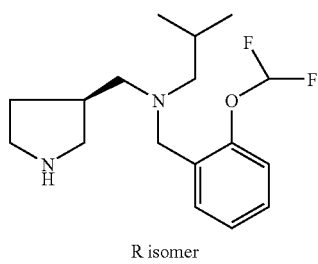

R isomer

The title compound is prepared starting from (S)-3-(aminomethyl)-1-N-tert-butyloxycarbonylpyrrolidine following the procedures described in Example 45. (450 mg). $^1$H NMR (300 MHz, DMSO) $\delta_H$: 7.48-6.94 (5H, m), 3.91 (2H, m), 3.59-3.49 (2H, m), 3.29-3.23 (1H, m), 3.17-3.02 (2H, m), 2.73-2.67 (1H, m), 2.50-2.49 (1H, m), 2.46-2.34 (2H, m), 2.10 (2H, d), 2.04-1.93 (1H, m), 1.79-1.70 (1H, hept), 1.55-1.43 (1H, m), 0.80 (6H, d). LCMS: Rt=2.95 (12 min method) [M+H]=313.2.

EXAMPLE 47

N-{[2,4-Dichlorophenyl]methyl}-N-(tetrahydrofuran-3S-yl)-(3S)-pyrrolidine-3-yl-methylamine L-Tartrate

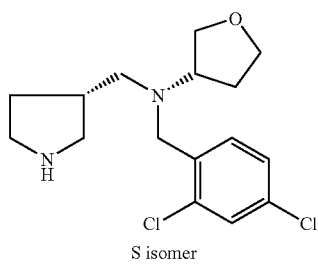

S isomer

Step (i)

N-(Tetrahydrofuran-3S-yl)-1-tert-butyloxycarbonyl-(3R)-pyrrolidine-3-yl-methylamine A solution of (R)-3-(aminomethyl)-1-N-tert-butyloxycarbonylpyrrolidine (702 mg, 3.50 mmol), (3R)-tetrahydrofuran-3-yl-4-methylbenzenesulphonate (849 mg, 3.50 mmol) and anhydrous potassium carbonate (846 mg, 6.12 mmol) in acetonitrile (15 ml) is heated at 90° C. for 3.5 days. The reaction mixture is cooled to room temperature, diluted with diethyl ether and filtered through celite. The filtrate is evaporated and the resulting oil purified using a combiflash on an ISCO silica cartridge (40 g) by gradient elution with dichloromethane-methanol (0 to 20% over 30 min). The required product is obtained as a colourless oil (596 mg).

Step (ii)

N-{[2,4-Dichlorophenyl]methyl}-N-(tetrahydrofuran-3S-yl)-1-tert-butyloxycarbonyl-(3R)-pyrrolidine-3-yl-methylamine To a stirred solution of N-(Tetrahydrofuran-3S-yl)-1-tert-butyloxycarbonyl-(3R)-pyrrolidine-3-yl-methylamine (138 mg, 0.51 mmol) and 2,4-dichlorobenzaldehyde (179 mg, 1.02 mmol) in tetrahydrofuran (4 ml) is added sodium triacetoxyborohydride (270 mg, 1.28 mmol). After stirring overnight at room temperature, aqueous sodium bicarbonate (10 ml) and dichloromethane (15 ml) is added, stirred for 5 min, then, separated using a hydrophobic frit. The organic phase is evaporated and the resulting oil is dissolved in methanol and purified using a SCX-2 column (10 g), washed with methanol and the basic product eluted with methanolic ammonia (2M). Evaporate to give the required compound as a colourless oil. (150 mg).

Step (iii)

N-{[2,4-Dichlorophenyl]methyl}-N-(tetrahydrofuran-3S-yl)-(3S)-pyrrolidine-3-yl-methylamine L-Tartrate A solution of N-{[2,4-Dichlorophenyl]methyl}-N-(tetrahydrofuran-3S-yl)-1-tert-butyloxycarbonyl-(3R)-pyrrolidine-3-yl-methylamine (150 mg, 0.35 mmol) in dichloromethane (10 ml) is stirred at room temperature with trifluoroacetic acid (0.4 g, 3.50 mmol) overnight. The reaction mixture is concentrated in vacuo and the oil dissolved in methanol and purified using a SCX-2 column (10 g), washed with methanol and the basic product eluted with methanolic ammonia (2M). The methanolic ammonia is evaporated and the resulting oil dissolved in acetonitrile, L-tartaric acid (1 eq) is added and then water to give a clear solution. Freeze dry to give the title compound as a colourless solid (170 mg). $^1$H NMR (300 MHz, DMSO) $\delta_H$: 7.57-7.52 (2H, m), 7.44-7.41 (1H, dd), 3.92 (2H, s), 3.88-3.72 (1H, m), 3.67-3.41 (6H, m), 3.21-3.03 (3H, m), 2.77-2.71 (1H, m), 2.50-2.49 (1H, m), 2.49-2.36 (2H, m), 1.96-1.81 (3H, m), 1.79-1.75 (1H, m), 1.53-1.46 (1H, m). LCMS: Rt=4.24 (12 min method) [M+H]=329/331.

EXAMPLE 48

N-{[3,5-Dichlorophenyl]methyl}-N-(tetrahydrofuran-3S-yl)-(3S)-pyrrolidine-3-yl-methylamine L-Tartrate

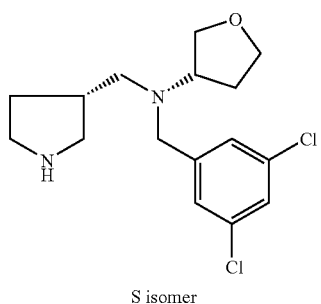

S isomer

The title compound is prepared following the procedures described in example 47 except 3,5-dichlorobenzaldehyde replaces 2,4-dichlorobenzaldehyde in step (ii). The tartrate salt is isolated by dissolving the free base in methanol. L-tartaric acid (1 eq) is added, the mixture heated to give a clear solution and then allowed to stand over a vapour of diethyl ether. The resulting crystals are filtered, washed with diethyl ether and dried in vacuo at 60° C. to give the title compound as a colourless solid (195 mg). $^1$H NMR (300 MHz, DMSO) $\delta_H$: 7.48 (1H, s), 7.35 (2H, s), 3.85 (2H, s), 3.85-3.77 (1H, m), 3.72-3.36 (4H, m), 3.25-3.00 (3H, m), 2.78-2.67 (1H, m), 2.53-2.34 (5H, m), 2.03-1.85 (2H, m), 1.83-1.68 (1H, m), 1.58-1.42 (1H, m). LCMS: Rt=4.40 (12 min method) [M+H]=329/331.

EXAMPLE 49

N-{[2,4-Dichlorophenyl]methyl}-N-(tetrahydrofuran-3R-yl)-(3S)-pyrrolidine-3-yl-methylamine L-Tartrate

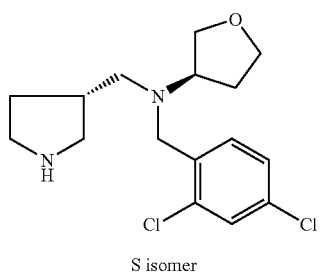

S isomer

The title compound is prepared following the procedures described in example 47 using (3S)-tetrahydrofuran-3-yl-4-methylbenzenesulphonate. The tartrate salt is isolated by dissolving the free base in methanol. L-tartaric acid (1 eq) is added, the mixture heated to give a clear solution and then allowed to stand over a vapour of diethyl ether. The resulting crystals are filtered, washed with diethyl ether and dried in vacuo at 60° C. to give the title compound as a colourless solid (598 mg). $^1$H NMR (300 MHz, DMSO) $\delta_H$: 7.57-7.52 (2H, m), 7.44-7.41 (1H, dd), 3.89 (2H, s), 3.85-3.81 (1H, m), 3.73-3.40 (6H, m), 3.22-3.00 (3H, m), 2.75-2.69 (1H, m), 2.50-2.49 (1H, m), 2.49-2.35 (2H, m), 1.94-1.80 (3H, m), 1.78-1.76 (1H, m), 1.52-1.45 (1H, m). LCMS: Rt=4.34 (12 min method) [M+H]=329/331.

EXAMPLE 50

N-{[3,5-Dichlorophenyl]methyl}-N-(tetrahydrofuran-3R-yl)-(3S)-pyrrolidine-3-yl-methylamine L-Tartrate

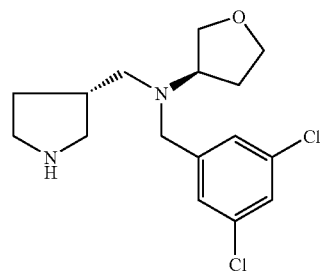

S isomer

The title compound is prepared following the procedures described in example 47 using (3S)-tetrahydrofuran-3-yl-4-methylbenzenesulphonate in step (i) and 3,5-dichlorobenzaldehyde in step (ii). The tartrate salt is isolated, by dissolving the free base in methanol. L-tartaric acid (1 eq) is added, the mixture heated to give a clear solution and then allowed to stand over a vapour of diethyl ether. The resulting crystals are filtered, washed with diethyl ether and dried in vacuo at 60° C. to give the title compound as a colourless solid (403 mg). $^1$H NMR (300 MHz, DMSO) $\delta_H$: 7.48 (1H, s), 7.35 (2H, s), 3.85 (2H, s), 3.85-3.77 (1H, m), 3.72-3.36 (4H, m), 3.25-3.00 (3H, m), 2.78-2.67 (1H, m), 2.53-2.34 (5H, m), 2.03-1.85 (2H, m), 1.83-1.68 (1H, m), 1.58-1.42 (1H, m). LCMS: Rt=4.40 (12 min method) [M+H]=329/331.

EXAMPLE 51

(3-endo)-N-(2,4-dichlorobenzyl)-N-[(3S)-pyrrolidin-3-ylmethyl]-8-oxabicyclo[3.2.1]octan-3-amine L-Tartrate

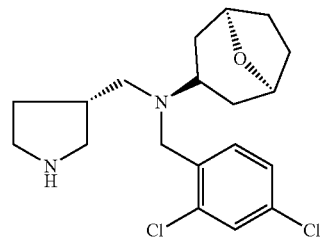

The title compound is prepared following the procedure described in example 1 using 8-oxabicyclo[3.2.1]octan-3-one except in step (i) the crude oil is purified using the combiflash on an Isco column by gradient elution with dichloromethane-methanol (0 to 15% over 35 min). In step (ii), tetrahydrofuran is used as the solvent. The tartrate salt is isolated by freeze drying from acetonitrile-water to give a colourless solid (645 mg). $^1$H NMR (300 MHz, DMSO) $\delta_H$: 7.58-7.51 (2H, m), 7.49-7.40 (1H, m), 4.30 (2H, brs), 3.80 (2H, s), 3.65 (2H, s), 3.21-3.0 (3H, m), 2.85-2.69 (2H, m), 2.56-2.41 (2H, m), 2.40-2.24 (1H, m), 2.20-2.10 (2H, m), 1.97-1.85 (1H, m), 1.84-1.75 (2H, m), 1.68-1.61 (2H, m), 1.60-1.48 (1H, m), 1.25-1.10 (2H, m). LCMS: Rt=2.96 (6 min method) [M+H]=369/371.

EXAMPLE 52

N-{[2,4-Dichlorophenyl]methyl}-N-(tetrahydrofuran-3S-yl)-(3R)-pyrrolidine-3-yl-methylamine L-Tartrate

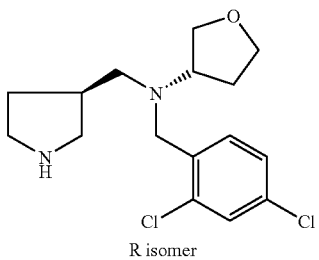

R isomer

The title compound is prepared following the procedure described in example 47, except in step (i), the reaction mixture is heated for 4.5 days and the tartrate salt crystallises as described in example 48 to give a colourless solid (360 mg). $^1$H NMR (300 MHz, DMSO) $\delta_H$: (2H, m), 7.57-7.52 (2H, m), 7.44-7.41 (1H, m), 3.88 (2H, s), 3.85-3.84 (1H, m), 3.73-3.32 (6H, m), 3.22-3.07 (3H, m), 2.76-2.73 (1H, m), 2.50 (1H, s), 2.43-2.38 (2H, m), 2.01-1.82 (2H, m), 1.80-1.72 (1H, m), 1.52-1.49 (1H, m). LCMS: Rt=4.33 (12 min method) [M+H]=329/331.

EXAMPLE 53

N-{[3,5-Dichlorophenyl]methyl}-N-(tetrahydrofuran-3S-yl)-(3R)-pyrrolidine-3-yl-methylamine L-Tartrate

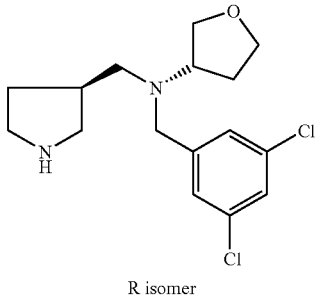

R isomer

The title compound is prepared following the procedure described in example 47, except in step (i), the reaction mixture is heated for 4.5 days. Step (ii) is carried out and the tartrate salt crystallises as described in example 48 to give a colourless solid (360 mg). $^1$H NMR (300 MHz, DMSO) $\delta_H$: 7.47 (1H, m), 7.35 (2H, s), 3.89 (2H, s), 3.87-3.80 (1H, m), 3.69-3.40 (6H, m), 3.23-3.01 (3H, m), 2.76-2.70 (1H, m), 2.50 (1H, s), 2.49-2.38 (3H, m), 1.98-1.89 (2H, m), 1.80-1.69 (1H, m), 1.58-1.48 (1H, m). LCMS: Rt=4.43 (12 min method) [M+H]=329/331.

EXAMPLE 54

N-{[2,4-Dichlorophenyl]methyl}-N-(tetrahydrofuran-3R-yl)-(3R)-pyrrolidine-3-yl-methylamine L-Tartrate

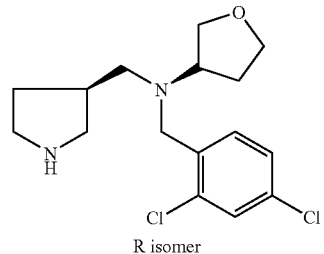

R isomer

The title compound is prepared following the procedure described in example 47, except in step (i), (3S)-tetrahydrofuran-3-yl-4-methylbenzenesulphonate is used, the reaction mixture is heated for 4.5 days and the chromatography eluent is dichloromethane-methanol (0 to 18% over 35 min). The tartrate salt crystallises as described in example 48 to give a colourless solid (340 mg). $^1$H NMR (300 MHz, DMSO) $\delta_H$: 7.57-7.53 (2H, m), 7.44-7.41 (1H, s), 3.89 (2H, s), 3.86-3.81 (1H, m), 3.77-3.32 (6H, m), 3.20-3.02 (3H, m), 2.77-2.71 (1H, m), 2.51-2.46 (3H, m), 2.41-2.33 (1H, m), 2.01-1.91 (2H, m), 1.84-1.72 (1H, m), 1.55-1.43 (1H, m). LCMS: Rt=4.34 (12 min method) [M+H]=329/331.

EXAMPLE 55

N-{[3,5-Dichlorophenyl]methyl}-N-(tetrahydrofuran-3R-yl)-(3R)-pyrrolidine-3-yl-methylamine L-Tartrate

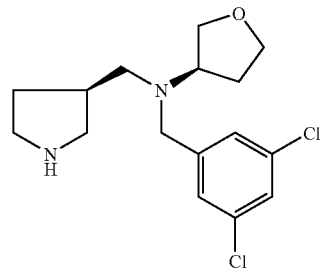

R isomer

The title compound is prepared following the procedure described in example 47, except in step (i), (3S)-tetrahydrofuran-3-yl-4-methylbenzenesulphonate is used and the chromatography eluent is dichloromethane-methanol (0 to 18% over 35 min), the reaction mixture is heated for 4.5 days. Step (ii) carried out and the tartrate salt crystallised as described in example 48 to give a colourless solid (310 mg). $^1$H NMR (300 MHz, DMSO) $\delta_H$: 7.47(1H, s), 7.35 (2H, s), 3.88 (2H, s), 3.87-3.80 (1H, m), 3.68-3.54 (5H, m), 3.51-3.34 (1H, m), 3.21-3.01 (3H, m), 2.77-2.71 (1H, m), 2.50 (1H, s), 2.49-2.40

(3H, m), 1.98-1.90 (2H, m), 1.80-1.69 (1H, m), 1.56-1.49 (1H, m). LCMS: Rt=4.41 (12 min method) [M+H]=329/331.

EXAMPLE 56

(3-endo)-N-(2,4-dichlorobenzyl)-N-[(3R)-pyrrolidin-3-ylmethyl]-8-oxabicyclo[3.2.1]octan-3-amine L-Tartrate

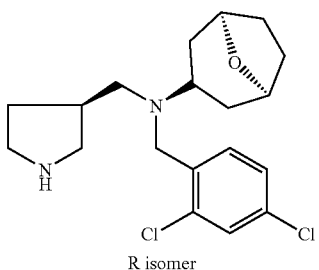

R isomer

The title compound is prepared following the procedure described in example 1 using 8-oxabicyclo[3.2.1]octan-3-one except in step (i) the crude oil is purified using the combiflash on an Isco column by gradient elution with dichloromethane-methanol (0 to 15% over 35 min). In step (ii), tetrahydrofuran is used as the solvent. The tartrate salt is obtained as a colourless foam by evaporation of a solution in methanol (467 mg). $^1$H NMR (300 MHz, DMSO) $\delta_H$: 7.58-7.51 (2H, m), 7.49-7.40 (1H, m), 4.30 (2H, brs), 3.80 (2H, s), 3.65 (2H, s), 3.21-3.0 (3H, m), 2.85-2.69 (2H, m), 2.56-2.41 (2H, m), 2.40-2.24 (1H, m), 2.20-2.10 (2H, m), 1.97-1.85 (1H, m), 1.84-1.75 (2H, m), 1.68-1.61 (2H, m), 1.60-1.48 (1H, m), 1.25-1.10 (2H, m). LCMS: Rt=4.64 (12 min method) [M+H]=369/371.

EXAMPLE 57

N-(2-Methylpropyl)-N-{[3,5-dichlorophenyl]-methyl}-(2S)-pyrrolidine-2-yl-methylamine L-Tartrate

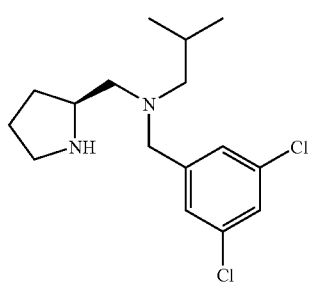

(i) Sodium triacetoxyborohydride (2.9 g, 14 mmol, 1.4 eq) is added to a solution of isobutylamine (0.77 g, 10 mmol, 1.05 eq) and N-(tert-butoxycarbonyl)-L-prolinal (2 g, 10 mmol, 1 eq) in 1,2-dichloroethane (35 ml). After 1 hr water (25 ml) followed by 2N aqueous sodium hydroxide (25 ml) is added. The aqueous layer is separated and extracted with dichloromethane (3×50 ml). The organic layers are combined and dried over magnesium sulphate, filtered, and concentrated in vacuo giving a residue. The residue is purified by flash chromatography, eluting with 20-70% methanol in ethyl acetate to give the tert-butyl (2S)-2-[(isobutylamino)methyl]pyrrolidine-1-carboxylate (1.95 g, 76%): $^1$H NMR (300 MHz, CDCl$_3$) $\delta_H$: 3.69-4.07 (1H, m), 3.19-3.50 (2H, m), 2.67-2.87 (1H, m), 2.48-2.65 (1H, m), 2.35-2.47 (2H, m), 1.62-2.01 (5H, m), 1.34-1.53 (9H, m) and 0.88 (6H, d); LCMS: Rt=2.74 (6 min method) [M+H]=257.5.

(ii) A solution of 3,5-dichlorobenzaldehyde (0.79 g, 4.5 mmol, 3 eq) in 1,2-dichloroethane (2 ml) is added to a solution of tert-butyl (2S)-2-[(isobutylamino)methyl]pyrrolidine-1-carboxylate (0.38 g, 1.5 mmol, 1 eq) in 1,2-dichloroethane (8 ml) followed by a solution of sodium triacetoxyborohydride (0.95 g, 4.5 mmol, 3 eq) in DMF (2 ml). After 16 hrs water (5 ml) followed by 2N aqueous sodium hydroxide (5 ml) is added. The biphasic mixture is passed through a hydrophobic frit to separate the organic layer. Methanol is added to the organic layer and the solution is loaded onto a SCX-2 (10 g) column. The column is washed with methanol (50 ml) and then the basic material is eluted with 2M ammonia in methanol (50 ml). The solvent is removed in vacuo to give the tert-butyl (2S)-2-{[(3,5-dichlorobenzyl)(isobutyl)amino]methyl}pyrrolidine-1-carboxylate (0.61 g, 98%). LCMS: Rt=4.17 (6 min method) [M+H]=415.4.

(iii) Trifluoroacetic acid (1.5 ml, 15 mol, 10 eq) is added to a solution of tert-butyl (2S)-2-{[(3,5-dichlorobenzyl)(isobutyl)amino]methyl}pyrrolidine-1-carboxylate (0.611 g, 1.5 mmol, 1 eq) in dichloromethane (5 ml). After 16 hours if not complete by LCMS add an additional portion of trifluoroacetic acid (1.5 ml, 15 mol, 10 eq). After 72 hrs the solvent is removed in vacuo, methanol is added to the residue and the solution is loaded onto a SCX-2 (5 g) column. The column is washed with methanol (10 ml) and then the basic material is eluted with 2M ammonia in methanol (10 ml) and the solvent is removed in vacuo. The residue is dissolved in isopropanol (5 ml) and L-tartaric acid (1 eq) is added. The solution is heated to dissolve, then cooled and is left to stand in a fridge for 2 hrs, if no crystals have formed cyclohexane is added and the surface is scratched with a glass rod. The solid formed is filtered and dried in a vacuum oven at 60° C. for 16 hrs to give the N-(2-methylpropyl)-N-{[3,5-dichlorophenyl]-methyl}-(2S)-pyrrolidine-2-yl-methylamine L-Tartrate (0.23 g, 33%). $^1$H NMR (300 MHz, CD3OH) $\delta_H$: 7.26 (3H, s) 4.29 (2H, s, tartrate) 3.44-3.78 (3H, m) 3.06-3.30 (4H, m) 2.42-2.71 (2H, m) 2.00-2.19 (3H, m) 1.83-1.99 (2H, m) 1.65-1.81 (1H, m) 1.46-1.64 (1H, m) 0.79 (6H, dd, J=6.5 and 3.2), LCMS: Rt=3.52 (12 min method) [M+H]=315.4.

EXAMPLE 58

N-(2-Methylpropyl)-N-{[3,5-dichlorophenyl]-methyl}-(3R)-piperidine-3-yl-methylamine 1.5 L-Tartrate

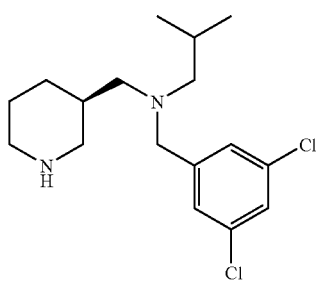

(i) Borane-tetrahydrofuran complex (1M in THF) (65.4 ml, 65.4 mmol, 3 eq) is added dropwise to a solution of (R)-(−)-

N-Boc-nipecotic acid (5 g, 21.8 mmol, 1 eq) in THF (50 ml) and this is stirred at room temperature for 16 hours. The solution is cooled to 0° C. and carefully hydrolysed with 2N aqueous sodium hydroxide (250 ml) the resulting mixture is then heated for 48 hrs. The mixture is cooled to 0° C. and extracted with diethyl ether (3×100 ml). The organic layers are combined, washed with brine (100 ml), dried over magnesium sulphate, filtered and concentrated in vacuo. The residue is purified by flash chromatography, eluting with 50-70% ethyl acetate in iso-hexane to give the tert-butyl (3R)-3-(hydroxymethyl)piperidine-1-carboxylate (4.56 g, 98%). $^1$H NMR (300 MHz, CDCl$_3$) $\delta_H$: 4.0-2.7 (6H, br m), 2.17-1.19 (5H, br m) 1.46 (9H, s).

(ii) DMSO (3.3 ml, 46.6 mmol, 2.2 eq) in dichloromethane (20 ml) is added dropwise to a solution of oxalyl chloride (2.03 ml, 23.2 mmol, 1.1 eq) in dichloromethane (80 ml) cooled to –78° C. This mixture is stirred for 10 mins and then tert-butyl (3R)-3-(hydroxymethyl)piperidine-1-carboxylate (4.56 g, 21.1 mmol, 1 eq) in dichloromethane (20 ml) is added dropwise. This is stirred for 20 mins and then triethylamine (15.0 ml, 105 mmol, 5 eq) is added in one portion and then warmed to room temperature over 30 mins. The solution is poured onto diethyl ether (300 ml) and brine (300 ml), separated and the aqueous layer is extracted with diethyl ether (2×100 ml). The organic layers are combined, washed with brine (100 ml), dried over magnesium sulphate, filtered and concentrated in vacuo to give tert-butyl (3R)-3-formylpiperidine-1-carboxylate (4.33 g, 96%) $^1$H NMR (300 MHz, CDCl$_3$) $\delta_H$ 9.63 (1H, s), 3.75-3.98 (1H, m), 3.48-3.66 (1H, m), 3.16-3.34 (1H, m), 2.90-3.11 (1H, m), 2.26-2.44 (1H, m), 1.79-1.97 (1H, m), 1.53-1.70 (2H, m) and 1.20-1.49 (10H, m).

(iii) tert-butyl (3R)-3-formylpiperidine-1-carboxylate is treated as described in example 57 (i) to give tert-butyl (3S)-3-[(isobutylamino)methyl]piperidine-1-carboxylate. $^1$H NMR (300 MHz, CDCl$_3$) $\delta_H$: 3.75-4.00 (2H, m), 2.79-2.92 (1H, m), 2.55-2.68 (1H, m) 2.31-2.53 (4H, m), 1.45-1.90 (5H, m), 1.45 (9H, s), 1.05-1.30 (1H, m) and 0.90 (6 H, d, J=6.78Hz). LCMS: Rt=2.52 (6 min method) [M+H]=271.5.

(iv) tert-butyl (3S)-3-[(isobutylamino)methyl]piperidine-1-carboxylate is treated as described in example 57 (ii) The crude residue is purified by flash chromatography, eluting with 0-40% ethyl acetate in iso-hexane to give tert-butyl (3S)-3-{[(3,5-dichlorobenzyl)(isobutyl)amino] methyl}piperidine-1-carboxylate. LCMS: Rt=5.89 (6 min method) [M+H]=429.4.

(v) Trifluoroacetic acid (3.0 ml, 30 mol, 23 eq) is added to a solution of tert-butyl (3S)-3-{[(3,5-dichlorobenzyl)(isobutyl)amino]methyl}piperidine-1-carboxylate (0.574 g, 1.3 mmol, 1 eq) in dichloromethane (5 ml). After 16 hours the solvent is removed in vacuo, methanol is added to the residue and the solution is loaded onto a SCX-2 (5 g) column. The column is washed with methanol (10 ml) and then the basic material is eluted with 2M ammonia in methanol (10 ml) and the solvent is removed in vacuo. The residue is dissolved in isopropanol (5 ml) and L-tartaric acid (1 eq) is added. The crystals formed are filtered and dried in a vacuum oven at 60° C. for 16 hrs to give the title product (0.33 g, 46%). $^1$H NMR (300 MHz, MeOH) $\delta_H$: 7.05-7.27 (3H, m), 4.34 (3H, s, tartrate), 3.52 (1H, d, J=14.13 Hz), 3.38 (1H, d, J=13.00 Hz), 3.28 (1H, d, J=14.32 Hz), 2.66-2.81 (1 H, m), 2.38 (1H, t, J=11.96 Hz), 2.17 (2H, d, J=6.97 Hz), 2.04 (2H, d, J=7.16 Hz), 1.48-1.99 (5H, m), 0.90-1.11 (2H, m) and 0.80 (6H, t, J=6.03 Hz). LCMS: Rt=5.51 (12 min method) [M+H]=329.1.

EXAMPLE 59

N-(2-Methylpropyl)-N-{[2-chlorophenyl]-methyl}-piperidine-4-yl-methylamine L-Tartrate

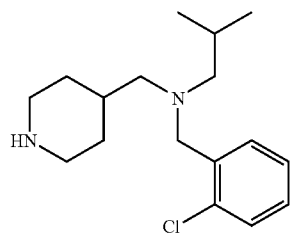

(i) To a round bottom flask (50 mL) under nitrogen with stirring, is added N-Boc-4-(aminomethyl)-piperidine (0.500 g, 2.33 mmol), 2-chlorobenzaldehyde (0.275 mL, 0.344 g, 2.45 mmol) and sodium triacetoxyborohydride (1.483 g, 6.99 mmol) to dichloroethane (20 mL) and dimethylformamide (3 mL). Reaction is allowed to stir for 2 days. TLC (10% MeOH/DCM; starting material r.f 0.1, product r.f. 0.6). Reaction is then poured onto saturated potassium carbonate (c.a. 80 mL) and the product is extracted with ethyl acetate (c.a. 100 mL). This is dried over magnesium sulphate and concentrated in vacuo. The residue is taken up in methanol and placed on a 10 g SCX-2 column and washed with methanol. The product is eluted with 3.5M ammonia in methanol solution. The resultant solution is concentrated in vacuo to afford the N-Boc-4-(2-chlorobenzylaminomethyl)piperidine as a colourless oil (0.677 g, 86%).

(ii) To a round bottom flask (50 mL) under nitrogen with stirring, is added N-Boc-4-(2-chlorobenzylaminomethyl)piperidine (0.677 g, 1.988 mmol), isobutyraldehyde (0.192 mL, 0.151 g, 2.09 mmol) and sodium triacetoxyborohydride (1.27 g, 5.99 mmol) to dichloroethane (15 mL) and dimethylformamide (2 mL). Reaction is allowed to stir for 20 hours. TLC (10% MeOH/DCM; starting material r.f 0.6, product r.f. 0.9). Reaction is then poured onto saturated potassium carbonate (c.a. 80 mL) and product extracted with ethyl acetate (c.a. 80 mL). The residue is dried over magnesium sulphate and concentrated in vacuo. This is taken up in methanol and placed on a 10 g SCX-2 column and washed with methanol. The product is eluted with 3.5M ammonia in methanol solution. The resultant solution is concentrated in vacuo to afford the N-(2-methylpropyl)-N-{[2-chlorophenyl]-methyl}-piperidine-4-yl-methylamine N-tert-butylcarboxylate as a colourless oil (0.764 g, 97%).

(iii) To a round bottom flask (50 mL) is added N-(2-methylpropyl)-N-{[2-chlorophenyl]-methyl}-piperidine-4-yl-methylamine N-tert-butylcarboxylate (0.764 g, 1.93 mmol), anisole (c.a. 3.0 mL), and trifluoroacetic acid (3.0 mL) to dichloromethane (8.0 mL). Reaction is allowed to stir for 1 hour. TLC (100% ethyl acetate; starting material r.f 0.8, product r.f. 0.0). The reaction is then concentrated in vacuo, taken up in methanol, placed on a 10 g SCX-2 column and washed with methanol. The product is eluted with 3.5M ammonia in methanol solution. The resultant solution is concentrated in vacuo to afford the N-(2-Methylpropyl)-N-{[2-chlorophenyl]-methyl}-piperidine-4-yl-methylamine as a colourless oil (0.517 g, 91%). This is purified by prep LCMS, the resultant clean product is taken up in methanol and placed on a 10 g SCX-2 column. The product is eluted with 3.5M ammonia in methanol solution to afford a colourless oil (0.369 g, 1.25 mmol). This is dissolved in aqueous acetonitrile, and L-tartaric acid (0.188 g, 1.25 mmol) added. This is sonicated until the acid dissolves, at this point the solution is cooled to −80° C. until frozen and placed on the freeze drier to afford the title product as a white solid (0.557 g, 1.25 mmol). $^1$H NMR (300 MHz, d6-DMSO) $\delta_H$: 7.50 (d, 1H), 7.40 (d, 1H), 7.25 (m, 2H), 3.80 (s, 2H), 3.55 (s, 2H), 3.20 (d, 2H), 2.78 (t, 2H), 2.20 (d, 2H), 2.10 (d, 2H), 1.90-1.60 (m, 4H), 1.20-1.00 (m, 2H), 0.80 (d, 6H). LCMS: Rt=3.25 mins (12 min method) [M+H]=295/297.

EXAMPLE 60

N-(3-Hydroxy-3-methylbutyl)-N-{[2,4-dichlorophenyl]-methyl}-azetidine-3-yl-methylamine L-Tartrate

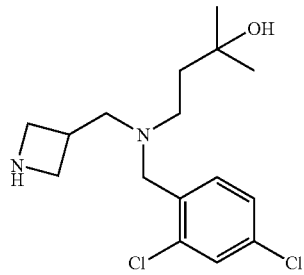

(i) To a solution of 3-aminomethyl-azetidine-1-carboxylic acid tert-butyl ester (300 mg, 1.6 mmol), 2,4-dichlorobenzaldehyde (281 mg, 1.61 mmol) and acetic acid (0.09 mL, 1.61 mmol) in 1,2-dichloroethane (16 mL) at 0° C. is added sodium triacetoxy-borohydride (476 mg, 2.25 mmol). The reaction is warmed to ambient temperature and stirred overnight under $N_2$. The reaction mixture is poured on to 2N NaOH (20 mL) and extracted with ethyl acetate (3×). The combined organic extracts are washed with aqueous saturated NaCl, dried ($Na_2SO_4$), filtered and concentrated. The crude product is purified by flash chromatography on silica gel eluting with 5% EtOH (10% $NH_4OH$)/chloroform to yield 360 mg (65%) of 3-[(2,4-dichlorobenzylamino)-methyl]-azetidine-1-carboxylic acid tert-butyl ester. $^1$H NMR (400 MHz, $CD_3OD$) $\delta_H$: 7.49-7.47 (2H, m), 7.36-7.34 (1H, m), 4.05-4.01 (2H, m), 3.88 (2H, s), 3.64-3.61 (2H, m), 2.8 (2H, m), 2.78-2.74 (1H, m), 1.46 (9H, s). Mass spectrum (ion spray): m/z=345.1 (M+H).

(ii) To a solution of 3-[(2,4-dichlorobenzylamino)-methyl]-azetidine-1-carboxylic acid tert-butyl ester (200 mg, 0.58 mmol) in $CHCl_3$ (3 mL) is added methyl vinyl ketone (0.12 mL, 1.45 mmol). The reaction is refluxed under $N_2$ overnight and concentrated. The crude product is purified by flash chromatography on silica gel eluting with 5% EtOH (10% $NH_4OH$)/chloroform to yield 196 mg (81%) of 3-{[(2,4-dichlorobenzyl)-(3-oxo-butyl)-amino]-methyl}-azetidine-1-carboxylic acid tert-butyl ester. $^1$H NMR (400 MHz, $CD_3OD$) $\delta_H$: 7.46-7.44 (2H, m), 7.35-7.32 (1H, m), 3.95-3.91 (2H, m), 3.7 (2H, s) 3.5-3.45 (2H, m), 2.9-2.75 (3H, m), 2.74-2.65 (4H, m), 2.1 (3H, s), 1.46 (9H, s). Mass spectrum (ion spray): m/z=415.2 (M+H).

(iii) To a solution of 3-{[(2,4-dichlorobenzyl)-(3-oxo-butyl)-amino]-methyl}-azetidine-1-carboxylic acid tert-butyl ester (190 mg, 0.46 mmol) in $Et_2O$ (4 mL) is added MeMgBr (3.0 M in $Et_2O$, 0.92 mmol). The resulting mixture is stirred at room temperature for one hour. The reaction is quenched with saturated ammonium chloride and extracted with EtOAc (3×). The combined organic extracts are dried ($Na_2SO_4$), filtered and concentrated. The crude product is purified by flash chromatography on silica gel eluting with 5% EtOH (10% $NH_4OH$)/chloroform to yield 138 mg (70%) of 3-{[(2,4-dichlorobenzyl)-(3-hydroxy-3-methyl-butyl)-amino]-methyl}-azetidine-1-carboxylic acid tert-butyl ester. $^1$H NMR (400 MHz, $CD_3OD$) $\delta_H$: 7.49-7.47 (2H, m), 7.36-7.34 (1H, m), 4.0-3.96 (2H, m), 3.67 (2H, s), 3.57-3.53 (2H, m), 2.9-2.82 (1H, m), 2.75-2.73 (2H, m), 2.67 (2H, t, J=7.0 Hz), 1.69 (2H, t, J=7.3 Hz), 1.46 (9H, s), 1.1 (6H, s). Mass spectrum (ion spray): m/z=431.2 (M+H).

(iv) 3-{[(2,4-dichlorobenzyl)-(3-hydroxy-3-methyl-butyl)-amino]-methyl}-azetidine-1-carboxylic acid tert-butyl ester (88 mg, 0.2 mmol) is added to a stirred solution of dichloromethane (1.0 mL) and anisole (1.5 mL). Trifluoroacetic acid (0.6 mL) is added and the reaction is stirred for 2 h at room temperature. The reaction is concentrated to half volume and loaded onto a SCX-2 (10 g) column and washed with methanol (40 mL). The product is then eluted with 2M ammonia in methanol (25 mL) and concentrated to yield (57 mg, 87%) of N-(3-hydroxy-3-methylbutyl)-N-{[2,4-dichlorophenyl]-methyl}-azetidine-3-yl-methylamine. $^1$H NMR (400 MHz, $CD_3OD$) $\delta_H$: 7.49-7.47 (2H, m), 7.36-7.33 (1H, m), 3.80-3.70 (2H, m), 3.65 (2H, s), 3.49-3.40 (2H, m), 3.16-3.06 (1H, m), 2.79-2.77 (2H, m), 2.67 (2H, t, J=7.3 Hz), 1.69 (2H, t, J=7.3 Hz), 1.1 (6H, s). Mass spectrum (ion spray): m/z=331.2 (M+H).

(v) L-Tartaric acid (31.2 mg, 0.208 mmol) is added to a solution of N-(3-hydroxy-3-methylbutyl)-N-{[2,4-dichlorophenyl]-methyl}-azetidine-3-yl-methylamine (69 mg, 0.208 mmol) in methanol (2 mL). The solution is stirred for 1.5 h at ambient temperature and concentrated. The solid is dried in a vacuum oven at 45° C. overnight to yield (92 mg, 92%) of the title product. $^1$H NMR (400 MHz, $CD_3OD$) $\delta_H$: 7.50-7.48 (2H, m), 7.37-7.35 (1H, m), 4.5 (2H, s), 4.13-4.08 (2H, m), 3.81-3.76 (2H, m), 3.69 (2H, s), 3.25-3.20 (1H, m), 2.84-2.82 (2H, m), 2.67 (2H, t, J=7.5 Hz), 1.70 (2H, t, J=7.3 Hz), 1.1 (6H, s). Mass spectrum (ion spray): m/z=331.2 (M+H). LCMS: Rt=0.61 (3 min method).

The compounds of the present invention are inhibitors of the uptake of one or more, monoamines selected from serotonin, norepinephrine and dopamine. They work by selectively inhibiting one or more of the biogenic amine (serotonin, norepinephrine and dopamine) transporter proteins. Their selectivity profiles may be determined using the assays described below (see also J. Gobel, D. L. Saussy and A. Goetz, J. Pharmacol. Toxicolo. (1999), 42, 237-244). Compounds of formula (I) and their pharmaceutically acceptable salts preferably exhibit a $K_i$ value less than 500 nM at one or more of these monoamine transporter proteins as determined using the scintillation proximity assay as described below. The compounds of formula (I) exemplified above and their pharmaceutically acceptable salts exhibit a $K_i$ value less than 100 nM at one or more of these monoamine transporter proteins as determined using the assays described below. Preferred compounds of formula (I) and their pharmaceutically acceptable salts exhibit a $K_i$ value less than 50 nM at one or more of these monoamine transporter proteins. Especially preferred compounds of formula (I) and their pharmaceutically acceptable salts exhibit a $K_i$ value less than 20 nM at one or more of these monoamine transporter proteins. Preferably, compounds of the present invention which selectively inhibit one of the three biogenic amine transporters do so relative to the other two transporters by a factor of at least five, more preferably by a factor of at least ten. Preferably, compounds of the present invention which selectively inhibit two of the three biogenic amine transporters do so relative to the other transporter by a factor of at least five, more preferably by a factor of at least ten.

Biogenic amine transporters control the amount of neurotransmitters in the synaptic cleft. Inhibition of the respective transporter leads to a rise in that neurotransmitter. Inhibition of the individual transporters can be studied by a simple competitive binding assay using selective radioligands for the individual expressed human transporter site. Compounds may be compared for selectivity and potency on the human norepinephrine transporter (hNET), the h-serotonin transporter (hSERT) and the h-dopamine transporter (hDAT) using membranes prepared from HEK293 cells expressing the respective transporter site.

Advantageously, the compounds of the present invention also have a reduced interaction (both as substrate and inhibitor) with the liver enzyme Cytochrome P450 (CYP2D6). That is to say, they preferably exhibit less than 75% metabolism via the CYP2D6 pathway according to the CYP2D6 substrate assay described below and they preferably exhibit an IC50 of >6 µM according to the CYP2D6 inhibitor assay described below.

Generation of Stable Cell-Lines Expressing the Human Dopamine, Norepinephrine and Serotonin Transporters Standard molecular cloning techniques are used to generate stable cell-lines expressing the human dopamine, norepinephrine and serotonin transporters. The polymerase chain reaction (PCR) is used in order to isolate and amplify each of the three full-length cDNAs from an appropriate cDNA library. Primers for PCR are designed using the following published sequence data:

Human dopamine transporter: GenBank M95167. Reference: Vandenbergh D J, Persico A M and Uhl G R. *A human dopamine transporter cDNA predicts reduced glycosylation, displays a novel repetitive element and provides racially-dimorphic TaqI RFLPs*. Molecular Brain Research (1992) volume 15, pages 161-166.

Human norepinephrine transporter: GenBank M65105. Reference: Pacholczyk T, Blakely, R D and Amara S G. *Expression cloning of a cocaine- and antidepressant-sensitive human noradrenaline transporter*. Nature (1991) volume 350, pages 350-354.

Human serotonin transporter: GenBank L05568. Reference: Ramamoorthy S, Bauman A L, Moore K R, Han H, Yang-Feng T, Chang A S, Ganapathy V and Blakely R D. *Antidepressant- and cocaine-sensitive human serotonin transporter: Molecular cloning, expression, and chromosomal localization*. Proceedings of the National Academy of Sciences of the USA (1993) volume 90, pages 2542-2546.

The PCR products are cloned into a mammalian expression vector (eg pcDNA3.1 (Invitrogen)) using standard ligation techniques. The constructs are then used to stably transfect HEK293 cells using a commercially available lipofection reagent (Lipofectamine™-Invitrogen) following the manufacture's protocol.

Norepinephrine Binding Assay

The ability of compounds to compete with [$^3$H]-Nisoxetine for its binding sites on cloned human norepinephrine membranes is used as a measure of its ability to block norepinephrine uptake via its specific transporter.

Membrane Preparation:

Cell pastes from large scale production of HEK-293 cells expressing cloned human noradrenaline transporters are homogenised in 4 volumes 50 mM Tris.HCl containing 300 mM NaCl and 5 mM KCl, pH 7.4. The homogenate is centrifuged twice (40,000 g, 10 min, 4° C.) with pellet re-suspension in 4 volumes Tris.HCl buffer after the first spin and 8 volumes after the second spin. The suspended homogenate is centrifuged (100 g, 10 min, 4° C.) and the supernatant kept and re-centrifuged (40,000 g, 20 min, 4° C.). The pellet is resuspended in Tris.HCl buffer containing the above reagents along with 10% w/v sucrose and 0.1 mM phenylmethylsulfonyl fluoride (PMSF). The membrane preparation is stored in aliquots (1 ml) at −80° C. until required. The protein concentration of the membrane preparation is determined using a bicinchoninic acid (BCA) protein assay reagent kit (available from Pierce).

[$^3$H]-Nisoxetine Binding Assay:

Each well of a 96well microtitre plate is set up to contain the following:

| | |
|---|---|
| 50 µl | 2 nM [N-methyl-$^3$H]-Nisoxetine hydrochloride (70-87 Ci/mmol, from NEN Life Science Products) |
| 75 µl | Assay buffer (50 mM Tris.HCl pH 7.4 containing 300 mM NaCl and 5 mM KCl) |
| 25 µl | Test compound, assay buffer (total binding) or 10 µM Desipramine HCl (non-specific binding) |
| 50 µl | Wheatgerm agglutinin coated poly(vinyltoluene) (WGA PVT) SPA Beads (Amersham Biosciences RPNQ0001) (10 mg/ml) |
| 50 µl | Membrane (0.2 mg protein per ml.) |

The microtitre plates are incubated at room temperature for 10 hours prior to reading in a Trilux scintillation counter. The results are analysed using an automatic spline fitting programme (Multicalc, Packard, Milton Keynes, UK) to provide Ki values for each of the test compounds.

Serotonin Binding Assay

The ability of a test compound to compete with [$^3$H]-citalopram from its binding sites on cloned human serotonin membranes is used as a measure of its ability to block serotonin uptake via its specific transporter (Ramamoorthy, S., Giovanetti, E., Qian, Y., Blakely, R., (1998) J. Biol. Chem. 273,2458).

Membrane Preparation:

The preparation of membrane is essentially similar to that for the norepinephrine transporter containing membrane described above. The membrane preparation is stored in aliquots (1 ml) at −70° C. until required. The protein concentration of the membrane preparation is determined using BCA protein assay reagent kit.

[$^3$H]-Citalopram Binding Assay:

Each well of a 96well microtitre plate is set up to contain the following:

| | |
|---|---|
| 50 µl | 2 nM [$^3$H]-Citalopram (60-86 Ci/mmol, Amersham Biosciences) |
| 75 µl | Assay buffer (50 mM Tris.HCl pH 7.4 containing 150 mM NaCl and 5 mM KCl) |
| 25 µl | Diluted compound, assay buffer (total binding) or 100 µM Fluoxetine (non-specific binding) |
| 50 µl | WGA PVT SPA Beads (40 mg/ml) |
| 50 µl | Membrane preparation (0.4 mg protein per ml) |

The microtitre plates are incubated at room temperature for 10 hours prior to reading in a Trilux scintillation counter. The results are analysed using an automatic spline fitting programme (Multicalc, Packard, Milton Keynes, UK) to provide Ki (nM) values for each of the test compounds.

Dopamine Binding Assay

The ability to compete with [$^3$H]-WIN35,428 for its binding sites on human cell membranes containing cloned human dopamine transporter is used as a measure of its ability to block dopamine uptake via its specific transporter (Ramamoorthy et al 1998 supra).

Membrane Preparation:

Is essentially the same as for membranes containing cloned human serotonin transporter as described above.

[$^3$H]-WIN35,428 Binding Assay:

Each well of a 96well microtitre plate is set up to contain the following:

| | |
|---|---|
| 50 μl | 4 nM [$^3$H]-WIN35,428428 (84-87 Ci/mmol, from NEN Life Science Products) |
| 75 μl | Assay buffer (50 mM Tris.HCl pH 7.4 containing 150 mM NaCl and 5 mM KCl) |
| 25 μl | Diluted compound, assay buffer (total binding) or 100 μM Nomifensine (non-specific binding) |
| 50 μl | WGA PVT SPA Beads (10 mg/ml) |
| 50 μl | Membrane preparation (0.2 mg protein per ml.) |

The microtitre plates are incubated at room temperature for 120 minutes prior to reading in a Trilux scintillation counter. The results are analysed using an automatic spline fitting programme (Multicalc, Packard, Milton Keynes, UK) to provide Ki values for each of the test compounds.

CYP2D6 Assays

Cytochrome P450 2D6 (CYP2D6) is a mammalian enzyme which is commonly associated with the metabolism of around 30% of pharmaceutical compounds. Moreover, this enzyme exhibits genetic polymorphism, resulting in the presence of both normal and poor metabolizers in the population. A low involvement of CYP2D6 in the metabolism of compounds (i.e. the compound being a poor substrate of CYP2D6) is desirable in order to reduce any variability from subject to subject in the pharmacokinetics of the compound. Also, compounds with a low inhibitor potential for CYP2D6 are desirable in order to avoid drug-drug interactions with co-administered drugs that are substrates of CYP2D6. Compounds may be tested both as substrates and as inhibitors of this enzyme by means of the following assays.

CYP2D6 Substrate Assay

Principle:

This assay determines the extent of the CYP2D6 enzyme involvement in the total oxidative metabolism of a compound in microsomes. Preferred compounds of the present invention exhibit less than 75% total metabolism via the CYP2D6 pathway.

For this in vitro assay, the extent of oxidative metabolism in human liver microsomes (HLM) is determined after a 30 minute incubation in the absence and presence of Quinidine, a specific chemical inhibitor of CYP2D6. The difference in the extent of metabolism in absence and presence of the inhibitor indicates the involvement of CYP2D6 in the metabolism of the compound.

Materials and Methods:

Human liver microsomes (mixture of 20 different donors, mixed gender) are acquired from Human Biologics (Scottsdale, Ariz., USA). Quinidine and β-NADPH (β-Nicotinamide Adenine Dinucleotide Phosphate, reduced form, tetrasodium salt) are purchased from Sigma (St Louis, Mo., USA). All the other reagents and solvents are of analytical grade. A stock solution of the new chemical entity (NCE) is prepared in a mixture of Acetonitrile/Water to reach a final concentration of acetonitrile in the incubation below 0.5%.

The microsomal incubation mixture (total volume 0.1 mL) contains the NCE (4 μM), β-NADPH (1 mM), microsomal proteins (0.5 mg/mL), and Quinidine (0 or 2 μM) in 100 mM sodium phosphate buffer pH 7.4. The mixture is incubated for 30 minutes at 37° C. in a shaking waterbath. The reaction is terminated by the addition of acetonitrile (75 μL). The samples are vortexed and the denaturated proteins are removed by centrifugation. The amount of NCE in the supernatant is analyzed by liquid chromatography/mass spectrometry (LC/MS) after addition of an internal standard. A sample is also taken at the start of the incubation (t=0), and analysed similarly.

Analysis of the NCE is performed by liquid chromatography/mass spectrometry. Ten μL of diluted samples (20 fold dilution in the mobile phase) are injected onto a Spherisorb CN Column, 5 μM and 2.1 mm×100 mm (Waters corp. Milford, Mass., USA). The mobile phase consisting of a mixture of Solvent A/Solvent B, 30/70 (v/v) is pumped (Alliance 2795, Waters corp. Milford, Mass., USA) through the column at a flow rate of 0.2 ml/minute. Solvent A and Solvent B are a mixture of ammonium formate $5.10^{-3}$ M pH 4.5/methanol in the proportions 95/5 (v/v) and 10/90 (v/v), for solvent A and solvent B, respectively. The NCE and the internal standard are quantified by monitoring their molecular ion using a mass spectrometer ZMD or ZQ (Waters-Micromass Corp, Manchester, UK) operated in a positive electrospray ionisation.

The extent of CYP2D6 involvement (% of CYP2D6 involvement) is calculated comparing the extent of metabolism in absence and in presence of quinidine in the incubation.

The extent of metabolism without inhibitor (%) is calculated as follows:

$$\frac{(NCE \text{ response in samples without inhibitor})\text{time } 0 - (NCE \text{ response in samples without inhibitor})\text{time } 30}{(NCE \text{ response in samples without inhibitor})\text{time } 0} \times 100$$

The extent of metabolism with inhibitor (%) is calculated as follows:

$$\frac{(NCE \text{ response in samples without inhibitor})\text{time } 0 - (NCE \text{ response in samples with inhibitor})\text{time } 30}{(NCE \text{ response in samples without inhibitor})\text{time } 0} \times 100$$

where the NCE response is the area of the NCE divided by the area of the internal standard in the LC/MS analysis chromatogram, time0 and time30 correspond to the 0 and 30 minutes incubation time.

The % of CYP2D6 involvement is calculated as follows:

$$\frac{(\% \text{ extent of metabolism without inhibitor}) - (\% \text{ extent of metabolism with inhibitor})}{\% \text{ extent of metabolism without inhibitor}} \times 100$$

CYP2D6 Inhibitor Assay

Principle:

The CYP2D6 inhibitor assay evaluates the potential for a compound to inhibit CYP2D6. This is performed by the measurement of the inhibition of the bufuralol 1'-hydroxylase activity by the compound compared to a control. The 1'-hydroxylation of bufuralol is a metabolic reaction specific to CYP2D6. Preferred compounds of the present invention exhibit an $IC_{50}$ higher than 6 μM for CYP2D6 activity, the $IC_{50}$ being the concentration of the compound that gives 50% of inhibition of the CYP2D6 activity.

Material and Methods:

Human liver microsomes (mixture of 20 different donors, mixed gender) are acquired from Human Biologics (Scottsdale, Ariz.). β-NADPH is purchased from Sigma (St Louis, Mo.). Bufuralol is purchased from Ultrafine (Manchester, UK). All the other reagents and solvents are of analytical grade.

Microsomal incubation mixture (total volume 0.1 mL) contains bufuralol 10 μM, β-NADPH (2 mM), microsomal proteins (0.5 mg/mL), and the new chemical entity (NCE) (0, 5, and 25 μM) in 100 mM sodium phosphate buffer pH 7.4. The mixture is incubated in a shaking waterbath at 37° C. for 5 minutes. The reaction is terminated by the addition of methanol (75 μL). The samples are vortexed and the denaturated proteins are removed by centrifugation. The supernatant is analyzed by liquid chromatography connected to a fluorescence detector. The formation of the 1'-hydroxybufuralol is monitored in control samples (0 μM NCE) and in the samples incubated in presence of the NCE. The stock solution of NCE is prepared in a mixture of Acetonitrile/Water to reach a final concentration of acetonitrile in the incubation below 1.0%.

The determination of 1'hydroxybufuralol in the samples is performed by liquid chromatography with fluorimetric detection as described below. Twenty five μL samples are injected onto a Chromolith Performance RP-18e column (100 mm×4.6 mm) (Merck KGAa, Darmstadt, Germany). The mobile phase, consisting of a mixture of solvent A and solvent B whose the proportions changed according the following linear gradient, is pumped through the column at a flow rate of 1 ml/min:

| Time (minutes) | Solvent A (%) | Solvent B (%) |
|---|---|---|
| 0 | 65 | 35 |
| 2.0 | 65 | 35 |
| 2.5 | 0 | 100 |
| 5.5 | 0 | 100 |
| 6.0 | 65 | 35 |

Solvent A and Solvent B consist of a mixture of 0.02 M potassium dihydrogenophosphate buffer pH3/methanol in the proportion 90/10 (v/v) for solvent A and 10/90 (v/v) for solvent B. The run time is 7.5 minutes. Formation of 1'-hydroxybufuralol is monitored by fluorimetric detection with extinction at λ 252 nm and emission at λ 302 nm.

The $IC_{50}$ of the NCE for CYP2D6 is calculated by the measurement of the percent of inhibition of the formation of the 1'-hydroxybufuralol in presence of the NCE compared to control samples (no NCE) at a known concentration of the NCE.

The percent of inhibition of the formation of the 1'-hydroxybufuralol is calculated as follows:

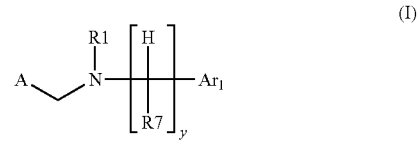

The $IC_{50}$ is calculated from the percent inhibition of the formation of the 1'-hydroxybufuralol as follows (assuming competitive inhibition):

$$\frac{NCE\ Concentration \times (100 - Percent\ of\ inhibition)}{Percent\ of\ inhibition}$$

The $IC_{50}$ estimation is assumed valid if inhibition is between 20% and 80% (Moody G C, Griffin S J, Mather A N, McGinnity D F, Riley R J. 1999. Fully automated analysis of activities catalyzed by the major human liver cytochrome P450 (CYP) enzymes: assessment of human CYP inhibition potential. Xenobiotica, 29(1): 53-75).

The invention claimed is:

1. A compound of formula (I)

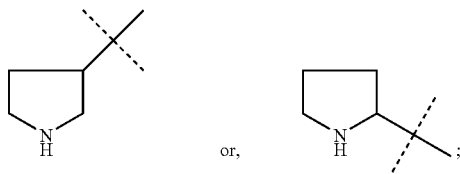

wherein
A is

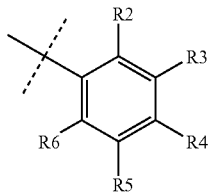

R1 is ethyl, propyl, isopropyl, isobutyl, 2,2-dimethylpropyl, cyclopentyl, cyclohexyl, cyclopropylmethyl, tetrahydrofuran-3-yl, tetrahydropyran-4-yl or 8-oxabicyclo[3.2.1]oct-6endo-yl;

R7 is independently at each occurrence selected from H and $C_1$-$C_4$alkyl;

y is 1, 2 or 3;

$Ar_1$ is wherein
R2 is H, halogen, $C_1$-$C_4$alkyl (optionally substituted with from 1 to 3 halogen atoms), —O-($C_1$-$C_4$alkyl) (optionally substituted with from 1 to 3 halogen atoms) or phenyl;

R3 is H, halogen or $C_1$-$C_4$alkyl (optionally substituted with from 1 to 3 halogen atoms);

R4 is H, halogen or $C_1$-$C_4$alkyl (optionally substituted with from 1 to 3 halogen atoms);

R5 is H, halogen or $C_1$-$C_4$alkyl (optionally substituted with from 1 to 3 halogen atoms); and R6 is H;

or a pharmaceutically acceptable salt thereof.

2. A compound as claimed in claim 1 wherein A is

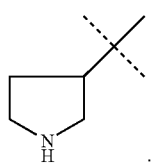

3. A compound as claimed in claim 1 wherein R7 is H.

4. A compound as claimed in claim 1 wherein y is 1.

5. A compound as claimed in claim 1 wherein at least three of R2 to R6 are H.

6. A compound as claimed in claim 1 wherein $Ar_1$ is phenyl, 2-chlorophenyl, 2-(trifluoromethyl)phenyl, 2-(difluoromethoxy)phenyl, 2-biphenyl, 3-chlorophenyl, 4-chlorophenyl, 2,3-dichlorophenyl, 2,4-dichlorophenyl, 2,4-difluorophenyl, 2-chloro-4-fluorophenyl, 2,5-dichlorophenyl, 3,4-dichlorophenyl, 3,5-dichlorophenyl, 3,5-bis(trifluoromethyl)phenyl, 4-fluoro-2-(trifuoromethyl)phenyl or 4-chloro-2-ethoxyphenyl.

7. A pharmaceutical composition comprising a compound as claimed in claim 1 or a pharmaceutically acceptable salt thereof together with a pharmaceutically acceptable diluent or carrier.

* * * * *